US010568925B2

(12) United States Patent
Melnick et al.

(10) Patent No.: US 10,568,925 B2
(45) Date of Patent: Feb. 25, 2020

(54) **EXTRACTS OF *CURCUMA AMADA* AND USES THEREOF**

(71) Applicants: DHARMA BIOMEDICAL, LLC, Miami, FL (US); FLAVEX NATUREXTRAKTE GMBH, Rehlingen (DE)

(72) Inventors: Steven J. Melnick, Coral Gables, FL (US); Karl-Werner Quirin, Beckingen (DE); Cheppail Ramachandran, Miami, FL (US); Melvin Rothberg, Weston, FL (US)

(73) Assignees: DHARMA BIOMEDICAL, LLC, Miami, FL (US); FLAVEX NATUREXTRAKTE GMBH (DE)

( * ) Notice: Subject to any disclaimer, the term of this patent is extended or adjusted under 35 U.S.C. 154(b) by 616 days.

(21) Appl. No.: 15/011,628

(22) Filed: Jan. 31, 2016

(65) Prior Publication Data
US 2016/0220627 A1   Aug. 4, 2016

Related U.S. Application Data

(60) Provisional application No. 62/110,062, filed on Jan. 30, 2015.

(51) Int. Cl.
| | |
|---|---|
| *A61K 36/9066* | (2006.01) |
| *A61K 31/11* | (2006.01) |
| *A61K 31/015* | (2006.01) |
| *A61K 31/01* | (2006.01) |
| *A61K 45/06* | (2006.01) |

(52) U.S. Cl.
CPC .......... *A61K 36/9066* (2013.01); *A61K 31/01* (2013.01); *A61K 31/015* (2013.01); *A61K 31/11* (2013.01); *A61K 45/06* (2013.01); *A61K 2236/37* (2013.01)

(58) Field of Classification Search
None
See application file for complete search history.

(56) References Cited

U.S. PATENT DOCUMENTS

| 6,224,877 B1 * | 5/2001 | Gaikar ............... A61K 36/9066 424/756 |
| 6,235,287 B1 | 5/2001 | Weidner et al. |

FOREIGN PATENT DOCUMENTS

EP     1045822     10/2000

OTHER PUBLICATIONS

Revilla et al. (1998) J. Agric. Food Chem. 46: 4592-4597. (Year: 1998).*
Raskin et al. (2004) Current Pharmaceutical Design, 10, 3419-3429. (Year: 2004).*
Krishna et al. (2014) Biomedicine and Biotechnology, vol. 2, No. 1, 14-19. (Year: 2014).*
Jatoi et al. (2007) Phytother. Res. 21: 5070516. (Year: 2007).*
Jambunathan, S. et al. "Cytotoxic activity of the methanolic extract of leaves and rhizomes of *Curcuma amada* Roxb against breast cancer cell lines" *Asian Pacific Journal of Tropical Medicine*, 2014, pp. S405-S409, vol. 7, Suppl. 1.
Rajamma, A. G. et al. "Antioxidant and antibacterial activities of oleoresins isolated from nine *Curcuma* species" *Phytopharmacology*, 2012, pp. 312-317, vol. 2, No. 2.
Sheeja, D. B. A. et al. "*Curcuma amada*: A rich source of bioactive compounds" Proceedings of 22nd Kerala Science Congress, Jan. 28-31, 2010, KFRI, Peechi, pp. 287-288.
Aggarwal, B. B. et al. "Anticancer Potential of Curcumin: Preclinical and Clinical Studies" *Anticancer Research*, 2003; 23:363-398.
Bhaskaran, A. et al. "Clinical Evaluation of Amragandha Haridra (*Curcuma amada* ROXB) in Pratisyaya W.S.R. to Allergic Rhinitis: A Folklore Claim" *International Journal of Research in Ayurveda and Pharmacy*, Jan.-Feb. 2012; 3(1):85-89.

(Continued)

*Primary Examiner* — Russell G Fiebig
(74) *Attorney, Agent, or Firm* — Saliwanchik, Lloyd & Eisenschenk

(57) ABSTRACT

The invention concerns carbon dioxide extracts of *Curcuma amada* (mango ginger), including supercritical carbon dioxide extracts of *C. amada*; methods for their production; compositions comprising the extracts; methods for treating or delaying the onset of conditions such as cell proliferation disorder (e.g., cancer), inflammation, infection, hyperlipidemia, hypercholesterolemia, hypertriglyceridemia, hyperglycemia, platelet hyper-aggregation, immune disorder such as autoimmune disorder, or neurodegenerative condition; and methods for inhibiting expression of Bcl-2, Bak, and p53 genes; inhibiting expression of the COX-2 and NF-kB genes, inhibiting production of phosphorylated target of rapamycin (TOR), modulating AMP-activated protein kinase (AMPK), inhibiting protein kinase B (AKT) signaling, modulating the Ras/Raf/MEK/ERK signaling pathway, and modulating the Ras/PI3K/PTEN/Akt/mTOR signaling pathway. Another aspect of the invention concerns a method for inhibiting contamination, comprising applying the extract or composition of the invention to a surface. Another aspect of the invention concerns a method for promoting longevity of a cell in vitro or in vivo, comprising contacting a target cell in vitro or in vivo with an effective amount of the extract or composition of the invention. Another aspect of the invention concerns a method for promoting longevity of a subject, comprising administering an effective amount of the extract or composition of the invention. Another aspect of the invention concerns a method for inhibiting the metabolism of a cancer cell, comprising contacting the target cancer cell in vitro or in vivo with an effective amount of the extract or composition of the invention. Another aspect of the invention concerns a kit including the extract or composition; a container containing the extract or composition; and packaging material.

12 Claims, 33 Drawing Sheets

(56) References Cited

OTHER PUBLICATIONS

Chandarana, H. et al. "Comparison of Antibacterial Activities of Selected Species of Zingiberaceae Family and Some Synthetic Compounds" *Turkish Journal of Biology*, 2005; 29:83-97.
Chappell, W. H. et al. "Ras/Raf/MEK/ERK and PI3K/PTEN/Akt/mTOR Inhibitors: Rationale and Importance to Inhibiting These Pathways in Human Health" *Oncotarget*, Mar. 2011; 2(3):135-164.
Cheah, Y. H. et al. "Xanthorrhizol Exhibits Antiproliferative Activity on MCF-7 Breast Cancer Cells via Apoptosis Induction" *Anticancer Research*, 2006; 26:4527-4534.
Chirangini, P. et al. "Sulfur free radical activity with curcumin as reference for evaluating antioxidant properties of medicinal Zingiberales" *Journal of Environmental Pathology, Toxicology and Oncology*, 2004; 23:227-236.
Choi, M-A. et al. "Xanthorrihizol, a natural sesquiterpenoid from *Curcuma xanthorrhiza*, has an anti-metasttic potential in experimental mouse lung metastasis model" *Biochemical and Biophysical Research Communications*, 2005; 326:210-217.
Firuzi, O. et al. "Antioxidant Therapy: Current Status and Future Prospects" *Current Medicinal Chemistry*, 2011; 18:3871-3888.
Gerard, D. and Quirin, K-W. "Extraction of Pharmaceutically Active Components", pp. 142-143 of chapter IV.3.C. of Stahl, E. et al. (Eds.) "Dense Gases for Extraction and Refining" Springer-Verlag, New York Heidelberg Berlin; ISDN 0-387-18158-X; 1988.
Gholap, A. S. et al. "Characterization of Mango-like Aroma in *Curcuma amada* Roxb" *Journal of Agricultural and Food Chemistry*, 1984; 32:57-59.
Ghosh, S. B. et al. "Antifungal activity in rhizomes of *Curcuma amada* Roxb." *Indian Journal of Experimental Biology*, 1980; 18:174-176, abstract.
Gonzalez, M. A. et al. "Synthesis and biological evaluation of (+)-labdadienedial, derivatives and precursors from (+)-sclareolide" *European Journal of Medicinal Chemistry*, 2010; 45:4403-4408.
Islam, A. "Genetic diversity of the genus *Curcuma* in Bangladesh and further biotechnological approaches for in vitro regeneration and long-term conservation of *Curcuma longa* germplasm" Ph.D. thesis, University of Hanover, Germany; 2004.
Jatoi, S. A. et al. "Phytochemical, Pharmacological and Ethnobotanical Studies in Mango Ginger (*Curcuma amada* Roxb.; Zingiberaceae)" *Phytotherapy Research*, 2007; 21:507-516.
Kang, Y-J. et al. "Xanthorrhizol, a Natural Sesquiterpenoid, Induces Apoptosis and Growth Arrest in HCT116 Human Colon Cancer Cells" *Journal of Pharmacological Sciences*, 2009; 111:276-284.
Kirtikar, K. R. et al. "Indian Medicinal Plants" 1984; vol. 4, second edition, pp. 2422-2423.
Malek, S. N. A. et al. "Phytochemical and Cytotoxic Investigations of *Curcuma mangga* Rhizomes" *Molecules*, 2011; 16:4539-4548.
McCubrey, J. et al. "Ras/Raf/MEK/ERK and PI3K/PTEN/Akt/mTOR Cascade Inhibitors: How Mutations Can Result in Therapy Resistance and How to Overcome Resistance" *Oncotarget*, 2012; 3(10):1068-1111.
Mujumdar, A. M. et al. "Antiinflammatory Activity of *Curcuma amada* Roxb. in Albino Rats" *Indian Journal of Pharmacology*, 2000; 32:375-377.
Niranjan, A. et al. "Biochemical Composition of *Curcuma longa* L. Accessions" *Analytical Letters*, 2013, 46(7):1069-1083.
Niranjan, A. et al. "Chemistry of *Curcuma* species cultivated on sodic soil" *J Med Aromat Plant Sci.*, 2003, 25:69-75, abstract.
Park, J. H. et al. "Cancer Chemoprotective Effects of *Curcuma xanthorrhiza*" *Phytotherapy Research*, 2008; 22:695-698.
Perry, M-C. et al. "Curcumin inhibits tumor growth and angiogenesis in glioblastoma xenografts" *Molecular Nutrition Food Research*, 2010; 54:1192-1201.
Policegoudra, R. S. et al. "Identification of difurocumenonol, a new antimicrobial compound from mango ginger (*Curcuma amada* Roxb.) rhizome" *Journal of Applied Microbiology*, 2007; 102:1594-1602.

Policegoudra, R. S. et al. "Isolation and characterization of antioxidant and antibacterial compound from mango ginger (*Curcuma amada* Roxb.) rhizome" *Journal of Chromatography*, 2007; B852:40-48.
Policegoudra, R. S.. "Functional properties of bioactive molecules from mango ginger (*Curcuma amada* Roxb.) and its applications in food" Ph.D. Thesis, Mysore University, Mysore, India; 2008.
Policegoudra, R. S. et al. "Antimicrobial, antioxidant, cytotoxicity and platelet aggregation Inhibitory activity of a novel molecule isolated and characterized from mango ginger (*Curcuma amada* Roxb.) rhizome" *Journal of Bioscience*, 2010; 35:231-240.
Policegoudra, R. S. et al. "Mango ginger (*Curcuma amada* Roxb.)—A promising spice for phytochemicals and biological activities" *Journal of Bioscience*, 2011; 36(4):739-748.
Policegoudra, R. S. et al. "Cytotoxicity, Platelet Aggregation Inhibitory and Antioxidant Activity of *Curcuma amada* Roxb. Extracts" *Food Technology and Biotechnology*, 2011; 49(2):162-168.
Ramachandran, C. et al. "Potentiation of gemcitabine by Turmeric Force™ in pancreatic cancer cell lines" *Oncology Reports*, 2010; 23:1529-1535.
Ramachandran, C. et al. "Potentiation of Etoposide and Temozolomide Cytotoxicity by Curcumin and Turmeric Force™ in Brain Tumor Cell Lines" *Journal of Complementary Integrative Medicine*, 2012; 9(1):Article 20, 1-14.
Ramachandran, C. et al. "Adjuvant therapeutic use of supercritical-ethanol extracts of *Curcuma* species with cancer drugs in rhabdomycosarcoma cell lines" presented at: Joint Meeting of AFERP, ASP, GA, PSE, and SIF, New York City, Aug. 2012, Abstract PI137.
Ramachandran, C. et al. "Anticancer effects of supercritical extracts of *Curcuma* species in human rhabdomyosarcoma and brain tumor cells in vitro and in vivo" presented at: Intl. Conf. Translational Cancer Res., New Delhi, Feb. 2014, Abstract S24.
Ramachandran, C. et al. "Anticancer Potential and Mechanism of Action of Mango Ginger (*Curcuma amada* ROXB.) Supercritical Extracts in Human Glioblastoma Cell Lines" presented at Neuro-Oncology, Oct. 15, 2014, Abstract ET-49.
Ramachandran, C. et al. "Therapeutic Effect of Supercritical CO2 Extracts of *Curcuma* Species with Cancer Drugs in Rhabdomyosarcoma Cell Lines" *Phytotherapy Research*, Aug. 2015; 29:1152-1160.
Ramachandran, C. et al. "Anticancer Potential and Mechanism of Action of Mango Ginger (*Curcuma amada* Roxb.) Supercritical CO2 Extract in Human Glioblastoma cells" *Journal of Evidence-Based Complementary & Alternative Medicine*, Apr. 2015; 20(2):109-119.
Rao, A. S. et al. "Volatile aroma components of *Curcuma amada* Roxb." *Journal of Agriculture and Food Chemistry*, 1989; 37:740-743.
Samant, L. "*Curcuma amada* Roxb.: A Phytopharmacological Review" *Journal of Pharmacological Research*, 2012; 5(4):1992-1993.
Sheeja, A. D. B. et al. "Facile isolation of (E)-labda-8(17),12-diene-15,16-dial from *Curcuma amada* and its conversion to other biologically active compounds" *Indian Journal of Chemistry*, 2014; 53B:319-324.
Sheeja, A. D. B. et al. "Phytochemical constituents of *Curcuma amada*" *Biochemical Systems and Ecology*, 2012; 44:264-266.
Singh, G. et al. "Chemical and biocidal investigations on essential oils of some Indian *Curcuma* species" *Progress in Crystal Growth and Characterization Materials*, 2002; 45:75-81.
Singh, G. et al. "A bioactive labdane diterpenoid from *Curcuma amada* and its semisynthetic analogues as antitubercular agents" *European Journal of Medicinal Chemistry*, 2010; 45:4379-4382.
Singh, G. et al. "Determination of anti-tubercular agent in mango ginger (*Curcuma amada* Roxb.) by reverse phase HPLC-PDA-MS, chapter 2.4" *Food Chemistry*, 2012; 131:375-379.
Steelman, L. et al. "Roles of the Raf/MEK/ERK and PI3K/PTEN/Akt/mTOR pathways in controlling growth and sensitivity to therapy—implications for cancer and aging" *Aging*, 2011; 3(3):192-222.
Tee, T. T. et al. "Xanthorrhizol induced DNA fragmentation in HepG2 cells involving Bcl-2 family proteins" *Biochemical and Biophysical Research Communications*, 2012; 420:834-838.
Warrier, P. K. et al. Indian medicinal plants—a compendium of 500 species, Chennai: Orient Longman Pvt. Ltd., 1994; 1:106, abstract.

(56) References Cited

OTHER PUBLICATIONS

Aïd, S. and Bosetti, F. "Targeting cyclooxygenases-1 and -2 in neuroinflammation: therapeutic implications" *Biochimie*, 2011, 93(1):46-51.

Boehm, E.M. et al. "The many roles of PCNA in eukaryotic DNA replication" *Enzymes*, 2016, 39:231-254.

Chaturvedi, M.M. et al. "NF-κB addiction and its role in cancer: 'one size does not fit all'" *Oncogene*, 2011, 30(14):1615-1630.

Choi, S-H. et al. "The distinct roles of cyclooxygenase-1 and -2 in neuroinflammation: implications for translational research" *Trends Pharmacol Sci.*, 2009, 30(4):174-181.

Chong, Z.Z. et al. "Mammalian target of rapamycin. Hitting the bull's-eye for neurological disorders" *Oxidative Medicine and Cellular Longevity*, 2010, 3(6):374-391.

Claar, D. et al. "The Role of Prostaglandins in Allergic Lung Inflammation and Asthma" *Expert Rev Respir Med.*, 2015, 9(1):55-72.

Cobbold, S.P. "The mTOR pathway and integrating immune regulation" *Immunology*, 2013, 140:391-398.

Hoesel, B. and Schmid, J.A. "The complexity of NF-κB signaling in inflammation and cancer" *Molecular Cancer*, 2013, 12:86 (15 pages).

Kelman, Z. "PCNA: structure, functions and interactions" *Oncogene*, 1997, 14:629-640.

Lee, D-F. and Hung, M-C. "All Roads Lead to mTOR: Integrating Inflammation and Tumor Angiogenesis" *Cell Cycle*, 2007, 6(24):3011-3014.

Mahajan, A. and Sharma, R. "COX-2 Selective Nonsteroidal Anti-inflammatory Drugs : Current Status" *Journal of the Association of Physicians of India*, 2005, 53:200-204.

Mango Ginger CO2-to extract, 35 % LDD, standardised with Olive oil, Type No. 184.003. Product Brochure. FLAVEX Naturextrakte GmbH, 2015, 2 pages.

Powell, J.D. et al. "Regulation of Immune Responses by mTOR" *Annu Rev Immunol.*, 2012, 30:39-68.

Punchihewa, C. et al. "Identification of Small Molecule Proliferating Cell Nuclear Antigen (PCNA) Inhibitor That Disrupts Interactions with PIP-box Proteins and Inhibits DNA Replication" *J. Biol. Chem.*, 2012, 287(17):14289-14300.

Ricciotti, E. and Fitzgerald, G.A. "Prostaglandins and Inflammation" *Arterioscler Thromb Vasc Biol.*, 2011, 31(5):986-1000.

Shih, R-H. et al. "NF-kappaB Signaling Pathways in Neurological Inflammation: A Mini Review" *Front. Mol. Neurosci.*, 2015, vol. 8, Article 77, pp. 1-8.

Viatour, P. et al. "Phosphorylation of NF-kB and IkB proteins: implications in cancer and inflammation" *TRENDS in Biochemical Sciences*, Jan. 2005 (EPUB Dec. 2004), 30(1):43-52.

Waickman, A.T. and Powell, J.D. "mTOR, metabolism, and the regulation of T-cell differentiation and function" *Immunol Rev.*, 2012, 249(1):43-58.

Weichhart, T. et al. "Regulation of innate immune cell function by mTOR" *Nat Rev Immunol.*, 2015, 15(10):599-614.

Wu, T. et al. "Regulation of Cyclin B2 Expression and Cell Cycle $G_2/M$ Transition by Menin" *J. Biol. Chem.*, 2010, 285(24):18291-18300.

\* cited by examiner

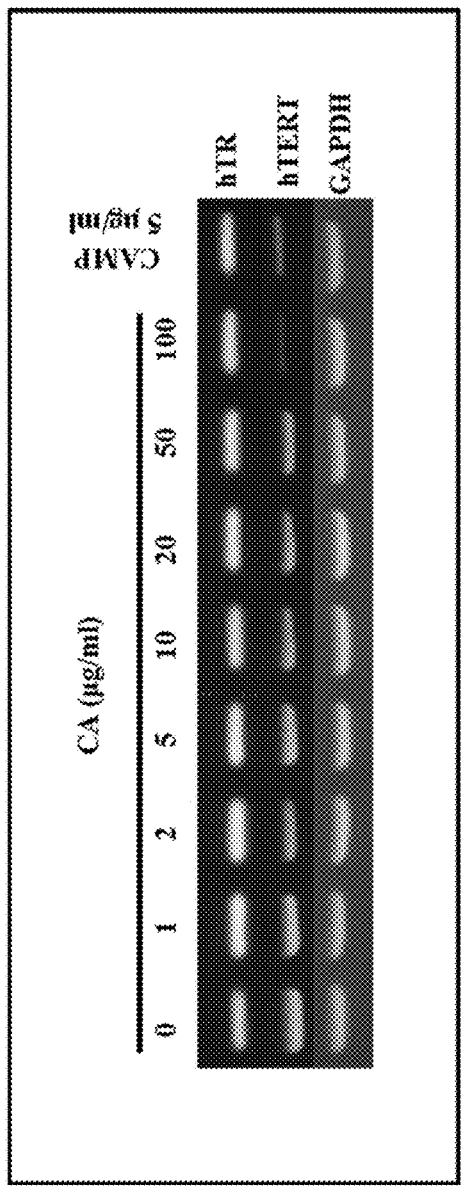
FIG. 8
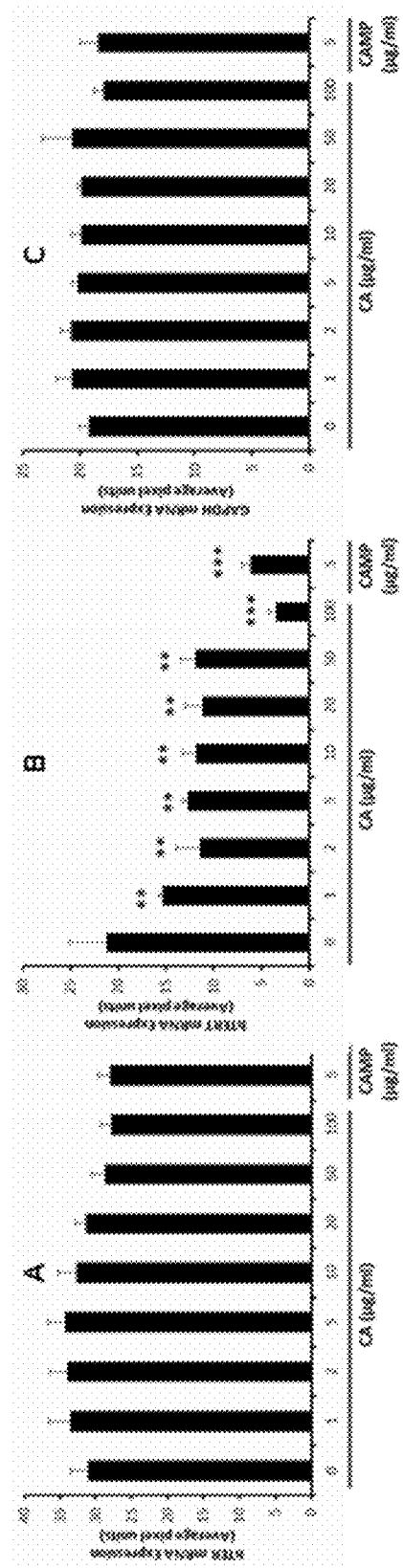
FIG. 9A
FIG. 9B
FIG. 9C

EXTRACTS OF *CURCUMA AMADA* AND USES THEREOF

CROSS-REFERENCE TO RELATED APPLICATION

The present application claims the benefit of U.S. Provisional Application Ser. No. 62/110,062, filed Jan. 30, 2015, which is hereby incorporated by reference herein in its entirety, including any figures, tables, nucleic acid sequences, amino acid sequences, or drawings.

BACKGROUND OF THE INVENTION

The genus *Curcuma* contains over 80 species of rhizomatous herbs of which many have significant value as medicines, dyes and spices (Islam 2004). *Curcuma amada* Roxb. is an important member of the genus commonly known as mango ginger due to the raw mango-like aroma of the rhizome. It has a morphological and phylogenic resemblance with ginger (*Zingiber officinale*) but imparts mango (*Mangifera indica*) flavor. Mango flavor is in part attributed to cis-ocimene among the 68 volatile aroma components present in the essential oil of mango ginger rhizome (Achut and Bandyopadhyaya 1984; Srinivas et al. 1989; Singh et al. 2002; Singh et al. 2003). Ethnobotanically, it is used for treating stomach aches, itching, skin diseases, bronchitis, asthma, hiccough and inflammation due to injuries (Kirtikar and Basu 1984; Warrier et al. 1994). It is also described as a useful agent against inflammation of the mouth, ulcers of the male genitalia, scabies, lumbago and stomatitis (Kirtikar and Basu 1984; Warrier et al. 1994; Hussain et al. 1992). The ethanol extract of *Curcuma amada* displayed antifungal activity and broad spectrum of antibacterial activity against several strains (Policegoudra et al. 2011). In addition to a sequiterpene dimer 'difurocumenonol' (Policegoudra et al. 2007a) and a substituted sesquiterpene 'amadannulen' (Policegoudra et al. 2007b), six diterpinoids have been isolated so far from the rizhiomes of mango ginger, of which the (E)-labda 8(17), 12-diene-15, 16 dial is the major ingredient (Singh et al. 2010; Sheeja and Nair 2012). The (E)-labda-8(17), 12-diene-15,16 dial, a novel dialdehyde isolated from the chloroform extract of rhizomes of *Curcuma amada* has anti-tubercular activity against *Mycobacterium tuberculosis* H37Rv strain in BACTEC-460 assay (Singh et al. 2010). This compound is also reported to have antifungal activity against several *Candida* species, mosquitocidal activity against *Aedes aegyptii* larvae and cytotoxicity against KB cervical carcinoma cells (Sheeja and Nair 2012; Sheeja and Nair 2014).

*C. amada* is among the less-investigated species within the genus *Curcuma*, especially for its anticancer and other medicinal properties. However, it is a well-described herb in the Indian Ayuvedic system of medicine (Kirtikar and Basu 1984; Warrier et al. 1994; Hussain et al. 1992). Pharmacologically, mango ginger has been used against a variety of human ailments. Traditionally, it is used for treating skin allergies (Majumdar et al. 2000), stomach problems (Hussain et al. 1992), and hypercholesterolemia (Pachauri and Mukherjee 1970). It has also been shown to possess antioxidant (Chirangini et al. 2004; Niranjan et al. 2003) and antibacterial activity (Chandrana et al. 2005; Ghosh et al. 1980). More than 130 chemical constituents have been reported in *C. amada* rhizomes, of which 121 have been identified (Jatoi et al. 2007). Policegoudra et al. (Policegoudra et al. 2007a; Policegoudra et al. 2010) have identified difurocumenonol, a new antimicrobial compound from mango ginger rhizome. The major chemical components of mango ginger rhizome that have been reported include (E)-labda-8(17), 12-diene-15, 16 dial (Singh et al. 2010; Sheeja and Nair 2014), starch, phenolic acids, volatile oils, curcuminoids and terpenoids like difurocumenonol, amadannulen and amadaldehyde (Policegoudra et al. 2011). However, it is not clear whether curcuminoids are in fact a constituent of mango ginger rhizome which has a pale yellow color similar to ginger and not orange as in turmeric. Discrepancies in the literature may occur, due in part to misidentification of raw materials. For example, species such as *Curcoma mangga* referred to as mango-like turmeric contains curcuminoids and (E)-labda 8(17), 12-diene-15, 16 dial (Malek et al. 2011). Compounds such as difurocumenonol and amadaldehyde have been demonstrated to possess anticancer activity (Policegoudra et al. 2010; Gonzalzez et al. 2010).

BRIEF SUMMARY OF THE INVENTION

The inventors have determined that a supercritical carbon dioxide ($CO_2$) extract (CA) prepared from mango ginger of (*Curcuma amada*) rhizomes has superior anticancer activity against human rhabdomyosarcoma and glioblastoma cell lines, relative to *Curcuma longa* (turmeric) and *C. xanthorrhiza* supercritical extracts. Moreover, CA was demonstrated to have synergistic cytotoxicity with chemotherapeutic agents commonly used for treatment of rhabdomyosarcoma and brain cancer patients. In addition to analyzing the mechanisms of action of CA in rhabdomyosarcoma and glioblastoma cell lines in culture, the inventors have evaluated the anticancer potential of CA against glioblastoma and rhabdomyosarcoma in vivo in xenograft animal models.

One aspect of the invention concerns a carbon dioxide extract of *Curcuma amada*, for example, a supercritical carbon dioxide extract or a liquid carbon dioxide extract of *C. amada*. In some embodiments, the extract comprises at least about 5% (E)-Labda-8(17),12-diene-15,16-dial (LDD). In some embodiments, in addition to LDD, the extract comprises α-pinene, camphene, β-pinene, β-myrcene, limonene, β-phellandrene, β-cariophyllene, ar-curcumene, and α-zingiberene.

The inventors have determined that ethanol is not needed for LDD extraction (pure carbon dioxide is sufficient). Where ethanol is used as a co-solvent, LDD is largely destroyed if ethanol is distilled from the resulting extract. However, to the extent *C. amada* is extracted with carbon dioxide and a small percentage of ethanol is used as a co-solvent, if the ethanol is not removed, the alcohol solution (tincture) may be a suitable product as well. Therefore, in some embodiments, the carbon dioxide extract of *C. amada* is produced with no more than 10% ethanol as a co-solvent. In some embodiments, the carbon dioxide extract is not the product of ethanol co-extraction (i.e., is produced with zero percent (0%) of ethanol as a co-solvent).

Another aspect of the invention concerns a method for producing a carbon dioxide extract of *Curcuma amada*, comprising subjecting *C. amada* material to carbon dioxide extraction, such as supercritical carbon dioxide extraction or liquid carbon dioxide extraction resulting in a supercritical carbon dioxide or liquid carbon dioxide extract of *C. amada*. In some embodiments, the carbon dioxide extract of *C. amada* is produced with no more than 10% ethanol as a co-solvent. In some embodiments, the carbon dioxide extract is not the product of ethanol co-extraction (i.e., is produced with zero percent (0%) of ethanol as a co-solvent). In some embodiments, the method includes no co-solvent extraction. In some embodiments, the method does not include boiling. In some embodiments, the method includes no co-solvent extraction or boiling.

Another aspect concerns a composition comprising the carbon dioxide extract (e.g., the supercritical carbon dioxide extract or liquid carbon dioxide extract); and a carrier or excipient. In some embodiments, the composition further comprises an agent selected from among a botanical extract, mineral, vitamin, nutrient, other nutraceutical, dietary supplement, or active pharmaceutical ingredient, such as a chemotherapeutic agent.

In some embodiments, the composition further comprises a natural or synthetic oil, such as one or more medium chain triglycerides. In some embodiments, the oil is vegetable oil. In some embodiments, the oil is selected from among olive oil, chia seed oil, soy germ oil, pomegranate oil, fish oil, and seafood oil.

In some embodiments, the composition further comprises a botanical extract selected from among a sterol, sterone, steroid, polyphenol, flavonoid, terpenoid, alkaloid, or a polysaccharide.

In some embodiments, the composition further comprises an antioxidant.

Another aspect of the invention concerns a method for treating an existing condition in a subject as a therapy, or preventing or delaying the onset of a condition as a prophylaxis, in a subject, comprising administering an effective amount of a carbon dioxide extract of C. amada described herein (e.g., a supercritical carbon dioxide extract of C. amada or liquid extract of C. amada; or composition of the invention. In some embodiments, the carbon dioxide extract of C. amada is produced with no more than 10% ethanol as a co-solvent. In some embodiments, the carbon dioxide extract is not the product of ethanol co-extraction (i.e., is produced with zero percent (0%) of ethanol as a co-solvent).

In some embodiments, the condition is selected from the group consisting of a cell proliferation disorder (e.g., cancer), arteriosclerotic vascular disease, inflammation (acute or chronic inflammation), fever, infection, hyperlipidemia, hypercholesterolemia, hypertriglyceridemia, hyperglycemia, platelet hyper-aggregation, aged and/or sun-damaged skin, immune disorder such as an autoimmune disorder, or neurodegenerative condition (associated with a disease process or trauma). In some embodiments, the cell proliferation disorder is cancer. The extract or composition may be administered to a subject as a monotherapy, or in simultaneous or sequential combination with other treatments. In some embodiments, the extract or composition is used with one or more additional agents. For example, the additional agents may have an activity useful for treating the condition independently, and/or have an activity that enhances the effect of the extract or composition of the invention. The additional agents may be administered to a subject or brought into contact with cells in vitro or in vivo simultaneously, or consecutively (sequentially) in any order. If administered to a subject or brought into contact with cells, the extract of the invention and the one or more additional agents may be administered or brought in contact with cells separately in separate formulations, or together within one formulation (one composition).

Another aspect of the invention concerns a method for inhibiting expression of Bcl-2, Bak, and p53 genes; inhibiting expression of the COX-2 and NF-kB genes; inhibiting production of phosphorylated target of rapamycin (TOR); modulating AMP-activated protein kinase (AMPK); inhibiting protein kinase B (AKT) signaling, modulating the Ras/Raf/MEK/ERK signaling pathway, and modulating the Ras/PI3K/PTEN/Akt/mTOR signaling pathway, wherein the method comprises contacting a target cell in vitro or in vivo with an effective amount of an extract of C. amada described herein, or with a composition comprising the extract described herein.

Another aspect of the invention concerns a method for inhibiting contamination, comprising applying the extract or composition described herein to a surface.

Another aspect of the invention concerns a kit comprising an extract or composition described herein; a container containing the extract or composition; and packaging material.

BRIEF DESCRIPTION OF THE DRAWINGS

FIG. 5A: STAT3; FIG. 5B: p21; FIG. 5C: p10; FIG. 5D: Bcl-2; FIG. 5E: Bax; FIG. 5F: p53; FIG. 5G: APOBEC; FIG. 5H: Bax/Bcl-2; and FIG. 5I: GAPDH. (*p<0.05; p<0.01; *p<0.001).

FIG. 7A: PCNA; FIG. 7B: K167; FIG. 7C: CCNB2; and FIG. 7D: GAPDH. (p<0.01; *p<0.001).

FIG. 8: RT-PCR assay of gene expression associated with telomerase activity (hTER and hTERT) along with GAPDH in U-87MG cell line.

FIGS. 9A-9C: Quantification of expression of genes associated with telomerase activity by UNSCAN-IT gel software. The relative expression of gene (average pixel units) was plotted against CA concentrations. The significant difference between treatments was compared by 1-way ANOVA with Dunnett's multiple comparison test (GraphPad Prism software, La Jolla, Calif.). FIG. 9A: hTER; FIG. 9B: hTERT; and FIG. 9C: GAPDH. ($p<0.01$; *$p<0.001$).

FIG. 11A: MDR-1; FIG. 11B: LRP; FIG. 11C: MRP; FIG. 11D: DRP; and FIG. 11E: GAPDH. (*$p<0.1$).

FIG. 13A: N-myc; FIG. 13B: V-Jun; FIG. 13C: C-myc; and FIG. 13D: GAPDH. (*$p<0.05$; **$p<0.01$).

FIG. 18A: dose-effect plots of vinblastine (VBL), cyclophosphamide (CP), Curcuma amada supercritical $CO_2$ extract (CA); FIG. 18B: dose-effect plots of combinations CP+CA, VBL+CA and CP+VBL+CA (P+V+A); FIG. 18C: medium-effect plots of individual drugs CP, VBL and CA; FIG. 18D: medium-effect plots of combinations CP+CA, VBL+CA and CP+VBL+CA (P+V+A).

FIG. 23A: COX-2; FIG. 23B: NF-Kb; FIG. 23C: STAT3; and FIG. 23D: GAPDH.

DETAILED DESCRIPTION OF THE INVENTION

Figure 1:
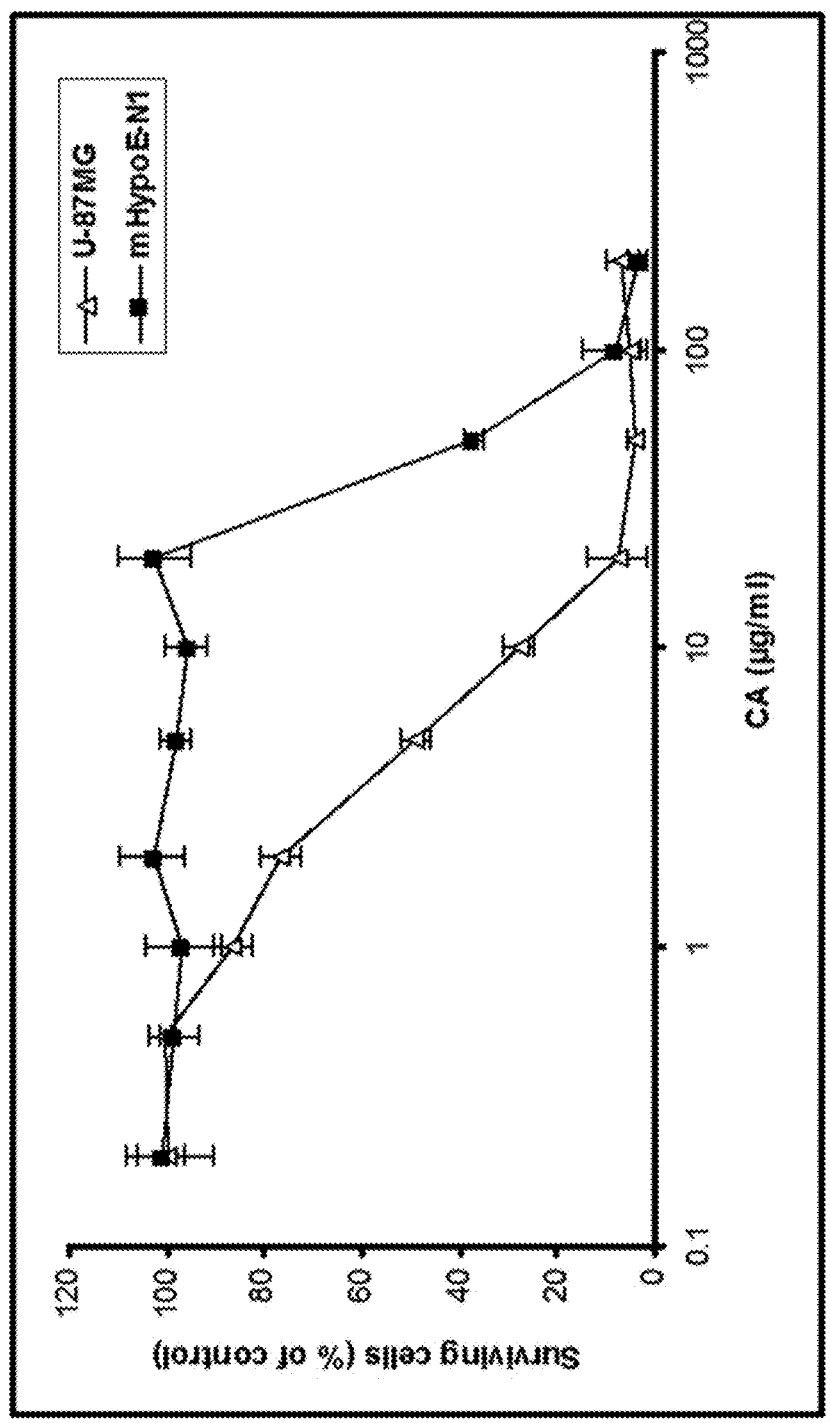
FIG. 1: Cytotoxicity of Curcuma amada supercritical $CO_2$ extract (CA) in U-87MG human glioblastoma and normal mouse embryonic hypothalamus (mHypoE-N1) cell lines. Tumor cells were treated with CA for 72 h and cytotoxicity analyzed by MTT assay. The mean percentage of surviving cells (n=4) and standard deviation estimates were plotted against CA concentrations.
Figures 2A, 2B, 2C, 2D:
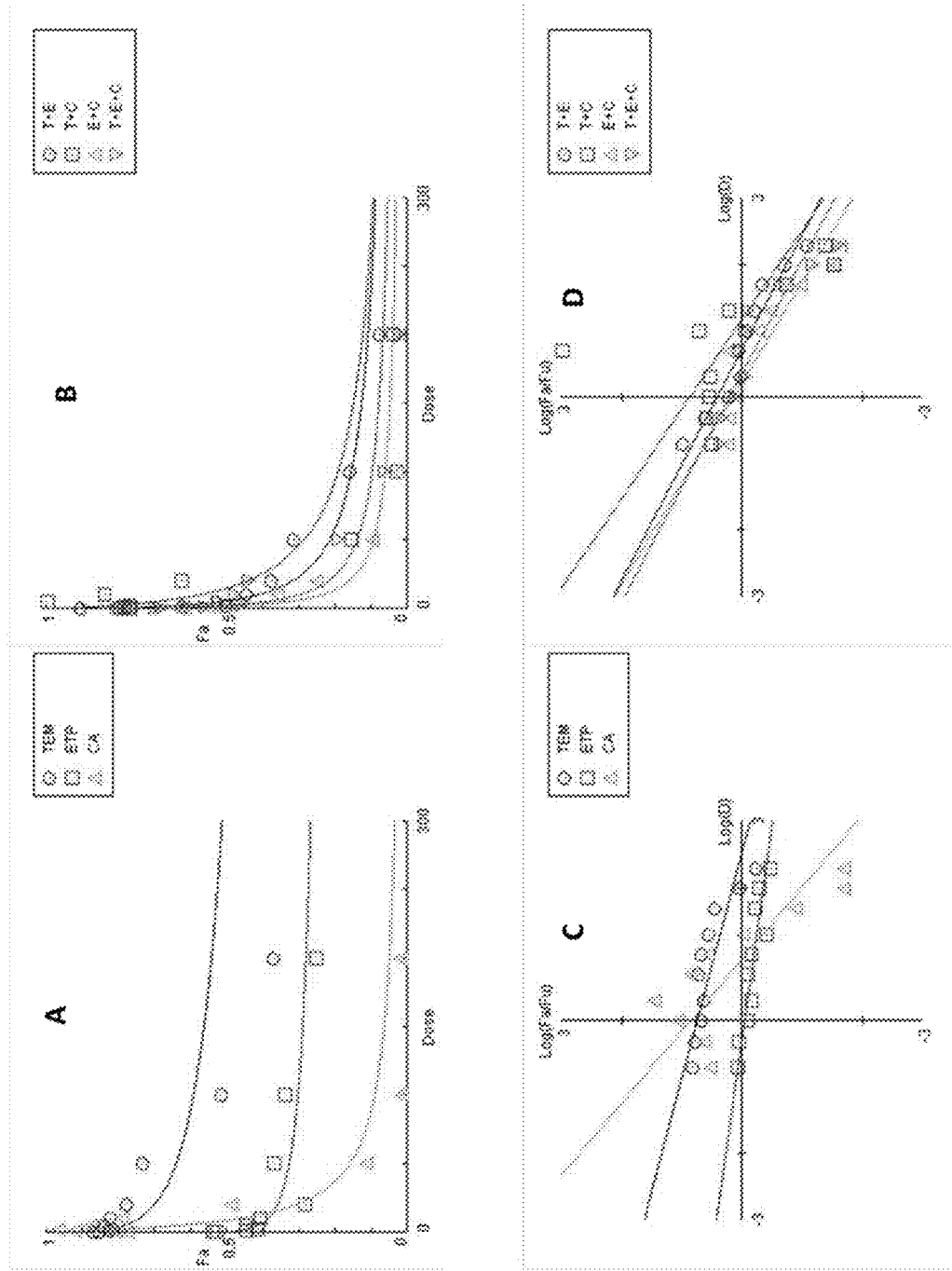
FIGS. 2A-2D: CompuSyn analysis of cytotoxicity data to determine synergism/additiveness/antagonism between cancer drugs and CA in U-87MG cell line. Dose-effect plots of single agents (FIG. 2A) [temozolomide (TEM), etoposide (ETP) and supercritical $CO_2$ extract of Curcuma amada (CA)] and drug and/or extract combinations (FIG. 2B) (T+E=temozolomide+etoposide; T+C=temozolomide+CA; E+C=etoposide+CA; T+E+C=temozolomide+etoposide+ CA) in U-87MG cell line. Medium-effect plots of single agents (FIG. 2C) and drug and/or extract combinations (FIG. 2D).

The inventors have investigated the anticancer properties of the supercritical $CO_2$ extract of mango ginger (CA) in human U-87MG glioblastoma cells and explored the molecular pathways underlying the substantial cytotoxicity demonstrated by CA, described in Examples 1-6. The results showed that CA is 8.5 times more cytotoxic to a glioblastoma cell line (U-87MG) than a normal hypothalamus cell line (mHypoE-N1), which indicates the specificity of CA towards brain tumor cells (see Example 1).

To understand the molecular changes induced by CA treatment, the inventors analyzed the expression of genes associated with apoptosis (STAT3, P10, p21, Bax, APOBEC3B, P53 and Bcl-2), cell proliferation (Ki67 and PCNA), telomerase activity (hTER and hTERT), drug resistance (MDR-1, MRP, LRP and DRP) and oncogenesis (C-myc, N-myc and V-jun), described in Examples 4 and 5. Increasing concentrations of CA down-regulate the mRNA expression of genes such as STAT3, Bcl-2, p53 and increases the Bax/Bcl-2 ratio, which could be a favoring factor for apoptosis. The inventors also observed an increase in the percentage of cells undergoing apoptosis with increasing CA concentrations (see Example 3). This would indicate that the cytotoxicity of CA in U-87MG cells may be contributed predominantly by the induction of apoptosis. The changes in the Bax and Bcl-2 expression with CA treatment of U-87MG cells is noteworthy since it has a direct relationship on apoptosis (Speirs et al. 2011). Oltivai et al. (Oltivai et al. 1993) reported that Bax accelerates apoptotic cell death, without any alteration of cell division and viability. According to Oltivai et al., Bax synthesis does not appear to be a de novo response following a death stimulus and Bax by itself does not cause cell death. Bax also counters the death repressor activity of Bcl-2 by Bax/Bcl-2 heterodimerization. The discovery that B-cell lymphoma 2 (Bcl-2), a protein overexpressed in many types of cancer cells, promotes cell survival but not cell proliferation (Vaux et al. 1988) has led to the view that impaired apoptosis is a critical step in tumor development (Hanahan and Weinberg 2000). The central mechanisms in the mitochondrial pathway related to programmed cell death is the extended Bcl-2 family of proteins. In mammalian cells, five pro-survival proteins like Bcl-2 and Bcl-X antagonize the pro-apoptotic function of Bak and Bax (Youle and Strasser et al. 2008).

In the pathway associated with cell proliferation, CA treatment down-regulates PCNA and cyclin B2 (CCNB2) mRNA expression in U-87MG cells. Since PCNA is actively involved in DNA synthesis and cell proliferation of tumor cells, inhibition of the process by CA would be advantageous for its therapeutic development. It is also reported that PCNA can form a complex with p21 resulting in the inhibition of DNA replication (Li et al. 1994). The cyclin B2 is associated with p34cdc2 and both are considered to be essential components of the cell cycle regulatory machinery and primarily associated with the Golgi region (Gong and Ferrell Jr 2010). CA treatment also appears to down-regulate the expression of drug resistance genes like LRP and MRP to a low extent. U-87MG cells have low MDR-1 expression and CA treatment did not cause any change in it. However, the down-regulation of MRP and LRP mRNAs with CA treatment would be a desirable attribute.

Telomerase has been frequently described as an ideal cancer target mainly because it is activated in approximately 85% of human cancers (Shay and Bacchetti 1997; Greider 1998). On the contrary, telomerase activity tends to be very low in normal somatic cells except stem cells. The inventors have demonstrated that CA inhibits the expression of hTERT mRNAs and not hTER in human glioblastoma cells (see Example 4). It is argued that the down-regulation of hTERT will lead to the inhibition to telomerase activity, followed by the shortening of telomeres and a final pushing of cells into a crisis state leading to apoptosis. Therefore, telomerase inhibition can be used as a good indicator for evaluating the efficiency of chemotherapeutic and chemopreventive agents. Down-regulation of hTERT expression has been reported with anti-neoplastic agents like vincristine, VP-16 and cisplatin (Lin et al. 2001). The inhibition of hTERT expression adds to the anticancer potential of CA in brain cancer cells, in addition to the inhibition of other genes associated with cell proliferation, drug resistance and promotion of apoptosis. CA treatment also has an inhibitory effect on the mRNA expression of oncogenes like N-myc and C-myc. In the regulatory pathway, C-myc is reported to be an upstream event in the regulation of hTERT (Kyo et al. 2000).

The inventors have also shown that CA demonstrates superior cytotoxicity compared to *C. longa* and *C. xanthorrhiza* extracts in rhabdomyosarcoma (RMS) cell lines (see Example 7). CA has a better cytotoxicity profile either alone or in combination with cancer drugs such as vinblastine and cyclophosphamide in RMS cell lines.

The chemical analysis of extracts showed that the total $CO_2$ extracts of *C. longa* and *C. xanthorrhiza* contained only 0.25% of curcuminoids and the *C. amada* extract had very little curcuminoids in it. *C. amada* is also unique due to the presence of a special diterpene dialdehyde with bicyclic labdane structure, (E)-labda-8(17),12-diene-15,16-dial (LDD) (Singh et al. 2012). This compound was present in the prepared *C. amada* extract at a 62% level besides the 10% of essential oil composed mainly of mono- and sesquiterpene hydrocarbons.

CA has synergistic cytotoxicity with VBL and CP in both eRMS and aRMS cell lines (see Example 8). The combination index values indicated that the VBL+CA, CP+CA and VBL+CP+CA combinations have strong synergism for cytotoxic effect. The IC values of CA were also lower than that for curcumin and TURMERIC FORCE™ supercritical turmeric extract (New Chapter, Inc., VT). Because of this enhanced modulation in cytotoxicity, it is conceivable that the concentrations of chemotherapeutic drugs such as vinblastine and cyclophosphamide in the combination therapy could be reduced while maintaining therapeutic efficacy, potentially ameliorating toxic side-effects associated with these cancer drugs. CA treatment of RMS cells in combination with VBL and CP caused an increase in the caspase 3 expression which was accompanied by an increase in percentage of apoptotic cells (see Example 9). Therefore, apoptosis appears to be one of the mechanisms contributing to the cytotoxic effect of CA in RMS cells.

CA treatment of RMS cells induced an up regulation of pro-apoptotic genes (p53, Bak and Bax) and down regulation of anti-apoptotic genes (Bcl-2) (see Example 10). The inventors have also observed an increase in the ratio of Bax/Bcl-2, Bax/Bak and Bak/Bcl-2 with CA treatment. One of the most dramatic responses to p53 activation is the induction of apoptosis (Fulda 2012). In hepatocytes, as well as in many other cell types, apoptosis occurs through either one of two major pathways described as either the intrinsic mitochondrial or extrinsic death receptor pathways (Kroemer et al. 2007; Amiral et al. 2010). In the mitochondrial pathway, death stimuli target mitochondria either directly or through transduction by proapoptotic members of the Bcl-2 family, such as Bax and Bak (Elmore 2007; Dewson and Kluck 2010). The mitochondria then release apoptogenic proteins, ultimately leading to caspase activation and apoptosis. Activation of p53 in enucleated cytoplasts is sufficient to directly or indirectly trigger apoptosis by inducing proapoptotic Bcl-2 family members (Schuler et al. 2000). In the mitochondrion, p53 induces Bax and Bak oligomerization, physically interacts with protective Bcl-$X_L$ and Bcl-2, antagonizing their antiapoptotic effects, and also forms a complex with cyclophilin D leading to disruption of mitochondrial structure (Wolff et al. 2008).

CA also down-regulated the expression of genes associated with inflammation such as Cox-2 and NF-kB but not STATS. In a detailed review on *C. amada*, Policegoudra et al. (2010; 2011) reported that ethyl acetate extract of *C. amada* has cytotoxicity, antibacterial activity, hypoglycemic activity, anti-inflammatory activity, antioxidant activity and antiallergic activity that formed his doctorate thesis (Policegoudra 2008).

Xenograft studies showed the in vivo antitumor effect of CA on aRMS tumors, described in Example 11. CA significantly inhibited tumor growth rate compared to saline treated control xenograft mice and the VBL+CA treated xenograft group showed still lower tumor growth rate than other groups. The CA and VBL+CA treated xenograft mice also have a better survival rate than the control and VBL groups in Kaplan Meier survival curve analysis. In short, xenograft studies confirmed the in vitro data on the anticancer effect of CA.

Investigations in the past two decades have established the central role of AKT (serine/threonine protein kinase B) signaling in several cellular processes critical for cancer progression, including metabolism, growth, survival and motility. Also, AKT kinases have emerged as cardinal nodes in diverse signaling cascades that regulate cell proliferation, cell size and response to nutrient availability, glucose metabolism, cell invasiveness, genome instability and angiogenesis (Bellacosa et al. 2005). Aberrant regulation of these processes are considered hallmarks of cancer (Hanahan and Weinberg 2000), and a large body of literature testifies to the frequent hyperactivation of Akt signaling in many human cancers. Several lines of evidence suggest that Akt sits at the crossroads of multiple oncogenic and tumor suppressor networks. Almost all known oncogenic growth factors, angiogenic factors and cytokines activate Akt by binding to cognate receptors on cell surface (Sun et al. 2003). Furthermore, a number of recent studies have shown that overexpression and/or activation of Akt rendor tumor cells resistant to chemotherapeutic drugs and signal molecule inhibitors such as Gleevac, Iressa, Herceptin and retinoid acid (Cheng et al. 2002; Arlt et al. 2003; Knuefermann et al. 2003; Nagata et al. 2004; Falasca 2010).

AKT is activated by phosphorylation at multiple sites. Initially the $Thr^{308}$ residue is phosphorylated, causing a charge-induced binding site conformational change. Although phophorylation at $Thr^{308}$ partially activates AKT, full activation of AKT requires phosphorylation on a second site, the $Ser^{473}$ residue, which greatly amplifies the rate of catalysis and downstream consequences of AKT activation (Woodgett 2005; Leevers et al. 1999). Interest in the understanding of the AKT pathway has been incited by its subsequent role in promoting cell survival resulting in inactivation of a series of major pro-apoptotic proteins (Leevers et al. 1999). Activated AKT is a well-established survival factor, exerting anti-apoptotic activity in part by preventing the release of cytochrome c from the mitochondria (reviewed in Whang et al., 2004). AKT also phosphorylates and inactivates the proapoptotic factors BAD and procaspase-9 (reviewed in Downward, 2004). Moreover, AKT phosphorylates and inactivates the FOXO transcription factors, which mediate the expression of genes critical for apoptosis, such sas the Fas ligand gene. AKT also activates IκB kinase (IKK), a positive regulator of NF-κB, which results in the transcription of antiapoptotic genes (reviewed in Pommier et al. 2004). In another mechanism to thwart apoptosis, AKT promotes the phosphorylation and translocation of Mdm2 into the nucleus, where it downregulates p53 and thereby antagonizes p53-mediated cell cycle checkpoints (Mayo and Donner 2002; Zhou and Hung 2002).

*C. amada* is a less studied botanical for anticancer attributes within the genus *Cucurma*. *C. amada* has a long history of traditional use in folk medicine in diverse ethnic groups and as an ingredient in culinary preparations in the Indian subcontinent. Ethnobotanically, it is used for treating stomach aches, itching, skin diseases, bronchitis, asthma, hiccough and inflammation due to injuries (Kirtikar and Basu 1984; Warrier et al. 1994). It is also described as a useful agent against inflammation of the mouth ulcer, scabies, lumbago and stoamtitis (Kirtikar and Basu 1984; Warrier et al. 1994; Hussain et al. 1992). The rhizome of the mango ginger has a morphological and phylogenic resemblance with ginger and a raw mango-like aroma. As described herein, the inventors determined that the supercritical $CO_2$ extract of mango ginger (CA) is superior in terms of its cytotoxicity in human RMS cell lines than *C. longa* and *C. xanthorrhiza* supercritical extracts (Examples 7-11). Furthermore, CA acts synergistically with anticancer drugs such as vinblastine and cyclophosphamide in regards to cytotoxicity. Through other studies described herein, the inventors have described the anti-cancer potential and mechanism of action of CA in U-87MG human glioblastoma cells (Examples 1-6). CA has shown higher cytotoxicity than temozolomide, etoposide, curcumin and Turmeric Force™ extract (New Chapter, Inc., VT), and acts synergistically with these agents in combination therapy. CA induces apoptosis in a dose-dependent manner and down-regulates genes promoting apoptosis, cell proliferation, telomerase activity, oncogenesis and drug resistance in glioblastoma cells. In addition, as described in Examples 12-15, the inventors have explored the effects of CA on the Akt signaling pathway in the U-87MG glioblastoma cell line.

CA showed greater cytotoxicity with lower IC values in U-87MG glioblastoma cell line than normal hypothalamus cell line. Therefore, tumor-specific cytotoxicity can be expected for CA treatment of patients with malignancy. Chemical analysis of CA has shown that it contains a high level of LDD (e.g., 61.7%) and no detectable curcumin. A significant contributory factor for the cytotoxicity of CA likely includes LDD; however, synergy with other constituents is possible.

Tumor cells must invade through the basal membrane and into blood vessels (intravasation) in order to migrate from a primary tumor mass to distant locations, circulate in the blood stream, survive during transport, then migrate out of a blood vessel (extravasation) to establish micrometastases. The penetration of circulating tumor cells into the endothelium is a crucial step for tumor metastasis. CA treatment of glioblastoma cells has significantly inhibited the cell migration in a dose-dependent manner. Cell migration is one of the pre-requisites of metastasis and glioblastomas are one of the highly metastatic malignancies in humans. The fact that CA can significantly inhibit cell migration and possibly metastasis, is supportive of its utility as a chemotherapeutic agent for glioblastomas. The effect of CA treatment was observed on other molecular targets. While Bax, p21 and caspase-3 proteins were upregulated by CA treatment, HSP90, mutant p53, Bcl-2, Bcl-X, BNIP3, VEGF and AMPKα were down regulated. CA treatment was observed to upregulate pro-apoptotic genes such as Bax, p21 and caspase-3 leading to apoptosis. P21 is a cdk (cyclin dependent kinase) inhibitor that is usually expressed in the $G_0/G_1$ phase of the cell cycle traverse and has been shown to inhibit a wide range of cdk/cyclin complexes, which are involved in the phosphorylation of Rb protein necessary for the progression from G1 to S phase. Therefore, up-regulation of p21 protein with CA treatment will adversely affect the $G_1$ to S phase progression. Similarly, since mutant p53 in U-87MG cells has been associated with chemoresistance, its down regulation by CA would render the cells susceptible to apoptosis and inhibit proliferation. The effect of CA treatment of tumor cells on multiple targets such as AKT, p21, p53, caspase-3, VEGF, HSP90 and AMPKα appears to contribute to the inhibition of tumor cell division, growth and migration and ultimately would be highly advantageous for direct or adjuvant therapeutic applications for cancer treatment. Several reports indicate that the inhibition of HSP90 would also be an effective anticancer strategy; therefore, CA inhibition of HSP90 protein would be an additional attribute. In summary, these results indicate the anticancer action of CA, targeting multiple targets in glioblastoma cells, supports a novel therapeutic approach for cancer patients.

Methods for CA Production

One aspect of the invention concerns a method for producing a carbon dioxide extract of *Curcuma amada*, comprising subjecting the *C. amada* plant material to carbon dioxide extraction, such as liquid carbon dioxide extraction or supercritical carbon dioxide extraction. In the case of liquid carbon dioxide extraction, the extraction is conducted at a temperature below the critical temperature of carbon dioxide, which is 31° C. (304.1K).

In some embodiments, the carbon dioxide extract of *C. amada* is produced with no more than 10% ethanol (0% to 10%) as a co-solvent. In some embodiments, the carbon dioxide extract is not the product of ethanol co-extraction (i.e., is produced with zero percent (0%) of ethanol as a co-solvent). In some embodiments, the method includes no co-solvent extraction. In some embodiments, the method does not include boiling (such as boiling the extract in solvent with or without subsequent evaporation of the solution to dryness or steam distillation). In some embodiments, the method includes no co-solvent extraction or boiling.

Figure 35A:
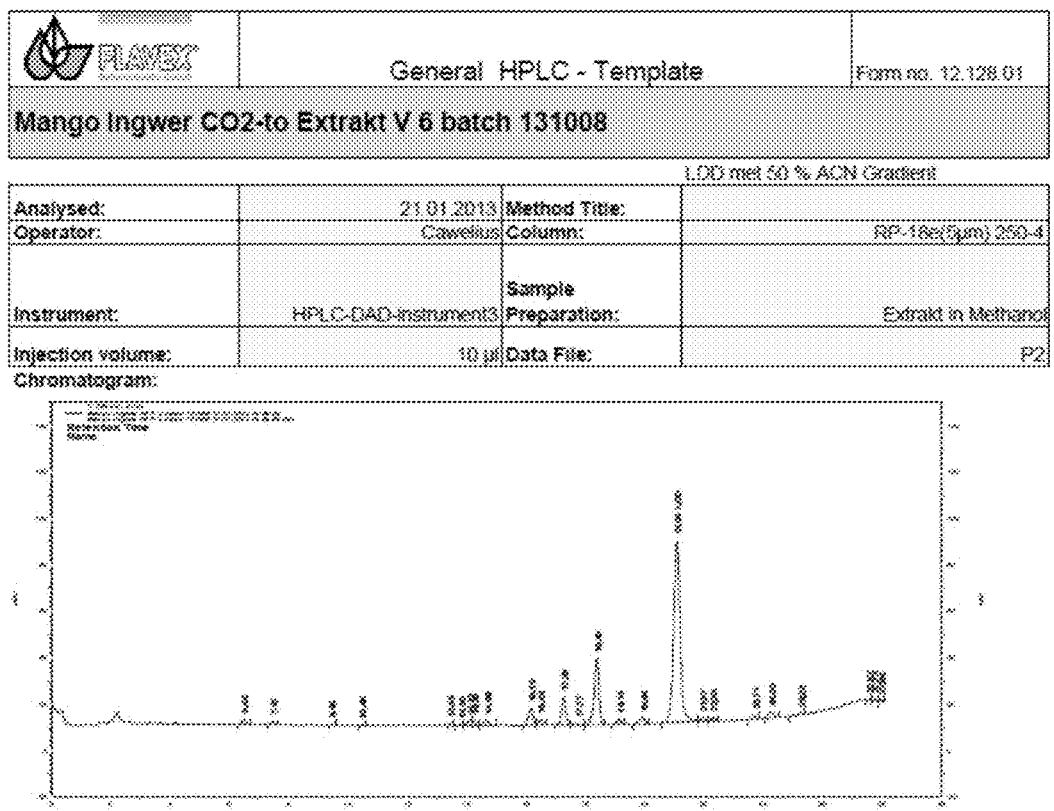
FIGS. 35A-35B: High-Performance Liquid Chromatography Analysis of CA extracted with supercritical carbon dioxide and ethanol extraction (FIG. 35A), and supercritical carbon dioxide extraction alone (FIG. 35B). The product from supercritical carbon dioxide+ethanol extraction has an (E)-Labda-8(17),12-diene-15,16-dial (LDD) concentration of 9.46%, whereas the product from supercritical carbon dioxide extraction has an LDD concentration of 61.67%.
Figure 35B:
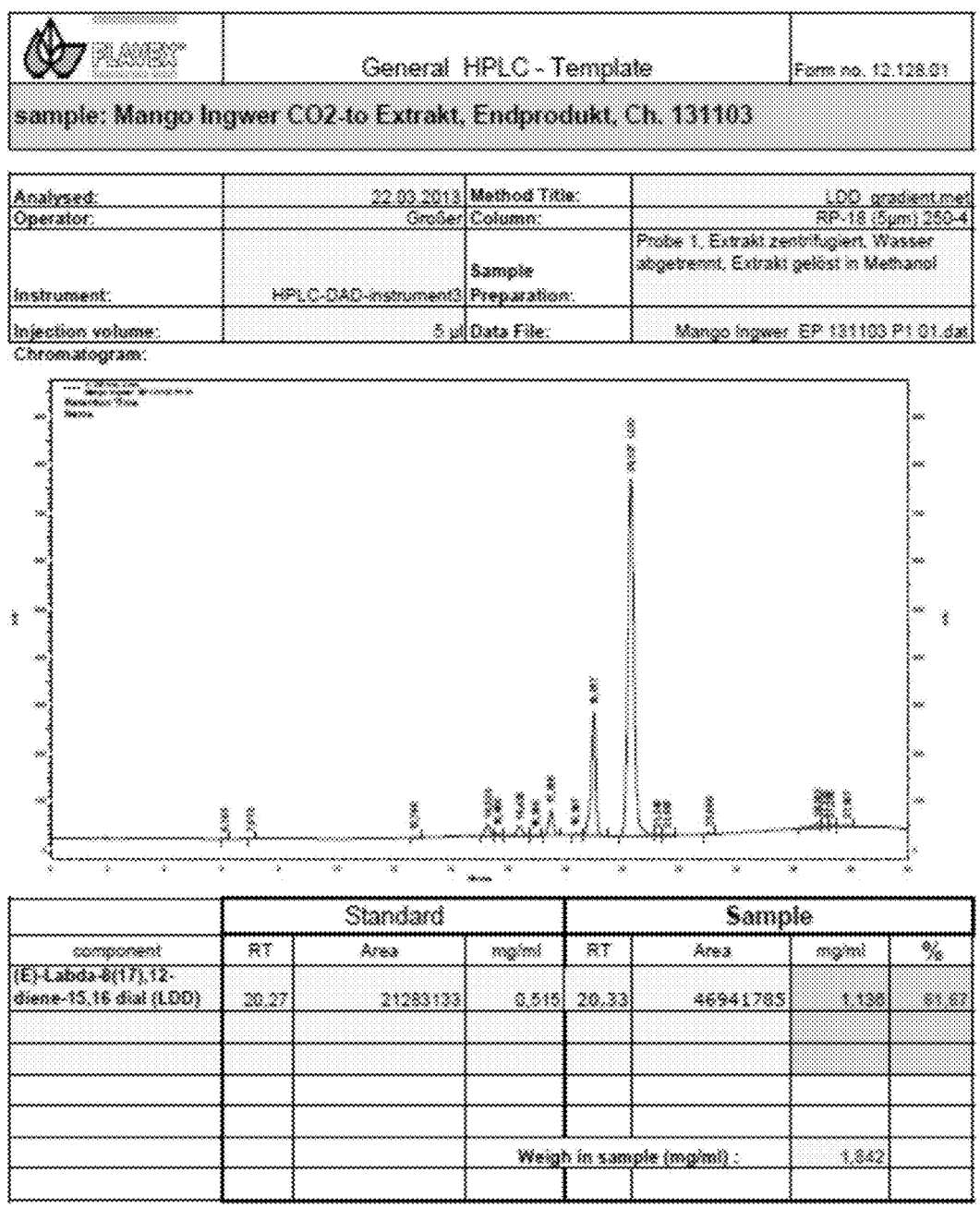

Initially, the inventors carried out supercritical carbon dioxide extraction with ethanol co-extraction as one extraction step, with ethanol acting as a co-solvent or entrainer for the carbon dioxide. It was thought that a more complete extract could be achieved by making the carbon dioxide more polar by ethanol addition. Subsequently, the inventors determined that LDD is an important constituent contributing to extract activity, but is sensitive to removal of ethanol from the co-solvent extract, which decomposes LDD to a major extent. The inventors determined that LDD can be completely extracted from the plant material without co-solvent addition. This permits the direct production of a completely solvent-free extract under more gentle conditions than those of normal solvent extraction. As an example, when produced under similar conditions, CA extracted with supercritical carbon dioxide and ethanol extraction had an LDD concentration of 9.46% after the ethanol had been removed by distillation, whereas supercritical carbon dioxide extraction alone had an LDD concentration of 61.67%, as shown by the results of high-performance liquid chromatography (HPLC) analysis in FIGS. 35A and 35B, respectively. That being said, to the extent *C. amada* is extracted with carbon dioxide and a small amount of ethanol is used as a co-solvent, if the ethanol is not removed, the alcohol solution (tincture) may be a suitable product as well. Therefore, in some embodiments, the carbon dioxide extract of *C. amada* is produced with no more than 10% ethanol as a co-solvent. In some embodiments, the carbon dioxide extraction is done with no ethanol co-extraction (i.e., is produced with zero percent (0%) of ethanol as a co-solvent).

In another example, 18-25 kg of dried *C. amada* root yielded 1 kg of product (brown, paste extract having mango-like odor). A summary of the Certificate of Analysis is shown in Table 7. The lower LDD content (53.2%), compared to 61.67% mentioned above (FIG. 35B), is reflective of a 20-month storage period at a refrigerated temperature.

While there are other components in the carbon dioxide *C. amada* extracts of the invention that are recognized to be bioactive, part of the uniqueness of the extracts of the invention, relative to the pre-extraction form of *C. amada*, lies in the capability to obtain a high yield of LDD and its preservation over long periods of time. In the natural, pre-extraction state, LDD is quite labile and unless it is processed within a relatively short time (probably weeks to a few months after harvesting), LDD degrades and will not be present in substantial quantities. Furthermore, products based on creating *C. amada* powders or other forms will suffer the same problem, LDD will degrade and thus such products will be substantially different. The carbon dioxide extracts of the invention are clearly different in terms of composition/structure than the pre-extraction material or other types of extracts since the relative chemical milieu is not preserved. Consequently, it is also logical that the biological activities are impacted.

Advantageously, conducting pure carbon dioxide supercritical extraction permits extraction and high yield of the LDD component within the extract without the need for further processing such as boiling in organic solvents such as methanol, acetone, ethylacetate, hexane, etc. The extracts used in Examples 1-15 were prepared using this supercritical carbon dioxide extraction process, i.e., without the use of ethanol as a co-solvent, and without further processing such as boiling in solvents.

The principle, methods, hardware, and application of supercritical extraction are described in Stahl et al. 1988, which is incorporated herein by reference in its entirety. In the case of *C. amada*, it is the ideal method because the active constituents are soluble, including LDD. The gentle supercritical carbon dioxide extraction process permits the maximum amount of LDD to be transferred from the plant material into the extract. Carbon dioxide is a lipophilic solvent, which means that other polar, diluting, or potentially interfering components are left behind and not incorporated into the extract. Thus, the supercritical carbon dioxide extract of *C. amada* is a concentrated and synergistic fraction of the most effective constituents without loss of LDD.

Accordingly, an aspect of the invention concerns a method for producing a carbon dioxide extract of *Curcuma amada*, comprising subjecting *C. amada* material to carbon dioxide extraction, resulting in an extract. In some embodiments, the carbon dioxide extraction is supercritical carbon dioxide extraction or liquid carbon dioxide extraction resulting in a supercritical carbon dioxide or liquid carbon dioxide extract of *C. amada*. In some embodiments of the production method, the carbon dioxide extraction (e.g., supercritical $CO_2$ or liquid $CO_2$ extraction) of *C. amada* is carried out using no more than 10% ethanol as a co-solvent. In some embodiments, the carbon dioxide extraction is carried out without using ethanol co-extraction (i.e., is produced with zero percent (0%) of ethanol as a co-solvent). In some embodiments, the method includes no co-solvent extraction. In some embodiments, the method does not include boiling (such as boiling the supercritical extract in solvent with or without subsequent evaporation of the solution to dryness or steam distillation). In some embodiments, the method includes no co-solvent extraction or boiling.

Various parts of the *C. amada* plant may be used as the starting material for the extraction. Appropriate methods for harvesting, cleaning, cutting, drying, and storage are known in the art. In some embodiments, the rhizome is used. After digging out and washing the rhizome, it can be cut and sliced to facilitate drying. Next, the *C. amada* material is conditioned by cutting and milling the material into a powder, typically having a particle distribution of about 0.2 to about 0.6 millimeters. This powder is used for one single extraction step. Extract work-up involves mainly water separation, which is achieved by warming and centrifugation.

The main parameters for carbon dioxide extraction are temperature and pressure. Because temperature can be harmful to sensitive botanical constituents, whereas the pressure determines gas density and solvent power, temperature is the more important parameter. In general, for *C. amada*, the temperature should not exceed about 60° C., and if liquid carbon dioxide is used a reasonable temperature interval is, for example, about 10° C. to about 30° C.; if supercritical carbon dioxide is used, a reasonable temperature interval is, for example, about 31° C. to about 60° C. A suitable pressure interval in the case of liquid carbon dioxide is, for example, from about 70 bar to about 200 bar, and in the case of supercritical carbon dioxide, from about 150 bar to about 700 bar. Higher pressure translates to higher solubility and faster extraction; however, if the relative solvent to plant material ratio is increased, the lower pressure will give a similar result. In some embodiments, the conditions for supercritical carbon dioxide extraction are 300 bar, 50° C., and 30 kg $CO_2$/kg dried and powdered *C. amada* root material. Extract separation methods are known in the art. Extract separation may be carried out, for example, at 60 bar and 30° C. The complete supercritical extract may be used in the methods of the invention, as was used in Examples 1-15 herein, or extract fractions enriched in a component such as LDD may be used.

In some embodiments, the carbon dioxide extract comprises at least about 5% LDD. In some embodiments, the extract comprises at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, or 61% LDD, or an incremental percentage between these percentages. In some embodiments, the carbon dioxide extract comprises α-pinene, camphene, β-pinene, β-myrcene, limonene, β-phellandrene, β-cariophyllene, ar-curcumene, α-zingiberene, and LDD.

The primary carbon dioxide extract is relatively stiff and sticky. Therefore, the extract may be combined with one or more natural or synthetic oils. This makes the product more liquid, facilitates water separation, and allows standardization for a more defined and consistent LDD content, e.g., X %±2%.

In some embodiments, the oil comprises one or more medium chain triglycerides. In some embodiments, the oil comprises medium chain fatty acids (e.g., C7, C8, or C10) or normal chain fatty acids (e.g., C16 or C18). In some embodiments, the oil comprises triheptanoin.

The oil can be any single oil or any combination of oils that is pharmaceutically acceptable. In some embodiments, the pharmaceutically acceptable oil comprises an oil selected from the group consisting of an animal oil, a fish oil, a vegetable oil, or a mineral oil. In some embodiments, the pharmaceutically acceptable oil comprises an edible oil. In some embodiments, the pharmaceutically acceptable oil is selected from the group consisting of olive oil, chia seed oil, soy germ oil, pomegranate oil, sunflower oil, sesame oil, almond oil, corn oil, orange oil, lime oil, black pepper oil, nutmeg oil, basil oil, rosemary oil, clove oil, grapefruit oil, fennel oil, coriander oil, bergamot oil, cinnamon oil, lemon oil, peppermint oil, garlic oil, thyme oil, marjoram oil, lemongrass oil, ginger oil, cardamon oil, liquid paraffin, cotton seed oil, peanut oil, nut oil, rapeseed oil, vitamin E oil and derivatives thereof, including Vitamin E TPGS (d-alpha tocopheryl polyethylene glycol 1000 succinate), fish oil, seafood oil, tallow-derived oil, silicone oil, castor oil, squalene oil, or any mixture thereof.

A range of other agents or additives may be included to provide additional control over a desired property, therapeutic effect, cosmetic appeal, or aid in compliance for a recommended use. A desirable therapeutic effect can include, for example, increasing bioavailability of the extract through topical use or consumption, providing additional therapeutic effect through addition of one or more agents, and the like. A cosmetic appeal can include, for example, providing the extract as a cream or lotion, adjusting the oiliness of a composition, adding a pleasing scent or moisturizer, and the like. Aiding in compliance can include, for example, adjusting the dosage to be in a form that facilitates compliance of patients by offering a small dosage form for consumption by concentrating the extract or, perhaps, offering a time-delay dosage form to reduce the frequency of patient intake that is desired to achieve a particular therapeutic effect.

In some embodiments, one or more of the following agents is included in the composition: a botanical extract, mineral, vitamin, nutrient, nutraceutical, dietary supplement, or active pharmaceutical ingredient. In some embodiments, the active pharmaceutical ingredient is one or more anti-cancer agents, such as those in Table 2. In some embodiments, the anti-cancer agent is one or more chemotherapeutic agents. In some embodiments, the botanical extract is selected from among a sterol, sterone, steroid, polyphenol, flavonoid, terpenoid, alkaloid, or a polysaccharide. In some embodiments, one or more antioxidants are included in the composition.

In some embodiments, the extract or composition is stable. In some embodiments, the extract or composition is substantially stable. It is desirable for the extract and compositions containing the extract to remain stable, or at least substantially stable, until it is used or activated, and this can relate to a shelf-life, or a time between creation and administration of the extract or composition, or some combination thereof. In some embodiments, the extract or composition is stable, or substantially stable, when usable as intended within a reasonable amount of time, a time that is considered reasonable by one of skill for the applications taught herein. In some embodiments, the extract or composition is usable within a reasonable time from making the extract/composition to the administration of the extract/composition and, in some embodiments, the extract/composition has a reasonable commercial shelf-life. A reasonable shelf-life can be at least, for example, 6 months, 1 year, 18 months, 2 years, 3 years, or any time in-between in increments of about 1 month, in some embodiments. As indicated above, one or more antioxidants can be included in the compositions of the invention. In addition to their beneficial health effects in vivo, antioxidants may increase the stability of the extract, as some extract components, such as LDD, can degrade over longer storage periods.

The pH of the extract or compositions can be adjusted. For example, for topical uses, the pH of the extract or composition can be adjusted to that of the skin, for example. Since the pH of skin is approximately 4.2 to 5.5, depending on the individual and area of the body, the pH of a topical formulation can range from about 4 to about 6.5 in some embodiments, from about 4.3 to about 5.8 in some embodiments, from about 4.5 to about 5.5 in some embodiments, or any range therein. In some embodiments, the pH can be 3.8, 4.0, 4.2, 4.4, 4.6, 4.8, 5.0, 5.2, 5.4, 5.6, 5.8, 6.0, 6.2, 6.4, 6.6, or any increment of about 0.1 therein.

Methods of Use

The extract of the invention, and by extension, compositions containing the extract, has potent anti-inflammatory properties as shown by suppression of COX-2 and NF-kB. However, data suggests there are other targets such as Akt, which is part of the PI3K-PTEN-Akt-mTOR pathway, a major inflammatory pathway and a prime target for cancer therapies. Without being limited by theory, the data shows that the extract targets both Akt and mTOR (directly or indirectly), which are downstream and thus may be a mechanism that is sensitizing tumors to other cancer therapies in addition to being a mechanism for direct action. These targets are in addition to COX-2, NF-kB and more downstream mechanisms such as Bax (activation) and Bcl-2 (inhibition) that drive cancer cells to apoptosis. Targeting of the two inflammatory pathways PI3K-PTEN-Akt-mTOR and Ras-Raf-MEK-ERK has implications beyond cancer therapy or anti-inflammatory therapy because there is evidence that targeting these pathways has beneficial effects on aging and diseases related to aging (Steelman et al. 2011; McCubrey et al. 2012; and Chappell et al. 2011). To a significant extent, this appears related to suppression of mTOR which is a counterpart to AMPK. In addition to evidence that the extract inhibits mTOR, the inventors have observed that there is mild AMPK phosphorylation by CA at lower concentrations. AMPK is not affected at higher concentrations. This bi-modal effect is commonly seen with many natural products.

Accordingly, an aspect of the invention concerns a method for inhibiting expression of Bcl-2, Bak, and p53 genes; inhibiting expression of the COX-2 and NF-kB genes; inhibiting production of phosphorylated target of rapamycin (TOR); modulating AMP-activated protein kinase (AMPK); inhibiting protein kinase B (AKT) signaling, modulating the Ras/Raf/MEK/ERK signaling pathway, and modulating the Ras/PI3K/PTEN/Akt/mTOR signaling pathway, wherein the method comprises contacting a target cell with an effective amount of an extract or composition of the invention in vitro or in vivo. The target cell may be a human or non-human cell, such as the cell of a subject. The term "contacting" encompasses bringing the extract or composition and the one or more target cells into contact by any method, regardless of whether the extract or composition is applied to the one or more cells, or the one or more cells are applied to the extract or composition, or a combination thereof.

Another aspect of the invention concerns a method for treating an existing condition as therapy, or preventing or delaying the onset of a condition as prophylaxis, in a subject, comprising administering an effective amount of an extract or composition of the invention to the subject. The subject may be a human or non-human animal subject.

The extracts and compositions of the invention may be administered by any conventional route including oral and parenteral. Examples of parenteral routes are subcutaneous, intradermal, transcutaneous, intravenous, intramuscular, intraorbital, intracapsular, intrathecal, intraspinal, intracisternal, intraperitoneal, etc. The compositions of the invention can be formulated for the most effective route of administration, including for example, oral, topical, transdermal, sublingual, buccal, parenteral, rectal, intranasal, intrabronchial or intrapulmonary administration. By way of example, the composition may be formulated as a microencapsulation, nanoencapsulation, microemulsion, nanoemulsion, liposomal preparation, capsule, tablet, sublingual form, quick-dissolve form, biofilm, oil solubilization, spray, or cosmeceutical preparation (e.g., cream, oil, or shampoo).

In some embodiments, the extract or composition is administered systemically (e.g., orally) or locally at the site of action. In some embodiments, the extract or composition is administered orally (e.g., ingested) or topically. In some embodiments, the extract or composition is administered parenterally. In some embodiments, the extract or composition is administered through a feeding tube.

In some embodiments, the methods comprise orally administering an effective amount of an oral dosage form of an extract or composition of the invention to a subject to systemically treat a condition such as those described herein. In some embodiments, the methods comprise orally administering an effective amount of an oral dosage form of an extract or composition described herein to a subject as a dietary supplement. In some embodiments, the methods comprise orally administering an effective amount of an oral dosage form of an extract or composition taught herein to a subject in combination with the topical administration.

Mango ginger extracts have been reported in the literature to have diverse pharmacological activities, including antimicrobial activity (against *E. coli, B. subtilis, S. aureus, B. cereus, Micrococcus leteus Listeria monocytogenes, E. fecalis, S. typhi, Klebsiella pneumonia, E. aerogenes*), antifungal activity (against *Curvularia palliscens, Aspergillus niger, A. terreus, Fusarium moniliforme*, and *F. falcatum*), hypotriglyceridemic activity, hypoglycemic activity, anti-hyperglycemic activity, antihelminthic activity, antioxidant activity, antiallergic activity, anti-inflammatory activity, platelet aggregation inhibitory activity, and cytotoxicity (Saman L R 2012, which is incorporated herein by reference in its entirety). The extracts, compositions, and methods of the invention may be used to treat a variety of conditions as therapy for an existing condition or prophylaxis (prevention or delay of onset) for a condition that is susceptible to treatment by administering an agent having one or more of the aforementioned activities. For example, by virtue of antioxidant and other activities, the extracts, compositions, and methods of the invention may be used to treat as therapy or prophylaxis (prevention or delay of onset) conditions associated with oxidative stress such as neurodegenerative diseases, cancer, stroke, and other pathologies (Firuzi O et al. 2011, which are incorporated herein by reference in their entirety).

The extracts of the invention and compositions containing them are useful for treatment of a variety of conditions as therapy for an existing condition or prophylaxis (prevention or delay of onset). In some embodiments, the condition to be treated is selected from the group consisting of a cell proliferation disorder (such as cancer), atherosclerosis (arteriosclerotic vascular disease), inflammation (acute inflammation or chronic inflammation), fever, infection (bacterial, mycobacterial, fungal, viral, or parasitic), hyperlipidemia, hypercholesterolemia, hypertriglyceridemia, hyperglycemia, platelet hyper-aggregation, aged and/or sun-damaged skin, autoimmune disorder, other immune disorders or neurodegenerative conditions (associated with a disease process or trauma).

The extracts, compositions, and methods of the invention may be used to treat a variety of infections as therapy for an existing infection or prophylaxis (prevention or delay of onset), such as bacterial infections (e.g., gram-positive, gram-negative, coccus, *bacillus, Rickettsia, mycoplasma*, spirillum), mycobacterial infections, fungal infections (e.g., opportunistic, primary, or localized fungal infections, such as aspergillosis, blastomycosis, candidiasis, coccidiodomycosis, cryptococcosis, histoplasmosis, mucormycosis, paracoccidiodomycosis, sporotrichosis), viral infections (e.g., bird flu, chickenpox, common cold, cytomegalovirus infection, Dengue, Ebola virus, Marburg virus, Hantavirus, hemorrhagic fever, herpes simplex virus, hervesvirus, infectious mononucleosis, influenza, Lassa fever, South American Hemorrhagic fevers, Middle East Respiratory Syndrome (MERS), polio, postherpetic neuralgia, severe acute respiratory syndrome (SARS), shingles, smallpox, H1N1 swine flu, yellow fever), and parasitic infections (e.g., African sleeping sickness, amebiasis, amebic infections due to free-living amebas, primary amebic mengoencephalitis, granulomatous amebic encephalitis, amebic ketatitis, ascariasis, babesiosis, Chagas Disease, cryptosporidiosis, dracunculiasis, filarial worm infection, dog heartworm infection, Loiasis, lymphatic filariasis, fluke infections, giardiasis, hookworm infection, leishmaniasis, malaria, microsporidiosis, onchocerciasis, pinworm infection, schistosomiasis, tapeworm infection, dog tapeworm infection, strongyloidiasis, toxocariasis, toxoplasmosis, trichinosis, whipworm infection). In some embodiments, the infection is a helminth infection.

The extracts, compositions, and methods of the invention may be used to treat various types of immune disorders as therapy or prophylaxis, such as transplant rejection (e.g., cell, tissue, or organ transplant; allograft, xenograft), allergic response, and autoimmune disorders.

An example of a condition representing both inflammation and an allergic response that may be treated with the extracts, compositions, and methods of the invention is allergic rhinitis. Rhinitis, which occurs most commonly as allergic rhinitis, is an inflammation of the nasal membranes that is characterized by sneezing, nasal congestion, nasal itching, and rhinorrhea, in any combination. In a trial of forty patients, the plant Amraganda harida (*Curcuma amada Roxb.*) appeared to be effective in reducing the signs and symptoms of allergic rhinitis (Bhaskaran A S et al. 2012, which is incorporated herein by reference in its entirety).

Further specific examples of immune disorders that may be treated include graft-versus-host disease, acute graft-versus-host disease, rheumatoid arthritis, psoriasis, Crohn's disease, inflammatory bowel disease, multiple sclerosis, Celiac Sprue, idiopathic thrombocytopenic thrombotic purpura, myasthenia gravis, Sjogren's syndrome, scleroderma, ulcerative colitis, asthma, uveitis, epidermal hyperplasia, cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, glomerular nephritis, or autoimmune hepatitis.

In some embodiments, the condition is aged and/or sun-damaged skin, and the extract or composition is administered orally, or topically on the aged or sun-damaged skin. The extract or composition can be administered as therapy to skin that is already aged or sun-damaged, or as a prophylaxis to prevent or delay onset of aging or sun damage (protecting it from initial damage or further damage).

In some embodiments, the method is a method of treating inflammation (acute or chronic) of a tissue of subject, the method comprising administering an effective amount of an extract or composition of the invention to the tissue of the subject. The tissue to which the extract or composition is administered may itself have inflammation and/or may be adjacent to tissue having inflammation. In some embodiments, the tissue is a wounded tissue (acute or chronic wound). In some embodiments, the tissue is not wounded. In some embodiments, for treatment of wounded tissue, the extract or composition is applied on and/or within a bandage or other wound dressing.

Any tissue that can make contact with one or more active components of an extract or composition (e.g., LDD) can be treated. The tissue can be, for example, connective, muscle, nervous, and/or epithelial tissue. In some embodiments, the tissue is a dermal tissue. In some embodiments, the tissue is a mucosal tissue. In some embodiments, the tissue is gastrointestinal tissue. In some embodiments, a first tissue makes contact with one or more active components of the extract or composition and a second tissue derives a benefit as a secondary effect.

In some embodiments, the condition is a cell proliferation disorder, such as cancer. Without being limited by theory, CA demonstrates substantial inhibition of ATP in cancer, implying a direct effect on cancer energy metabolism. As described in Example 15 and shown in FIG. 34, CA significantly inhibited ATP synthesis in U-87MG tumor cells. This suggests a potential therapeutic mechanism through the targeting of mitochondrial metabolism and the Warburg effect, which is a putative mechanism for most forms of cancer. Thus, the invention includes methods for treatment of cell proliferation disorders, as therapy or prophylaxis, such as cancer in a subject by administering an extract or composition of the invention to the subject, as well as methods for inhibiting the metabolism of cancer cells in vitro or in vivo by contacting the cells with an extract or composition of the invention in vitro or in vivo.

In some embodiments, the condition is a cell proliferation disorder, such as cancer, and the method further comprises administering a different treatment for the cell proliferation disorder. Examples of different treatments include chemotherapy, radiation therapy, immunotherapy, and/or surgery. The different treatment may be administered before, during, and/or after administration of the extract or composition.

In some embodiments, the condition is inflammation (local and/or systemic, acute or chronic) or disorders associated with inflammation, in the presence or absence of a cell proliferation disorder.

In some embodiments, the condition is an infection, such as a bacterial infection (e.g., gram-positive or gram-negative), mycobacterial infection, fungal infection, viral infection, or parasitic infection. The extract or composition may be administered systemically or locally at the site of an infection.

In some embodiments, the condition is systemic inflammation, and the extract or composition is administered orally or parenterally. In other embodiments, the condition is local inflammation, and the extract or composition is administered locally at the site of the inflammation, orally, or parenterally. In some embodiments, the condition is inflammation associated with a sore, wound (e.g., cut, bruise, burn) rash, dryness, or infection, and the extract or composition is topically administered to the subject.

In some embodiments, the condition is chronic inflammation (local and/or systemic), and the extract or composition is administered to the subject. Through CA's inhibitory effect on cyclooxygenase 1 (COX-1) and cyclooxygenase 2 (COX-2) activities, CA can ameliorate chronic inflammation, such as that which contributes to the development of some forms of cancer. The down-regulation of heat shock protein 90 (HSP-90) and human telomerase reverse transcriptase (shown in FIG. 33) may also contribute to the chemo-preventive properties of CA. In some embodiments, the chronic inflammation is systemic, chronic inflammation, and the extract or composition is administered orally or parenterally. In other embodiments, the chronic inflammation is localized, and the extract or composition is administered locally at the site of the chronic inflammation, orally, or parenterally In some embodiments, the cell proliferation disorder is a chemo-resistant or chemo-sensitive cancer. The extract or composition may be administered systemically or locally at the site(s) of the cancer. In some embodiments of the invention, the cell proliferation disorder is a cancer selected from leukemia, hepatic carcinoma, pancreatic cancer, colon cancer, glioblastoma, rhabdomyosarcoma, brain cancer, neuroblastoma, and breast cancer. In some embodiments of the invention, the cell proliferation disorder is selected from among cancer of the lung, breast, prostate, colon, ovary, gastrointestinal system (e.g., esophagus), head and neck, endometrium, and skin (melanoma). Other examples of cancer types that may be treated by administering the extracts or compositions of the invention include, but are not limited to, those in Table 1.

In some embodiments, the extract or composition is administered to a subject having cancer, as a monotherapy, or in combination with one or more anti-cancer treatments (e.g., a chemotherapeutic agent) administered before, during, or after administration of the extract or composition. If administered simultaneously, the additional anti-cancer agent(s) may be administered in the same composition as the extract or separately. In some embodiments, the extract or composition is in the form of a capsule administered orally (e.g., for oral consumption). In some embodiments, the extract is administered with water, oil (e.g., olive oil or other vegetable oil), or other carrier, orally or through injection.

In some embodiments, the condition is an autoimmune disorder, which are diseases caused by an immune response against the body's own cells or tissues. Autoimmune disorders result in destruction of one or more types of body tissues, abnormal growth of an organ or organs, or changes in organ function or functions. The disorders may affect only one organ or tissue type or may affect multiple organs and tissue types. In addition, a person may experience one or more autoimmune disorders at the same time. Organs and tissues commonly affected by autoimmune disorders include blood components such as red blood cells, blood vessels, connective tissues, endocrine glands such as the thyroid or pancreas, muscles, joints, and skin.

Examples of autoimmune disorders that may be treated include AIDS-associated myopathy, AIDS-associated neuropathy, Acute disseminated encephalomyelitis, Addison's Disease, Alopecia Areata, Anaphylaxis Reactions, Ankylosing Spondylitis, Antibody-related Neuropathies, Antiphospholipid Syndrome, Arthritis (e.g., rheumatoid arthritis, psoriatic arthritis, juvenile idiopathic arthritis), Autism, Autoimmune Atherosclerosis, Autoimmune Diabetes Insipidus, Autoimmune Endometriosis, Autoimmune Eye Diseases, Autoimmune Gastritis, Autoimmune Hemolytic Anemia, Autoimmune Hemophilia, Autoimmune Hepatitis, Autoimmune Interstitial Cystitis, Autoimmune Lymphoproliferative Syndrome, Autoimmune Myelopathy, Autoimmune Myocarditis, Autoimmune Neuropathies, Autoimmune Oophoritis, Autoimmune Orchitis, Autoimmune Thrombocytopenia, Autoimmune Thyroid Diseases, Autoimmune Urticaria, Autoimmune Uveitis, Autoimmune Vasculitis, Behcet's Disease, Bell's Palsy, Bullous Pemphigoid, CREST, Celiac Disease, Cerebellar degeneration (paraneoplastic), Chronic Fatigue Syndrome, Chronic Rhinosinusitis, Chronic inflammatory demyelinating polyneuropathy, Churg Strauss Syndrome, Connective Tissue Diseases, Crohn's Disease, Cutaneous Lupus, Dermatitis Herpetiformis, Dermatomyositis, Diabetes Mellitus, Discoid Lupus Erythematosus, Drug-induced Lupus, Endocrine Orbitopathy, Glomerulonephritis, Goodpasture Syndrome, Goodpasture's Syndrome, Graft-versus-Host Disease (GVHD), Graves Disease, Guillian-Barre Syndrome, Miller Fisher variant of the Guillian Barre Syndrome, axonal Guillian Barre Syndrome, demyelinating Guillian Barre Syndrome, Hashimoto Thyroiditis, Herpes Gestationis, Human T-cell lymphomavirus-associated myelopathy, Huntington's Disease, IgA Nephropathy, Immune Thrombocytopenic Purpura, Inclusion body myositis, Interstitial Cystitis, Isaacs syndrome, Lambert Eaton myasthenic syndrome, Limbic encephalitis, Lower motor neuron disease, Lyme Disease, MCTD, Microscopic Polyangiitis, Miller Fisher Syndrome, Mixed Connective Tissue Disease, Mononeuritis multiplex (vasculitis), Multiple Sclerosis (relapsing-remitting MS (RRMS), secondary-progressive MS (SPMS), primary-progressive MS (PPMS), and progressive-relapsing MS (PRMS)), Myasthenia Gravis, Myxedema, Meniere Disease, Neonatal LE, Neuropathies with dysproteinemias, Opsoclonus-myoclonus, PBC, POEMS syndrome, Paraneoplastic Autoimmune Syndromes, Pemphigus, Pemphigus Foliaceus, Pemphigus Vulgaris, Pernicious Anemia, Peyronie's Disease, Plaque Psoriasis, Plasmacytoma/myeloma neuropathy, Poly-Dermatomyositis, Polyarteritis Nodosa, Polyendocrine Deficiency Syndrome, Polyendocrine Deficiency Syndrome Type 1, Polyendocrine Deficiency Syndrome Type 2, Polyglandular Autoimmune Syndrome Type I, Polyglandular Autoimmune Syndrome Type II, Polyglandular Autoimmune Syndrome Type III, Polymyositis, Primary Biliary Cirrhosis, Primary Glomerulonephritis, Primary Sclerosing Cholangitis, Psoriasis, Psoriatic Arthritis, Rasmussen's Encephalitis, Raynaud's Disease, Relapsing Polychondritis, Retrobulbar neuritis, Rheumatic Diseases, Rheumatoid Arthritis, Scleroderma, Sensory neuropathies (paraneoplastic), Sjogren's Syndrome, Stiff-Person Syndrome, Subacute Thyroiditis, Subacute autonomic neuropathy, Sydenham Chorea, Sympathetic Ophthalmitis, Systemic Lupus Erythematosus, Transverse myelitis, Type 1 Diabetes, Ulcerative Colitis, Vasculitis, Vitiligo, Wegener's Granulomatosis, acrocyanosis, anaphylactic reaction, autoimmune inner ear disease, bilateral sensorineural hearing loss, cold agglutinin hemolytic anemia, cold-induced immune hemolytic anemia, idiopathic endolymphatic hydrops, idiopathic progressive bilateral sensorineural hearing loss, immune-mediated inner ear disease, and mixed autoimmune hemolysis.

The supercritical extract possesses properties making it useful for anti-inflammatory and anti-aging applications. A subtle increase of chronic inflammation level is a characteristic of skin aging. Inflammation is caused by activation of signal pathways such as nuclear factor kappaB (NF-KB) by various intrinsic (dysfunctions as a consequence of aging) and extrinsic (exposition to polluting chemicals, smoke, UV-radiation) impacts. A consequence is the release of inflammatory mediators such as pro-inflammatory cytokines, the expression of MMPs and the stimulation of cyclooxygenase enzymes (COX-2) which mediate the production of pro-inflammatory prostaglandins (PEG2). Inflammation is often affiliated with damaging free radicals and oxidative stress. In this regard, the extract and composition of the invention can make a positive impact as well.

Another aspect of the extract is its ability to modulate AMPK-activated protein kinase (AMPK), which up-regulates cellular energy production by phosphorylation of key enzymes in metabolic pathways. Normally, AMPK activation is achieved by exercise and physical training. The skin is the largest human organ. The metabolically active deeper skin layers are responsible for ongoing skin regeneration and for hair growth functionality. With advancing age and impaired signal transduction pathways, a slow-down of mitochondrial function and accordingly energy metabolism is observed. This process is considered a key factor in the modern theory of skin aging. Such conditions highly benefit from AMPK activation, which plays a major role in boosting cellular energy and improving the overall energy balance by enhancing mitochondrial activity and capacity. AMPK stimulation influences a whole cascade of processes upstream and downstream. In particular, it switches on catabolic pathways which generate adenosine-5'-triphosphate (ATP) and switches off ATP consuming actions on a cellular level and beyond. Therefore, the extract and composition of the invention may be used as an effective anti-aging agent for the skin due to its AMPK activity, and may be applied topically to aged and/or sun-damaged skin. A rejuvenating effect would be expected from its anti-oxidative and anti-inflammatory properties (e.g., inhibition of the pro-inflammatory cytokine TNF-alpha, COX-2, and NF-kB).

With increasing longevity and the numbers of people in the 40+ generation, cosmetic ingredients providing anti-aging benefits are a big trend. Looking good strengthens one's self-esteem, improves the quality of life and social integration. Another emerging trend is natural ingredients which are conforming to the different standards that have been established today. The extract and compositions of the invention fulfill these requirements and may be used for the creation of cosmetic products that inhibit photo-aging, act against degenerative skin conditions and restore a healthy skin function.

Anti-aging also refers to longevity in general. Thus, in some embodiments the extract or composition may be administered to a subject to target mechanisms or metabolic pathways associated with enhanced longevity. These include mechanisms such as hormesis, an important biological adaptive response by cells and organisms to stress that improves the organism's defense mechanisms such as chaperone-mediated stress response pathways (uncoupled protein response, autophagy, mitochondrial biogenesis, etc.), energy metabolism stress response pathways (AMPK and mTOR), oxidative/genotoxic stress response pathways (redox, NF-kB, p53, sestrins, Nrf-2) and system response pathways (immune, inflammation and neuroendocrine responses) and metabolic pathways attributed to enhancement of longevity including modulation of AMPK, mTOR, NAD+, sirtuins, FOXO, PGC-1α and PPAR's. For example, the extract's anti-aging properties are in part attributed to inhibition or reduction of mTOR activity (see FIGS. 32 and 33), and may be utilized by administering the extract or composition to cells in vitro or to a subject in vivo to increase longevity of the cells and subject, and treat, prevent, or delay the onset of age-associated diseases such as atherosclerosis, cardiovascular disease, cancer, arthritis, cataracts, osteoporosis, type 2 diabetes, hypertension, and Alzheimer's disease in subject.

The optimal formulations for the extracts and compositions of the invention can be readily determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

In some embodiments, the extract or composition is used with one or more additional agents. For example, the additional agents may have an activity useful for treating the condition independently, and/or have an activity that enhances the effect of the extract or composition of the invention. The additional agents may be administered to a subject or brought into contact with cells in vitro or in vivo simultaneously, or consecutively (sequentially) in any order relative to the extract of the invention. If administered to a subject or brought into contact with cells, the extract of the invention and the one or more additional agents may be administered or brought in contact with cells separately in separate formulations, or together within one formulation (one composition). Some combinations may be a synergistic effect relative to the effects or properties of extract or compositions of the invention and the one or more additional agents. If administered in different formulations, the composition and the additional agent(s) can be administered by the same route or by different routes, before, during, and/or after administration of the composition of the invention. Examples of the agents that may be used in combination with the extracts and compositions of the invention include but are not limited to drugs and biologics such as anti-cancer agents, oils such as medium chain triglycerides, and extracts. In some embodiments, the agent is an aqueous or organic solvent extract. In some embodiments, the extract used as an additional agent is a supercritical $CO_2$ extract or ethanolic extract. In some embodiments, the extract is a $CO_2$ and/or ethanolic extract of hops, Schisandra species (*chinensis* and *spherandra*), supercritical $CO_2$ extract of gromwell root, supercritical $CO_2$ and/or ethanolic extract of *Tinospora cordifolia* supercritical $CO_2$ and/or ethanolic extract of C. long (turmeric), or supercritical $CO_2$ and/or ethanolic extract of *C. xanthorhizza*. Other specific examples of agents that may be used in combination with the extract and compositions include irinotecan (IR), cyclophosphamide (CP), vinoblastine (VBL), temozolamide (TEM), etoposide (ETO), and curcumin.

Depending on the intended mode of administration, the compositions used in the methods described herein may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. Each dose may include an effective amount of a composition used in the methods described herein in combination with a pharmaceutically acceptable carrier and, in addition, may include other medicinal agents, pharmaceutical agents, carriers, adjuvants, diluents, etc. An effective dose in vitro or in vivo will be appropriate for the desired effect (e.g., treating a condition (e.g., a cell proliferation disorder such as cancer), inhibiting expression of Bcl-2, Bak, and p53 genes, inhibiting expression of the COX-2 and NF-kB genes, inhibiting production of phosphorylated target of rapamycin (TOR), modulating AMP-activated protein kinase (AMPK), inhibiting protein kinase B (AKT) signaling, modulating the Ras/Raf/MEK/ERK signaling pathway, and modulating the Ras/PI3K/PTEN/Akt/mTOR signaling pathway). For example, in some embodiments, 500 mg of the composition is orally administered to a subject once or twice per day. The percentage of active ingredients in cosmeceutical formulations tends to be in the range of 0.1%-2.0%. In one embodiment, the extract or composition inhibits or reduces mTOR activity in vivo and promotes or enhances (increases) longevity in the subject to which the extract or composition is administered.

The percentage of active ingredients in the compositions of the invention can be tailored to the desired application. For example, excipients and other agents may be added to reduce the concentration of a desired active ingredient. In some embodiments, an oil, such as vegetable oil, is included in the composition.

Liquid pharmaceutically administrable compositions can be prepared, for example, by combining a composition described herein with an excipient, such as, for example, water, saline aqueous dextrose, glycerol, ethanol, and the like, to thereby form a solution or suspension. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. If desired, the composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; see, for example, Remington's Pharmaceutical Sciences, 18th Ed. (1990), Mack Publishing Co., Easton, Pa., the entire disclosure of which is hereby incorporated by reference).

Formulations comprising compositions described herein may be presented in unit-dose or multi-dose containers, for example sealed ampoules and vials, and may be stored in a freeze dried (lyophilized) condition requiring only the condition of the sterile liquid carrier, for example, water, prior to use. Extemporaneous injection solutions and suspensions may also be prepared from sterile powder, granules, tablets, etc. It should be understood that in addition to the ingredients particularly mentioned above, the formulations of the subject invention can include other agents conventional in the art having regard to the type of formulation in question.

One of skill understands that the amount of the agents administered can vary according to factors such as, for example, the type of disease, age, sex, and weight of the subject, as well as the method of administration. Dosage regimens may also be adjusted to optimize a therapeutic response. In some embodiments, a single bolus may be administered; several divided doses may be administered over time; the dose may be proportionally reduced or increased; or, any combination thereof, as indicated by the exigencies of the therapeutic situation and factors known to one of skill in the art. It is to be noted that dosage values may vary with the severity of the condition to be alleviated, as well as whether the administration is prophylactic, such that the condition has not actually onset or produced symptoms. Dosage regimens may be adjusted over time according to the individual need and the professional judgment of the person administering or supervising the administration of the compositions, and any dosage ranges set forth herein are exemplary only and do not limit the dosage ranges that may be selected.

As indicated above, the invention includes a method for treating an infection of a subject, such as a bacterial infection or fungal infection by administering an effective amount of an extract or composition described herein. The extract or composition may be administered systemically or locally at the site of an infection. An ethanol extract of *Curcuma amada* was found to have antifungal activity and broad spectrum of antibacterial activity against several strains (Policegoudra et al. 2011).

Another aspect of the invention concerns a method for inhibiting contamination, comprising applying (contacting) an effective amount of the extract or composition described herein to a surface (i.e., a substrate) to inhibit contamination of the surface by a microbe, such as gram-positive or gram-negative bacteria, or fungus. The term "applying" is intended broadly in this context, and is inclusive of applying the extract or composition as a coating, or injecting or otherwise impregnating the extract or composition into a surface. The extract or composition may be brought into contact with the surface to be treated in a conventional way, such as by preparing a solution that is then brought into contact with the surface, or dipping the surface into the solution. The extract or composition may be applied to the surface as a spray or mist, brushed on the surface, wiped on the surface, injected into the surface, and so forth. The term "applying" encompasses bringing the extract or composition and the surface into contact by any method, regardless of whether the extract or composition is applied to the surface, or the surface is applied to the extract or composition, or a combination thereof.

Virtually any surface—animal, mineral, or vegetable (biotic or abiotic) that may be vulnerable to contamination is suitable for the method of the invention. The surface may be solid, semi-solid, or liquid. The extract or composition may be applied as a disinfectant or as a food preservative to control the growth of food-borne pathogens. For example, the surface may be objects in a commercial or residential setting, particularly in a healthcare or research setting in which infection is a concern. The surface may be a medical or dental device or implant, such as orthopedic implants or prosthetics, stents, devices for transport of biological fluid or waste, surgical implement such as knives, saws, scalpels, etc. The surface may be that of a garment such as a hospital gown, or a surgical drape. The surface may be that of an object that contacts a human or animal body or is placed within the human or animal body. The surface may be a sterile surface, or non-sterile surface. The surface may be one used for fluid storage or fluid delivery In some embodiments, the surface is biological tissue, and is applied in vitro or in vivo. In some embodiments, the surface is metal, plastic, ceramic, glass, or cloth. In some embodiments, the surface is a food or beverage. In some embodiments, the surface is a natural or synthetic fibrous or woven material. In some embodiments, the surface is a swab, cloth, wipe, or mop, which may then be applied to another surface. In some embodiments, the surface is an outer surface or inner surface of a container, such as a jar, bottle, bag, or canister.

In addition to the other agents disclosed herein, the extract or composition may be combined with other agents useful in antimicrobial compositions, such as one or more other antimicrobial compounds, coloring agents, scent additives, etc.

Articles of Manufacture

Another aspect of the invention concerns kits that encompass finished, packaged and labelled products. These are articles of manufacture that can include the appropriate unit dosage form of the extract or composition in an appropriate vessel or container such as, for example, a glass or plastic vial or other container that is sealed (e.g., hermetically sealed). In some embodiments, the dosage form is suitable for oral administration, topical administration, or both. In some embodiments, the dosage form is suitable for intravenous administration or another parenteral route disclosed herein.

As with any such product, the packaging material and container(s) are designed to protect the stability of the product during storage and shipment. In addition, the kit can include instructions for use or other information material that can advise the user such as, for example, a physician, technician or patient, how to properly administer or apply the extract or composition to a subject or surface. In some embodiments, instructions can indicate or suggest an amount or dosing regimen that includes, but is not limited to, actual doses and monitoring procedures. The kits can include one or more containers containing one or more additional agents for carrying out the methods described herein.

In some embodiments, the instructions can include informational material indicating how to apply or administer an extract or composition for a particular use or range of uses, such as treatment of a particular condition disclosed herein or for inhibiting contamination. Instructions and other informational material can be provided on various media (e.g., printed on paper, digital media, etc.).

In some embodiments, kits that contain a combination of different dosage forms for administrations to a subject are also provided, as well as instructions for use, as the kits can be designed for physicians, patients, or over the counter use by any subject. In some embodiments, the kit is for treatment as therapy or prophylaxis of a cell proliferation disorder (such as cancer), atherosclerosis (arteriosclerotic vascular disease), inflammation, fever, infection (bacterial, mycobacterial, fungal, viral, or parasitic), hyperlipidemia, hypercholesterolemia, hypertriglyceridemia, hyperglycemia, platelet hyper-aggregation, aged and/or sun-damaged skin, autoimmune disorder, other immune disorders or neurodegenerative conditions (associated with a disease process or trauma).

The kits can include instructions for mixing the extract or composition with additional agents, prior to administration to a subject or application to a surface, suggested dilution factors for various target sites, and potential combination therapies for combined administrations, such as topical combined with oral administration. The suggested dilution factors can be selected based on the desired administration ranges suitable for the subject to be treated or concentrations appropriate for the surface for contamination inhibition, for example, which can be modified in some embodiments as desired, and incorporated into the compositions.

EXEMPLIFIED EMBODIMENTS

Embodiment 1

A carbon dioxide extract of *Curcuma Amada*.

Embodiment 2

The extract of embodiment 1, wherein the extract is a supercritical carbon dioxide extract or liquid carbon dioxide extract of *C. amada*.

Embodiment 3

The extract of embodiment 1 or 2, wherein the extract and is produced with no more than 10% of ethanol as a co-solvent.

Embodiment 4

The extract of any one of embodiments 1 to 3, wherein the extract is not the product of ethanol co-extraction (i.e., is produced with 0% of ethanol as a co-solvent).

Embodiment 5

The extract of any one of embodiments 1 to 4, wherein the extract comprises at least about 5% (E)-Labda-8(17),12-diene-15,16-dial (LDD).

Embodiment 6

The extract of any one of embodiments 1 to 5, wherein the extract comprises at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, or 61% (E)-Labda-8(17),12-diene-15,16-dial (LDD), or an incremental percentage there between.

Embodiment 7

The extract of embodiment any one of embodiments 1 to 6, wherein the extract comprises α-pinene, camphene, β-pinene, β-myrcene, limonene, β-phellandrene, 3-cariophyllene, ar-curcumene, α-zingiberene, and (E)-Labda-8(17),12-diene-15,16-dial (LDD).

Embodiment 8

A composition comprising the carbon dioxide extract of any one of embodiments 1 to 7; and a carrier or excipient.

Embodiment 9

The composition of embodiment 8, further comprising a natural or synthetic oil.

Embodiment 10

The composition of embodiment 9, wherein the natural or synthetic oil comprises one or more medium chain triglycerides.

Embodiment 11

The composition of embodiment 9, wherein the natural or synthetic oil comprises medium chain fatty acids (e.g., C7, C8, or C10) or normal chain fatty acids (e.g., C16 or C18).

Embodiment 12

The composition of embodiment 9, wherein the natural or synthetic oil comprises triheptanoin.

Embodiment 13

The composition of embodiment 9, wherein the natural or synthetic oil comprises a vegetable oil.

Embodiment 14

The composition of embodiment 8, wherein the natural or synthetic oil comprises at least one natural oil selected from among olive oil, chia seed oil, soy germ oil, pomegranate oil, fish oil, and seafood oil.

Embodiment 15

The composition of embodiment 8, further comprising an agent selected from among a botanical extract, mineral, vitamin, nutrient, other nutraceutical, dietary supplement, or active pharmaceutical ingredient.

Embodiment 16

The composition of embodiment 15, wherein the composition further comprises the active pharmaceutical ingredient, and wherein the active pharmaceutical ingredient is one or more chemotherapeutic agents.

Embodiment 17

The composition of embodiment 8, further comprising a botanical extract selected from among a sterol, sterone, steroid, polyphenol, flavonoid, terpenoid, alkaloid, or a polysaccharide.

Embodiment 18

The composition of embodiment 8, further comprising an antioxidant.

Embodiment 19

The composition of embodiment 8, wherein the composition is an oral formulation.

Embodiment 20

The composition of embodiment 8, wherein the composition is a topical formulation.

Embodiment 21

The composition of embodiment 8, wherein the composition is a liquid.

Embodiment 22

The composition of embodiment 8, wherein the composition is a powder.

Embodiment 23

The composition of embodiment 8, wherein the composition is formulated as a microencapsulation, nanoencapsulation, microemulsion, nanoemulsion, liposomal preparation, capsule, tablet, sublingual form, quick-dissolve form, biofilm, oil solubilization, spray, or cosmeceutical preparation.

Embodiment 24

A method for treating or delaying the onset of a condition in a subject, comprising administering an effective amount of an extract or composition of any one of embodiments 1 to 23 to the subject.

Embodiment 25

The method of embodiment 24, wherein the condition is selected from the group consisting of a cell proliferation disorder, inflammation, fever, infection, hyperlipidemia, hypercholesterolemia, hypertriglyceridemia, hyperglycemia, platelet hyper-aggregation, immune disorder (for example, an autoimmune disorder), neurodegenerative condition (associated with a disease process or trauma).

Embodiment 26

The method of embodiment 25, wherein the condition is a cell proliferation disorder, and wherein the cell proliferation disorder is cancer or atherosclerosis (arteriosclerotic vascular disease).

Embodiment 27

The method of embodiment 26, wherein the condition is a chemo-resistant cancer.

Embodiment 28

The method of embodiment 25, wherein the condition is a cell proliferation disorder, and wherein the method further comprises administering a different treatment for the cell proliferation disorder before, during, and/or after administration of the extract or composition.

Embodiment 29

The method of embodiment 28, wherein the cell proliferation disorder is a cancer, and wherein the different treatment comprises administration of a chemotherapeutic agent, radiation therapy, immunotherapy, and/or surgery.

Embodiment 30

The method of embodiment 24, wherein the condition is inflammation or associated with inflammation, and wherein the subject has a cell proliferation disorder.

Embodiment 31

The method of embodiment 24, wherein the condition is inflammation or associated with inflammation, and wherein the subject does not have a cell proliferation disorder.

Embodiment 32

The method of embodiment 24, wherein the condition is chronic inflammation or associated with chronic inflammation.

Embodiment 33

The method of embodiment 24, wherein the condition is an infection, and wherein the infection is a bacterial infection, mycobacterial infection, fungal infection, viral infection, or parasitic infection.

Embodiment 34

The method of embodiment 24, wherein the condition is allergic rhinitis.

Embodiment 35

The method of embodiment 24 or 25, wherein the extract or composition is administered orally or topically.

Embodiment 36

The method of embodiment 24 or 25, wherein the extract or composition is administered parenterally.

Embodiment 37

The method of embodiment 24 or 25, wherein the extract or composition is administered through a feeding tube.

Embodiment 38

The method of embodiment 24, wherein the condition is systemic inflammation, and wherein the extract or composition is administered orally or parenterally.

Embodiment 39

The method of embodiment 24, wherein the condition is local inflammation, and wherein the extract or composition is administered locally at the site of the inflammation, orally, or parenterally.

Embodiment 40

The method of embodiment 24, wherein the condition is inflammation associated with a sore, wound (e.g., cut, bruise, burn) rash, dryness, or infection, and wherein the extract or composition is topically administered to the subject.

Embodiment 41

The method of embodiment 24 or 25, wherein the subject is a human.

Embodiment 42

The method of embodiment 24 or 25, wherein the subject is a non-human animal.

Embodiment 43

A method for inhibiting expression of Bcl-2, Bak, and p53 genes; inhibiting expression of the COX-2 and NF-kB genes; inhibiting production of phosphorylated target of rapamycin (TOR); modulating AMP-activated protein kinase (AMPK); inhibiting protein kinase B (AKT) signaling, modulating the Ras/Raf/MEK/ERK signaling pathway, and modulating the Ras/PI3K/PTEN/Akt/mTOR signaling pathway, comprising contacting a target cell with an effective amount of an extract or composition of any one of embodiments 1 to 23 in vitro or in vivo.

Embodiment 44

The method of embodiment 43, wherein the method is for modulating the Ras/Raf/MEK/ERK signaling pathway in vivo, and wherein the extract or composition inhibits mTOR activity and increases longevity.

Embodiment 45

A method for promoting longevity of a cell in vitro or in vivo, comprising contacting a target cell in vitro or in vivo with an effective amount of an extract or composition of any one of embodiments 1 to 23.

Embodiment 46

A method for promoting longevity of a subject, comprising administering an effective amount of an extract or composition of any one of embodiments 1 to 23.

Embodiment 47

The method of embodiment 46, wherein the extract or composition is administered orally or parenterally.

Embodiment 48

A method for inhibiting the metabolism of a cancer cell, comprising contacting the target cancer cell in vitro or in vivo with an effective amount of an extract or composition of any one of embodiments 1 to 23.

Embodiment 49

A method for producing a carbon dioxide extract of *Curcuma amada* or composition of any one of embodiments 1 to 23, comprising subjecting *C. amada* material to carbon dioxide extraction.

Embodiment 50

The method of embodiment 49, wherein the carbon dioxide extraction is supercritical carbon dioxide extraction or liquid carbon dioxide extraction.

Embodiment 51

The method of embodiment 50, wherein the carbon dioxide extraction includes no more than 10% of ethanol as a co-solvent.

Embodiment 52

The method of embodiment 51, wherein the method includes no co-solvent extraction (i.e., the carbon dioxide extraction includes 0% of ethanol as a co-solvent).

Embodiment 53

The method of any one of embodiments 49-52, wherein the method does not include boiling (such as boiling the carbon dioxide extract in solvent followed by evaporation of the solution to dryness or steam distillation).

Embodiment 54

The method of embodiment any one of embodiments 50 to 51, wherein dried *C. amada* rhizome is used as starting material for the carbon dioxide extraction.

Embodiment 55

The method of embodiment 54, wherein the *C. amada* material is in the form of a powder.

Embodiment 56

The method of embodiment any one of embodiments 50 to 55, wherein the method further comprises conditioning the *C. amada* material by cutting and milling the *C. amada* material into a powder.

Embodiment 57

The method of embodiment 55 or 56, wherein the powder has a particle distribution in the range of about 0.2 to about 0.6 mm.

Embodiment 58

The method of embodiment any one of embodiments 51 to 53, further comprising conducting water separation comprising warming and centrifugation of the supercritical extract.

Embodiment 59

The method of embodiment any one of embodiments 50 to 58, wherein the extract comprises at least about 5% (E)-Labda-8(17),12-diene-15,16-dial (LDD).

Embodiment 60

The method of any one of embodiments 50 to 59, wherein the extract comprises α-pinene, camphene, 3-pinene, 3-myrcene, limonene, 3-phellandrene, β-cariophyllene, ar-curcumene, α-zingiberene, and (E)-Labda-8(17),12-diene-15,16-dial (LDD).

Embodiment 61

The method of any one of embodiments 48 to 58, further comprising combining the extract with a natural or synthetic oil.

Embodiment 62

The method of embodiment 61, wherein the natural or synthetic oil comprises one or more medium chain triglycerides.

Embodiment 63

The method of embodiment 61, wherein the natural or synthetic oil comprises medium chain fatty acids (e.g., C7, C8, or C10) or normal chain fatty acids (e.g., C16 or C18).

Embodiment 64

The method of embodiment 61, wherein the natural or synthetic oil comprises triheptanoin.

Embodiment 65

The method of embodiment 61, wherein the natural or synthetic oil comprises a vegetable oil.

Embodiment 66

The method of embodiment 61, wherein the natural or synthetic oil comprises at least one natural oil selected from among olive oil, chia seed oil, soy germ oil, pomegranate oil, fish oil, and seafood oil.

Embodiment 67

The method of any one of embodiments 50 to 66, further comprising combining the extract with an agent selected from among a botanical extract, mineral, vitamin, nutrient, other nutraceutical, dietary supplement, or active pharmaceutical ingredient.

Embodiment 68

The method of any one of embodiments 50 to 66, further comprising combining the extract with an active pharmaceutical ingredient, and wherein the active pharmaceutical ingredient is one or more chemotherapeutic agents.

Embodiment 69

The method of any one of embodiments 50 to 66, further comprising combining the extract with a botanical extract selected from among a sterol, sterone, steroid, polyphenol, flavonoid, terpenoid, alkaloid, or a polysaccharide.

Embodiment 70

The method of any one of embodiments 50 to 66, further comprising combining the extract with an antioxidant.

Embodiment 71

A method for inhibiting contamination, comprising applying an effective amount of an extract or composition of any one of embodiments 1 to 23 to a surface.

Embodiment 72

A kit comprising an extract or composition of any of embodiments 1 to 23; a container containing the extract or composition; and packaging material.

Embodiment 73

The kit of embodiment 72, further comprising instructions for carrying out the method of any one of embodiments 24 to 43, or 71.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Definitions

In order that the present disclosure may be more readily understood, certain terms are first defined. Additional definitions are set forth throughout the detailed description.

As used in this specification, the singular forms "a", "an", and "the" include plural reference unless the context clearly dictates otherwise. Thus, for example, a reference to "an agent" means one or more such agent.

The term "abnormal cell growth" is used herein to include cell growth which is undesirable or inappropriate. Abnormal cell growth also includes proliferation which is undesirable or inappropriate (e.g., unregulated cell proliferation or undesirably rapid cell proliferation). Abnormal cell growth can be benign and result in benign masses of tissue or cells, or benign tumors. Abnormal cell growth can also be malignant and result in malignancies, malignant masses of tissue or cells, or malignant tumors. Many art-recognized conditions and disorders are associated with malignancies, malignant masses, and malignant tumors including cancer.

The terms "administration" or "administering" can be used to refer to contacting (bringing into contact) an extract or composition with cells or tissues in vitro or in vivo. For example, an extract or composition can be contacted with cells or tissues, either in vivo or ex vivo to test the activity of a system, as well as to diagnose, prevent, treat, or ameliorate a symptom of a condition. An extract or composition can be administered to a subject in vivo using any delivery route appropriate for the desired condition or effect(s). In another example, an extract or composition can be administered ex vivo by combining the compound with cell tissue from the subject for purposes that include, but are not limited to, assays for determining utility and efficacy of the extract or composition. Also, the extract or composition can be used in vitro to test its stability, activity, toxicity, efficacy, and the like. When the extract or composition is administered in vitro or in vivo, the terms "administration" or "administering" are inclusive of contacting the cells or tissues with one or more additional agents simultaneously (within the same or separate formulations) or sequentially. An extract or composition can be formulated to be compatible with its intended route of administration (or other intended use).

The term "anti-cancer agent" is used herein to refer to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). Anti-cancer agents that may be used include but are not limited to those listed in Table 2. In some embodiments, the anti-cancer agent is a chemotherapeutic agent selected from among an alkylating agent (e.g., temozolomide, cyclophosphamide), an inhibitor of topoisomerase I and/or II (e.g., etoposide, irinotecan), and an inhibitor of microtubule assembly (e.g., vinblastine, vincristine).

The term "cancer" is used herein to refer to or describe the physiological condition in organisms that is typically characterized by unregulated cell growth (abnormal cell growth) such as neoplasms, and includes conditions in which cells undergo an abnormal pattern of growth, such as dysplasia (pre-cancer). The cancer, a type of cell proliferation disorder, may be primary or a metastatic offshoot of a primary tumor (secondary neoplasm). The cancer may be a drug-resistant or drug-sensitive type. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, gastrointestinal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; colorectal cancer; esophageal cancer; eye cancer; cancer of the head and neck; gastric cancer; glioblastoma, intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer (melanoma); stomach cancer; testicular cancer; uterine cancer; cancer of the urinary system, as well as other carcinomas and sarcomas. Examples of cancer types that may potentially be treated using the compositions and methods of the present invention are also listed in Table 1.

The terms "cell proliferation disorder" and "proliferative disorder" are used herein to refer to or describe a physiological condition in organisms characterized by an abnormal or inappropriate accumulation of a cell population in a tissue (e.g., by abnormal cell growth). This accumulation of cells may be the result of genetic or epigenetic variation that occurs in one or more cells of the cell population, which causes the cells of the cell population to growth faster, die slower, or differentiate slower than the surrounding, normal tissue. The cell population can include cells of hematopoietic, epithelial, endothelial, or solid tissue origin. Examples of cell proliferation disorders include, but are not limited to, malignant neoplasms (often called cancer), in situ neoplasms, benign neoplasms (e.g., uterine fibroids, melanocystic nevi (skin moles)), psoriasis, fibrosis (e.g., pulmonary fibrosis), diabetic retinopathy, retrolental fibrioplasia, neovascular glaucoma, angiofibromas, rheumatoid arthrtis, hemangiomas, and Karposi's sarcoma.

The term "chemotherapeutic agent" is used herein to refer to a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, cyclophosphamide, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. A chemotherapeutic agent may utilize one or more mechanisms of action, such as alkylation of DNA (alkylating agents), inhibition of topisomerase I or II, or inhibition of microtubule assembly. Several examples of chemotherapeutic agents that may be used in conjunction with the extracts and compositions of the invention are included among the anti-cancer agents in Table 2.

The term "cytotoxic agent" is used herein to refer to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

The terms "eliminating" and "substantially reducing", such as in the context of treatment, are used herein to refer to therapeutic or preventative measures described herein. The methods of "eliminating or substantially reducing" employ administration of an extract or composition of the invention to a subject having a condition, such as a cell proliferation disorder (e.g., cancer). In some embodiments, the term "eliminating" refers to a complete remission of the condition in a subject treated using the methods described herein. In some embodiments, a subject is in complete remission at the time the extract or composition of the invention is administered.

The term "immune disorder" as used herein refers to a condition exhibiting abnormal or inappropriate activation and/or response of the immune system in a subject. Inappropriate immune responses include allergic responses to an innocuous environmental antigen. The term "immune disorder" encompasses, for example, pathological inflammation, inflammatory disorders, and autoimmune disorders.

The term "inflammation" as used herein refers to the accumulation of immune cells systemically or in a particular location of the body. In response to an infective agent, foreign substance, or trauma, for example, immune cells typically secrete cytokines which, in turn, modulate immune cell proliferation, development, differentiation, or migration. Chronic inflammation can also result from inappropriate immune response to self-antigens, as in the case of autoimmune disease, or other persistent antigens (such as commensal flora).

The term "inflammatory disorder" as used herein refers to a condition of local or systemic inflammatory over-response. Autoimmune inflammatory disorders include inflammation of the joints, central nervous system (CNS), skin, gut and other organs. Such diseases include rheumatoid arthritis (RA), multiple sclerosis (MS), psoriasis (Pso), and inflammatory bowel disorder (IBD), including Crohn's disease (CD) and ulcerative colitis (UC).

The term "modulate" and "modulating" as used herein refer to increasing, activating, decreasing, or inhibiting receptor signaling or pathway activity, e.g., modulating the AMPK signaling pathway.

The term "stable" as used herein refers to an extract or composition that loses less than 10% of its original activity. In some embodiments, the extract or composition can be considered stable if it loses less than 5%, 4%, 3%, 2%, or 1% of its original activity. In some embodiments, an extract or composition is "substantially stable" if it loses greater than about 10% of its original activity, as long as the extract or composition can perform its intended use to a reasonable degree of efficacy. In some embodiments, the extract or composition is substantially stable if it loses activity at an amount greater than about 12%, about 15%, about 25%, about 35%, about 45%, about 50%, about 60%, or even about 70%. The activity loss can be measured by comparing activity at the time of packaging to the activity at the time of administration in vitro or in vivo, and this can include a reasonable shelf-life. In some embodiments, the extract or composition is stable or substantially stable if it remains useful for a period ranging from 3 months to 3 years, 6 months to 2 years, 1 year, or any time period therein in increments of about 1 month.

The term "tumor" as used herein refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MM), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. The extracts, compositions, and methods of the invention can be utilized for early, middle, or late stage disease, and acute or chronic disease.

The terms "treat" or "treatment" are used herein to refer to both therapeutic treatment and prophylactic or preventative measures, wherein the object is to prevent or slow down (lessen) an undesired physiological change or disorder, such as the development or spread of cancer or other disorder. For purposes of this invention, beneficial or desired clinical results (i.e., a positive clinical outcome) include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a composition in accordance with the invention can result in therapeutic treatment or prophylaxis of cancer. "Treatment" can also mean prolonging survival as compared to expected survival if not receiving treatment. Those in need of treatment include those already with the condition or disorder as well as those prone to have the condition or disorder or those in which the onset of the condition or disorder is to be delayed (e.g., prevented). Optionally, the subject may be identified (e.g., diagnosed by a medical professional) as one suffering from the disease or condition prior to treatment with the composition.

The term "effective amount" as used herein refers to an amount of an extract or composition effective for the intended use, e.g., to treat a condition in a subject (human or non-human animal) or inhibit contamination on a surface. In the case of a cell proliferation disorder, such as cancer (which includes pre-cancer), the therapeutically effective amount of a composition may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer (i.e., a positive clinical outcome). To the extent administration prevents growth of and/or kills existing cancer cells, it may be cytostatic and/or cytotoxic.

The term "growth inhibitory amount" as used herein refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

The terms "patient", "subject", and "individual" are used interchangeably herein and are intended to include human and non-human animal species. For example, the subject may be a human or veterinary patient, or an animal model. In some embodiments, the subject is a human or non-human mammal. In some embodiments, the subject is a domesticated mammal, such as a dog, cat, cow, pig, or sheep.

A "pharmaceutically acceptable carrier" is a diluent, adjuvant, excipient, or vehicle with which the extract is administered. A carrier is pharmaceutically acceptable after approval by a regulatory agency having jurisdiction or listing in the U.S. Pharmacopeial Convention or other generally recognized sources for use in subjects. The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. In some embodiments, the composition can also contain minor amounts of wetting agents, emulsifying agents, pH buffering agents, or a combination thereof. Oral formulations, for example, can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences.

Following are examples which illustrate procedures for practicing the invention. These examples should not be construed as limiting. All percentages are by weight and all solvent mixture proportions are by volume, supra and infra, unless otherwise noted.

Materials and Methods for Examples 1-6

Cell Line and Cell Culture.

Human glioblastoma cell line (U-87MG) was purchased from American Type Culture Collection, Manassas, Va. and the cells were grown in RPMI medium supplemented with 10% fetal bovine serum (FBS) and antibiotics in a humidified 5% $CO_2$ incubator maintained at 37° C. The normal mouse embryonic hypothalamus cell line (mHypoE-N1) was purchased from CELLutions Biosystems, Inc, Burlington, Ontario, Canada and was grown in DMEM, supplemented with 10% FBS and antibiotics in the $CO_2$ incubator.

Drugs and *Curcuma* Extract.

Supercritical $CO_2$ extract of *Curcuma amada*, was prepared by Flavex Naturextrakte GmbH, Rehlingen, Germany. The supercritical $CO_2$ extraction is designed to extract all the potential compounds in a uniform product without any residue of organic solvents using high pressure $CO_2$ unlike other solvent extraction methods. Moreover, the extracted product, usually in a liquefied form, maintains almost similar quality from batch to batch. Temozolomide, etoposide and curcumin were purchased for the investigation from Sigma-Aldrich, St. Louis, Mo. and TURMERIC FORCE™ extract was obtained from New Chapter Inc. VT.

Cytotoxicity.

Glioblastoma (U-87MG) cells were treated with increasing concentrations of CA, temozolomide, etoposide or their combination for 72 hours in 96-well plates. MTT [3-(4,5-Dimethyl thiazol-2-yl)-2,5-diphenyltetrazolium bromide] assay performed with the Cell Proliferation Kit I (Roche Biochemicals, IN) was used to analyze cytotoxicity of individual drugs/extracts and their combinations. The experiments were repeated four times with three replications for each treatment and the $IC_{50}$, $IC_{75}$ and $IC_{90}$ values were calculated (Ramachandran et al. 2010; Ramachandran et al. 2012). The relative cytotoxicity of CA in normal mouse hypothalamus cell line (mHypoE-N1) was also analyzed to compare the toxicity and specificity of CA in normal and brain tumor cells.

CompuSyn Analysis.

To determine the synergistic/additive/antagonistic effect among temozolomide, etoposide and CA, cytotoxicity data was analyzed further using CompuSyn software. (ComboSyn, Inc. Paramus, N.J.). This program is based on Chou and Talalay's (Chou and Talalay 1983) multiple drug-effect equations and it defines synergism as more-than-expected additive effect and antagonism as a less-than-expected additive effect (Ramachandran et al. 2010; Ramachandran et al. 2012). The combination index (CI) was calculated by the Chou-Talalay equations for multiple drug effects which take into account both potency (IC values) and shape (slope, m) of dose-effect curve.

Apoptosis Assay.

U-87MG cells ($10^6$/2 ml) were treated with increasing concentrations of CA in a $CO_2$ incubator at 37° C. for 48 h. The drug and/or extract-treated cells were stained with Annexin V-FLUOS kit (Roche Biochemicals, IN) for 15 min and analyzed in a Beckman Coulter Elite flow cytometer. The percentages of apoptotic, necrotic, and live cells were estimated from gated flow cytometric scatter diagrams and the percentage of apoptotic cells were plotted against CA concentrations (Ramachandran et al. 2010).

Gene Expression Studies by RT-PCR Assay.

U-87MG cells ($2 \times 10^6$) were plated in 5 ml of RPMI medium and treated with increasing concentrations of CA (0-100 µg/ml) for 72 hours after cell attachment. Tumor cells treated with camptothecin (5 µg/ml) which induces apoptosis, was used as a positive control. Total RNA was extracted from treated cells and 5 µg RNA was reverse transcribed to synthesize cDNAs. The mRNA expression of genes associated with apoptosis (APOBEC3B, Bax, Bak, Bcl-2, p10, p21, p53 and STAT3), cell proliferation (Ki67, PCNA and Cyclin B2-CCNB2), drug resistance (MDR-1, MRP, LRP and DRP), oncogenesis (C-myc, N-myc and V-jun) and telomerase activity (hTERT and hTER) were analyzed by reverse transcriptase-polymerase chain reaction (RT-PCR) using 0.4 µg of cDNA using gene specific primers (Ramachandran et al. 2014 (in press)). The expression of a housekeeping gene, Glyceraldehyde 3-phosphate dehydrogenase (GAPDH) was used as a control. The expression of gene was quantified using gel pictures from three separate experiments by the UNSCAN-IT GEL™ software (Silk Scientific, Inc., Orem, Utah).

Western Blot Analysis.

U-87MG cells ($5 \times 10^6$/5 ml) were treated with increasing concentration of CA (0-100 µg/ml) for 72 h and total cellular protein was extracted with 0.5 ml of Invitrogen's protein extraction buffer (Invitrogen Corporation, Frederick, Calif.) according to the manufacturer's instructions. The protein concentration was determined and 100 µg protein was separated on 7.5% SDS-PAGE. The separated protein was blotted on a nitrocellulose filter. The filters were hybridized with antihuman monoclonal/polyclonal antibodies specific for each protein (Bax, Bak, Bad, Bcl-2, Bcl-X, p53 and Caspase 3) in a western blot procedure and detected using the Horseradish peroxidase or Alkaline phosphatase color detection kit (Bio Rad Laboratories, Hercules, Calif.). The relative expression of proteins compared to untreated control sample was quantified using UNSCAN-IT GEL™ software (Silk Scientific, Inc., Orem, Utah) and the fold level changes in protein expression were plotted against CA concentrations.

Statistical Analysis.

Mean inhibitory concentrations (ICs) and standard deviation estimates were calculated using Microsoft Excel software using data from three separate experiments. The fraction of surviving cells at each concentration of drugs/combinations was used for the analysis of synergism/additiveness/antagonism between drugs/extracts by the CompuSyn software (ComboSyn, Inc., Paramus, N.J.).

The relative mRNA expressions (average pixel units) at different CA concentrations were statistically analyzed by 1-way ANOVA and the treatments were compared using Dunnett's multiple comparison tests (GraphPad Prism software, La Jolla, Calif.).

Example 1

Cytotoxicity of CA, Etoposide and Temozolomide Against Glioblastoma Cells

Malignant brain tumors are among the most aggressive forms of human cancer with a high degree of morbidity and mortality. In the United States, more than 190,000 people are diagnosed with brain tumors every year, of which 40,000 are primary (Greenlee et al. 2000). Gliomas, especially glioblastoma multiformae, are the deadliest and the most common form of malignant brain cancer with the survival in most cases limited to a few months after diagnosis. Chemotherapy options for brain cancer, especially high grade gliomas, are significantly limited due to the poor penetration of the blood-brain barrier and/or drug resistance of cancer cells (Greenlee et al. 2000; Regina et al. 2001). It has been reported that curcumin, the natural polyphenol from *Curcuma longa* (turmeric) rhizomes can cross the blood-brain barrier (Perry et al. 2010).

CA demonstrates significant cytotoxicity in the U-87MG glioblastoma cell line compared to a normal mHypoE-NI cell line, as indicated by the cytotoxicity curves presented in FIG. 1. The $IC_{50}$, $IC_{75}$ and $IC_{90}$ values of CA are 4.92±0.81, 12.87±0.85 and 21.30±1.13 µg/ml, respectively, which is much lower than the values for curcumin ($IC_{50}$=37.3±4.04; $IC_{75}$=51.00±7.07; $IC_{90}$>200 µg/ml) and TURMERIC FORCE™ extract (38.51±7.07; $IC_{75}$=40.40±2.97; $IC_{90}$=48.50±0.58 µg/ml). The CA $IC_{50}$, $IC_{75}$ and $IC_{90}$ values for normal brain cell line (mHypoE-N1) are 40.57±0.06, 62.60±1.55, 85.43±5.03 µg/ml, respectively, which are significantly higher than that for U-87MG cell line indicating the specificity of CA towards brain tumor cells.

The cytotoxicity values for temozolomide and etoposide in U-87MG cell line (Table 3) indicates that both these agents, unlike CA, have limited efficacy for inducing high percentage of cell death even at high doses. However, CA alone and in combination with temozolomide and etoposide is more effective than single agents in inducing >90% cell death.

Example 2

Synergistic Effect of CA with Temozolomide and Etoposide

The dose-effect plot and medium-effect plots of combinations of temozolomide and etoposide with CA are presented in FIGS. 2A-D and the combination index (CI) values are given in Table 4. Temozolomide and etoposide with CA show synergistic cytotoxicity as indicated by CI values of <1 (Table 4).

Example 3

CA-Induced Apoptosis

Figure 3:
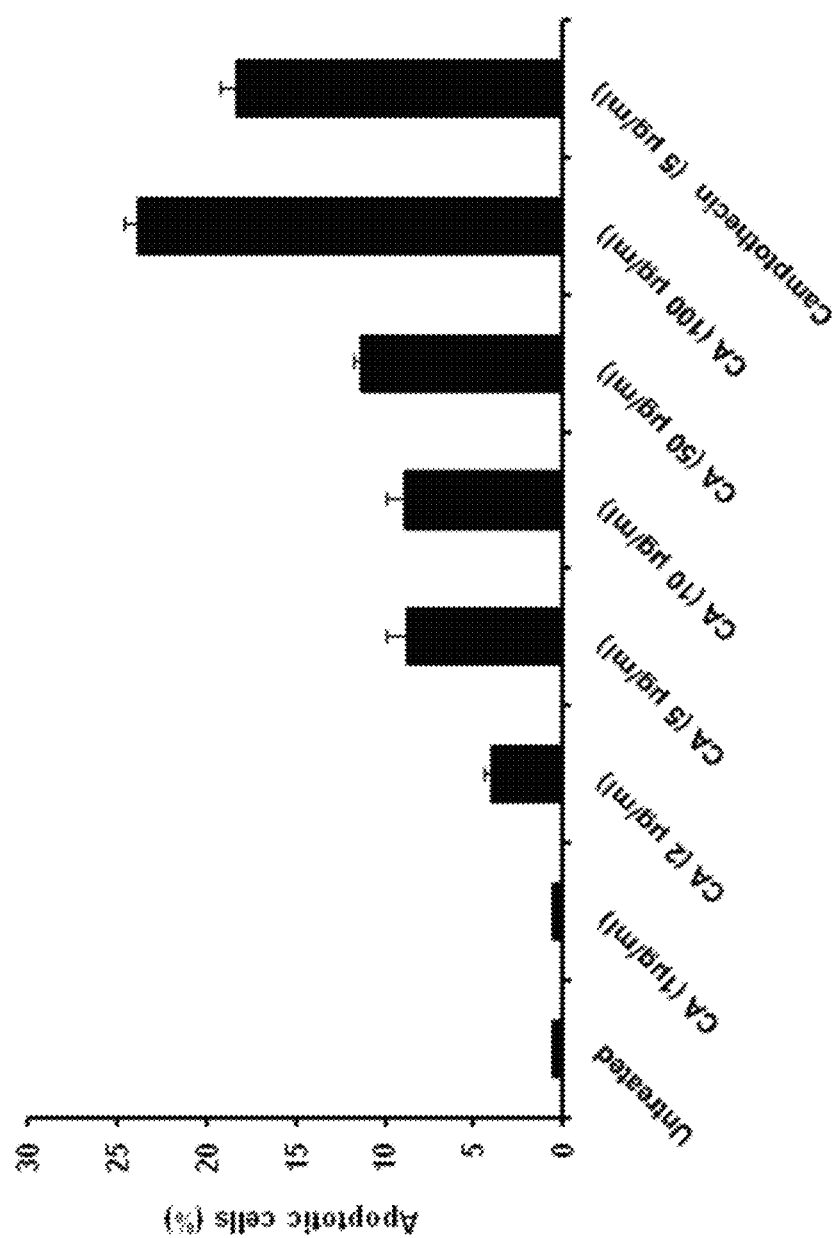
FIG. 3: Analysis of apoptosis induced by CA in U-87MG cell line. Cells were treated with CA for 48 h and stained with Annexin-V-FLUOS kit (Roche Biochemicals, Indianapolis, Ind.). The percentage of apoptotic cells were plotted against CA concentrations (0-100 μg/ml) and the Camptothecin (5 μg/ml) treated positive control.
Figure 4:
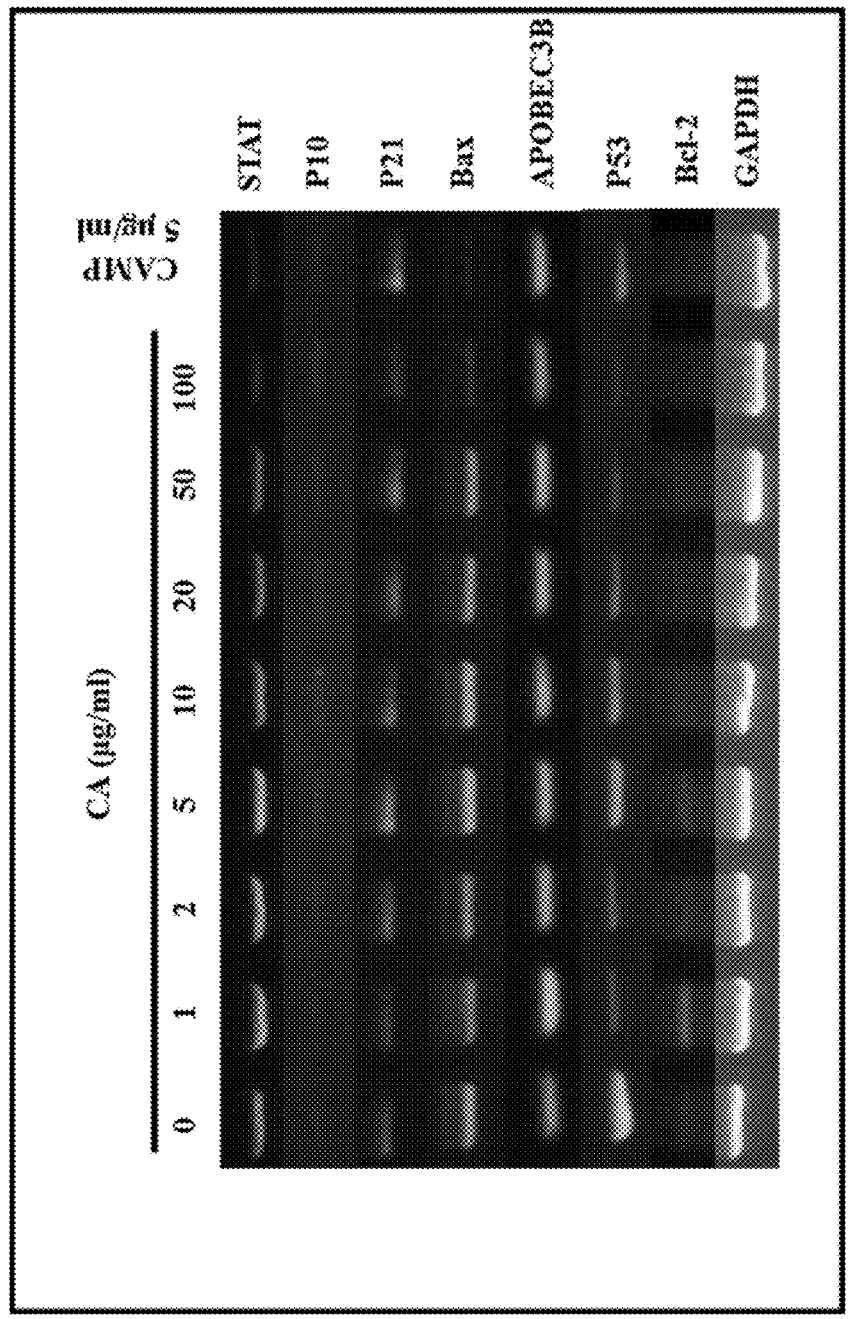
FIG. 4: RT-PCR assay of apoptotic gene expression (STAT3, p10, p21, Bax, APOBEC 3B, p53, and Bcl-2) along with housekeeping gene GAPDH in CA-treated U-87MG cells.
Figures 5A, 5B, 5C, 5D, 5E, 5F, 5G, 5H, 5I:
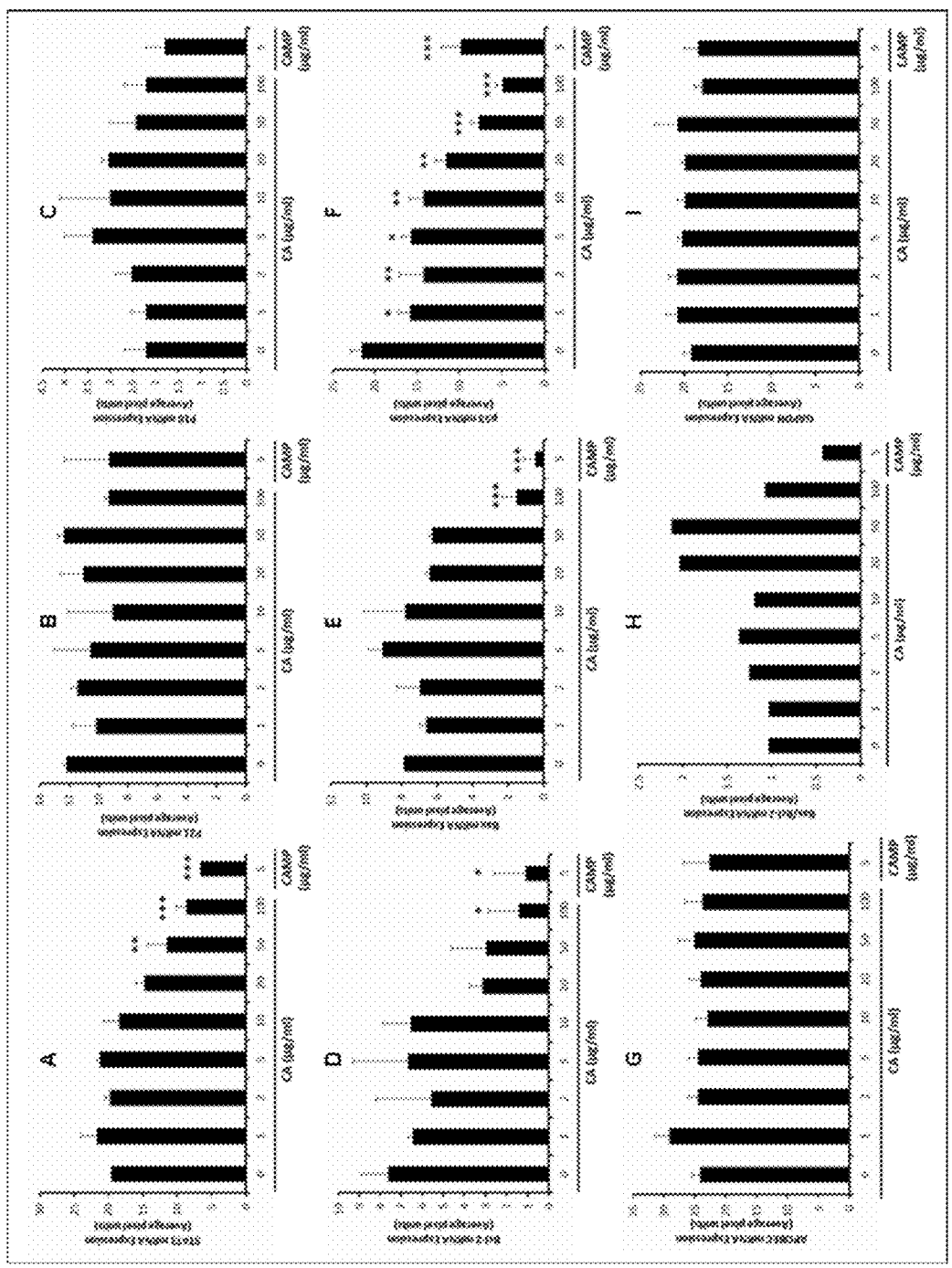
FIG. 5A-5I: Quantification of expression of apoptotic genes by UNSCAN-IT gel software. The relative expression of genes (average pixel units) as well as Bax/Bcl-2 ratio is plotted against CA concentrations. The significant difference between treatments was compared by 1-way ANOVA with Dunnett's multiple comparison test (GraphPad Prism software, La Jolla, Calif.).
Figure 6:
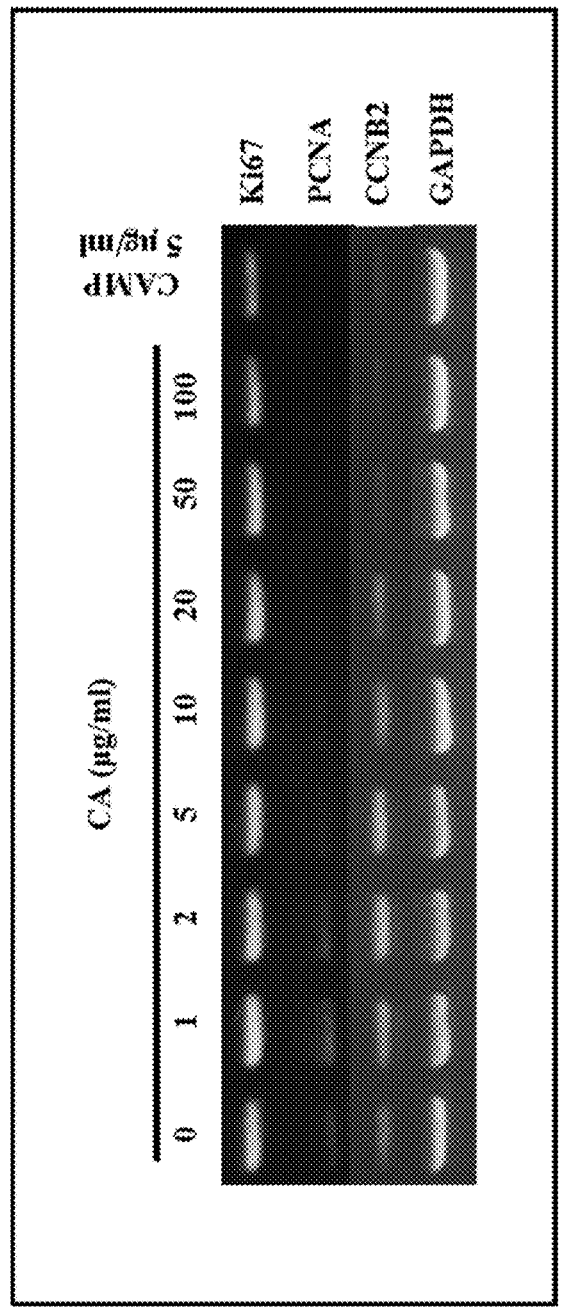
FIG. 6: RT-PCR assay of cell proliferation gene expression (Ki67, PCNA and CCNB2-cyclin B2) along with housekeeping gene (GAPDH) in CA-treated U-87MG cell line.
Figures 7A, 7B, 7C, 7D:
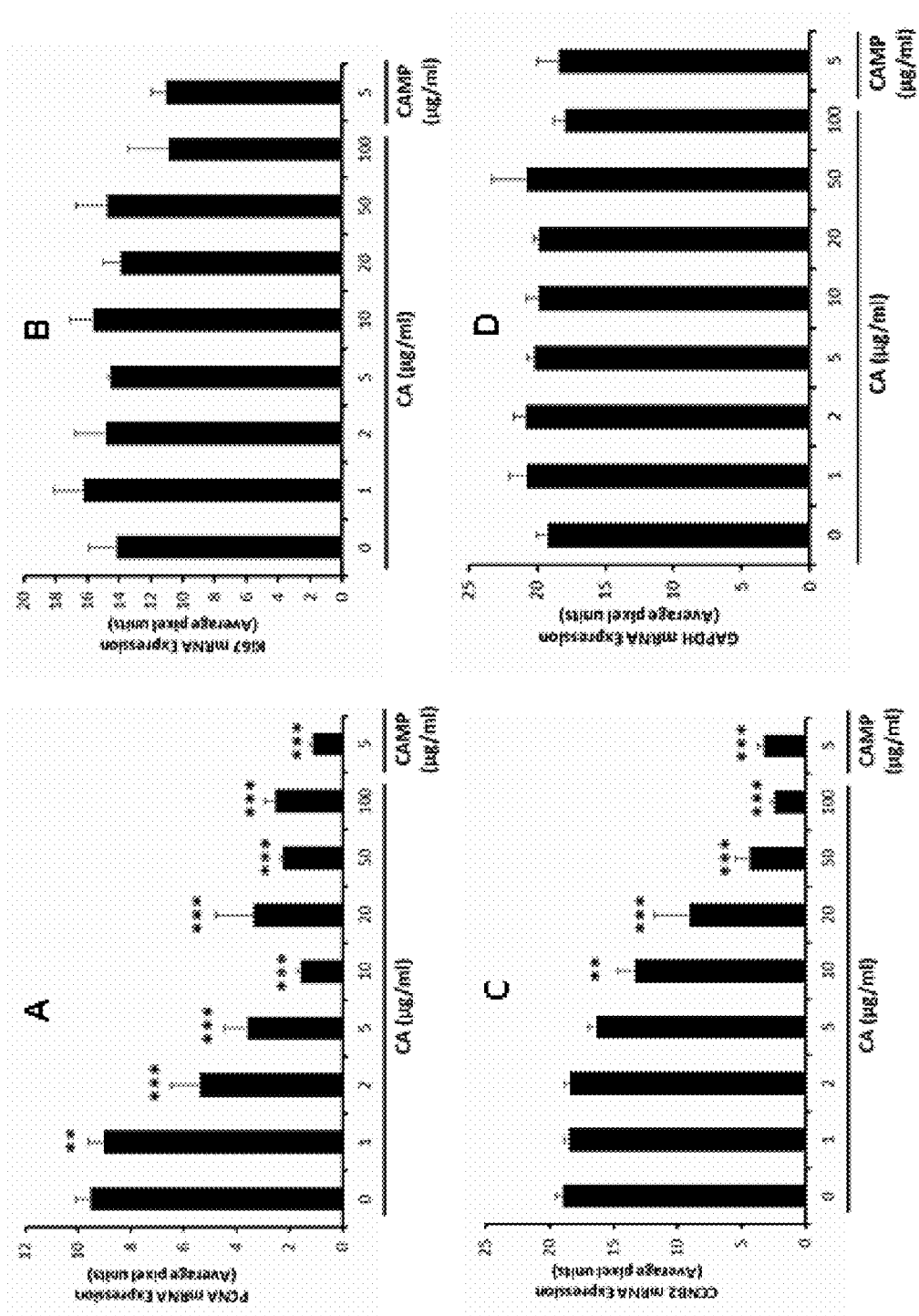
FIGS. 7A-7D: Quantification of expression of cell proliferation genes by UNSCAN-IT gel software. The relative expression of gene (average pixel units) was plotted against CA concentrations. The significant difference between treatments was compared by 1-way ANOVA with Dunnett's multiple comparison test (GraphPad Prism software, La Jolla, Calif.).
Figure 10:
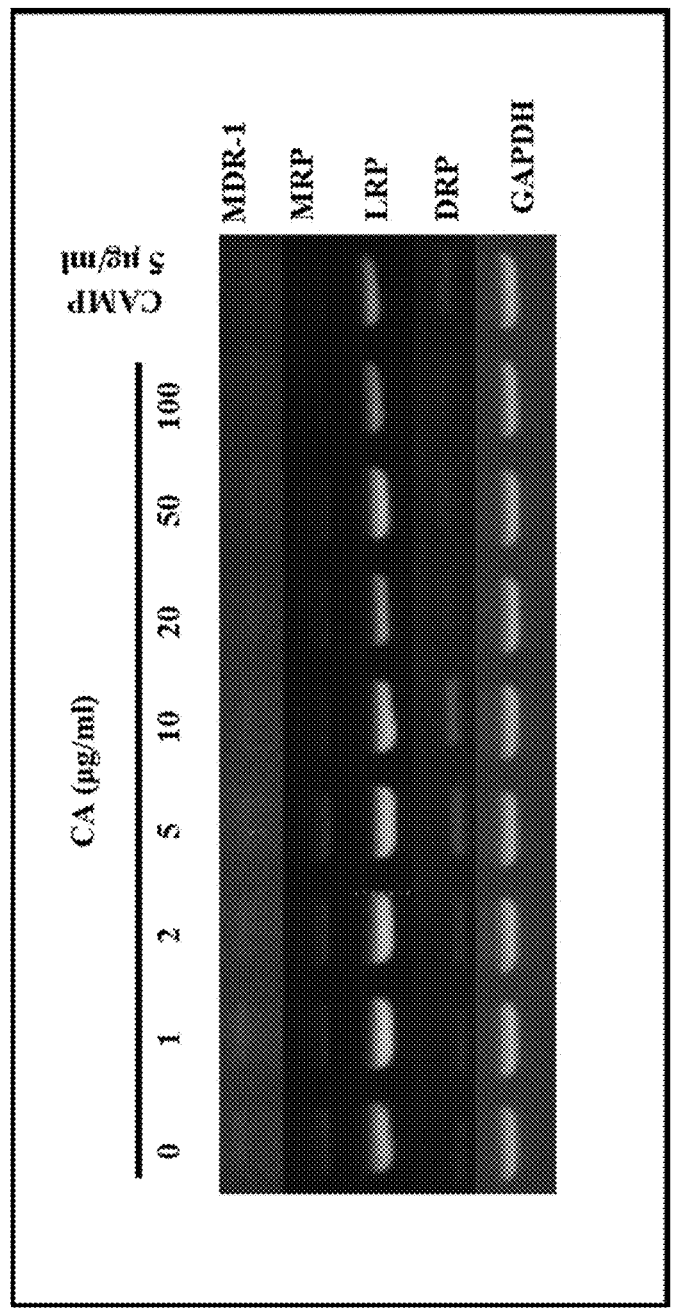
FIG. 10: RT-PCR assay of expression of genes associated with drug resistance (MDR-1, MRP, LRP and DRP) along with housekeeping gene GAPDH in U87MG cell line.
Figures 11A, 11B, 11C, 11D, 11E:
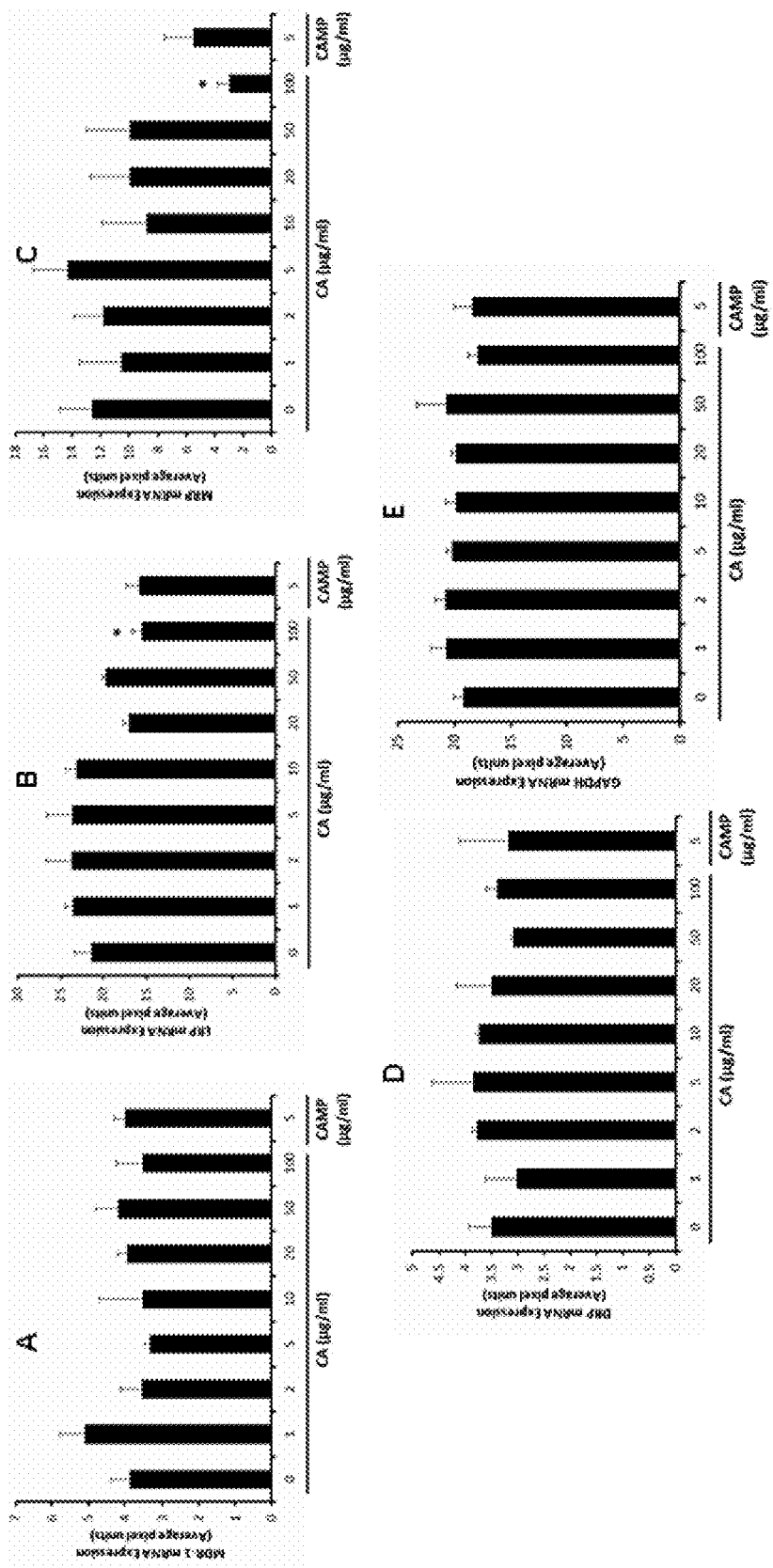
FIGS. 11A-11E: Quantification of expression of drug resistance associated genes by UNSCAN-IT gel software. The relative expression of gene (average pixel units) was plotted against CA concentrations. The significant difference between treatments was compared by 1-way ANOVA with Dunnett's multiple comparison test (GraphPad Prism software, La Jolla, Calif.).
Figure 12:
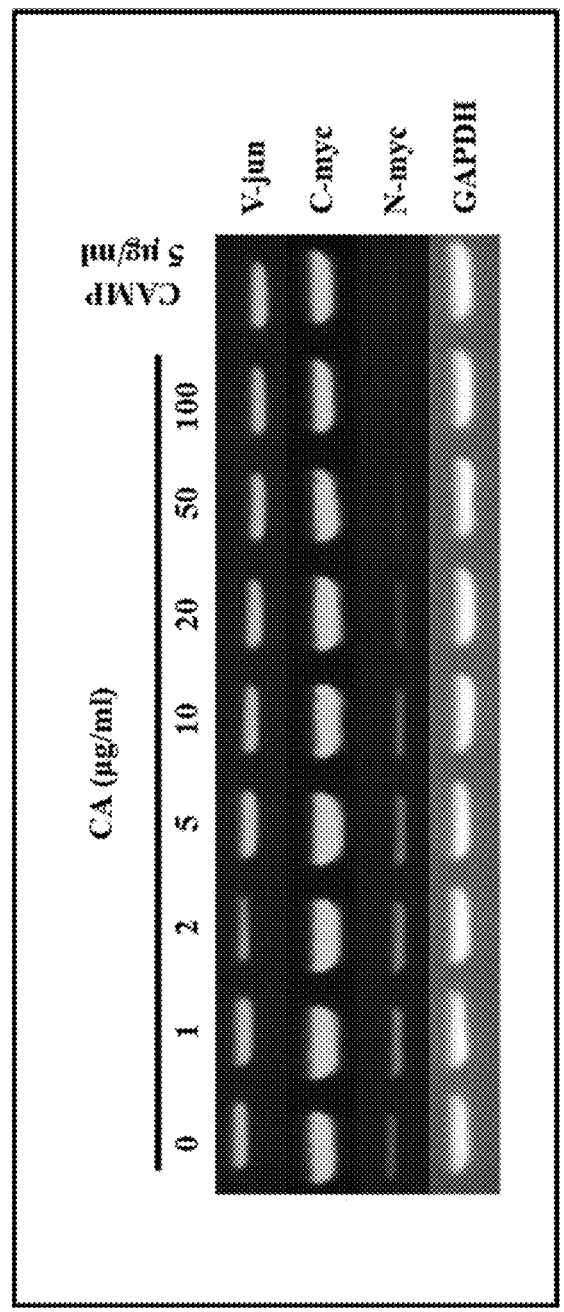
FIG. 12: RT-PCR assay of expression of genes associated with oncogenesis (N-myc, C-myc and V-jun) along with housekeeping gene GAPDH in U87MG cell line.
Figures 13A, 13B, 13C, 13D:
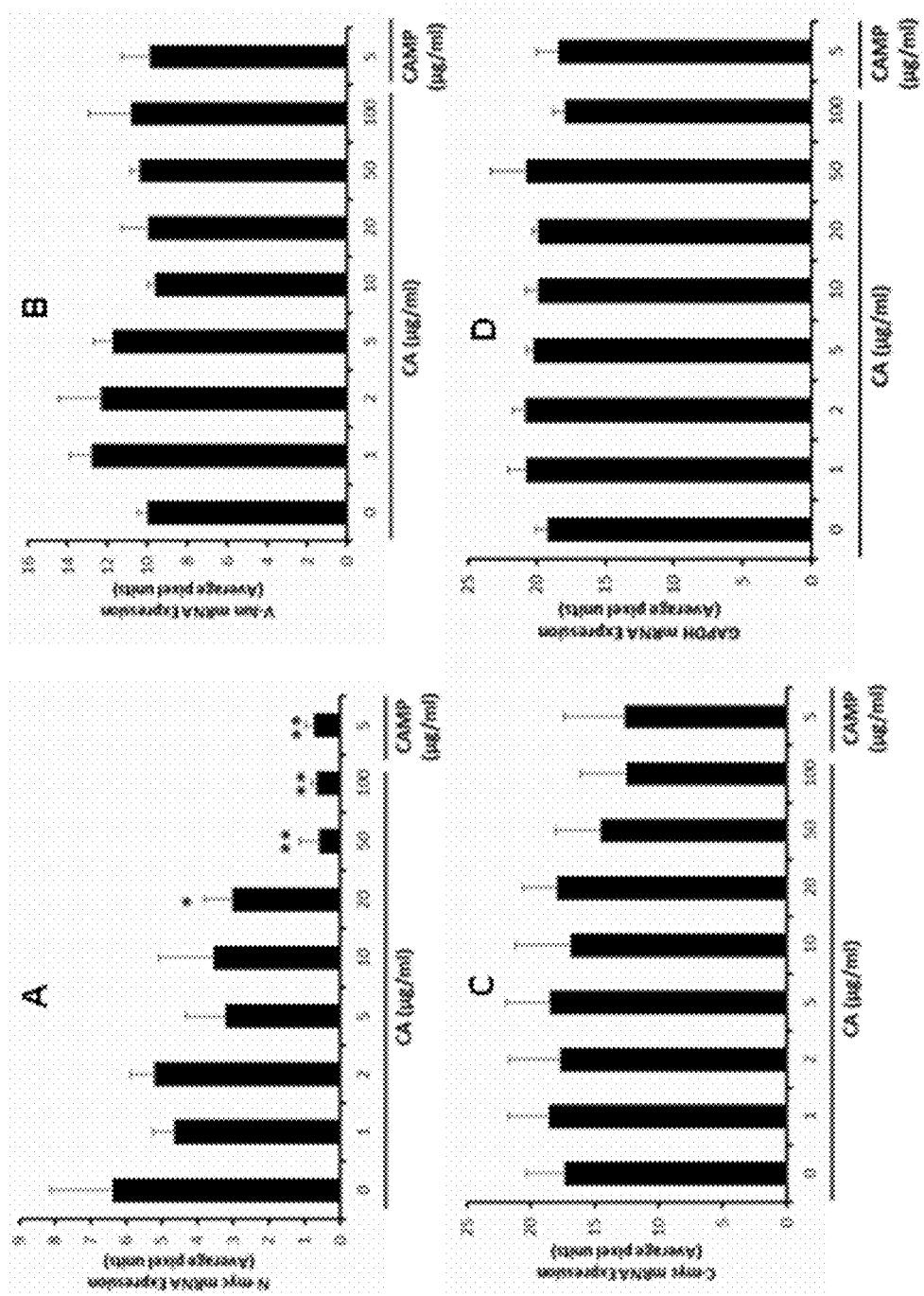
FIGS. 13A-13D: Quantification of expression of genes associated with oncogenesis by UNSCAN-IT gel software. The relative expression of genes (average pixel units) is plotted against CA concentrations. The significant difference between treatments was compared by 1-way ANOVA with Dunnett's multiple comparison test (GraphPad Prism software, La Jolla, Calif.).

The results of Annexin-V-FLUOS staining indicated that CA induces apoptosis in a dose-dependent manner (FIG. 3). CA induced 8.7%, 11.4% and 23.7% apoptosis at 10, 50 and 100 µg/ml concentrations, respectively, in 48 hours.

Example 4

Effect of CA on Gene-Specific mRNA Expression

The expression of mRNAs of genes associated with apoptosis, cell proliferation, telomerase activity, drug resistance and oncogenesis were analyzed by RT-PCR and the results are presented in FIGS. 4 to 12. The relative changes in mRNA expression induced by increasing concentrations of CA are given in graphs (FIGS. 5A to 13A-D). Among the genes associated with apoptosis, CA treatment induces down-regulation of STAT3, Bcl-2 and mutant p53 expression. The ratio of Bax/Bcl-2 was also increased by CA, indicating the level of apoptosis (FIGS. 4 and 5A-I).

CA treatment of U87-MG cells also down-regulates the transcription of genes associated with cell proliferation (proliferating cell nuclear antigen (PCNA) and cyclin B2 (CCNB2)), although Ki67 is unchanged (FIGS. 6 and 7A-D). The inventors have analyzed the expression of two important genes associated with telomerase elongation, human telomerase reverse transcriptase (hTERT) and human telomerase genes (hTER) in CA treated U-87MG cells. CA treatment significantly down-regulates the expression of hTERT mRNAs among the two important genes associated with telomerase elongation (FIGS. 8 and 9A-C). Among the drug resistance genes, low level down-regulation is observed in LRP and MRP genes (FIGS. 10 and 11A-E). CA treatment also down-regulates the expression of oncogenes like N-myc to a large extent and C-myc to a small extent (FIGS. 12 and 13A-D).

Example 5

Effect of CA on Gene Expression in U-87MG Cells

Figure 14:
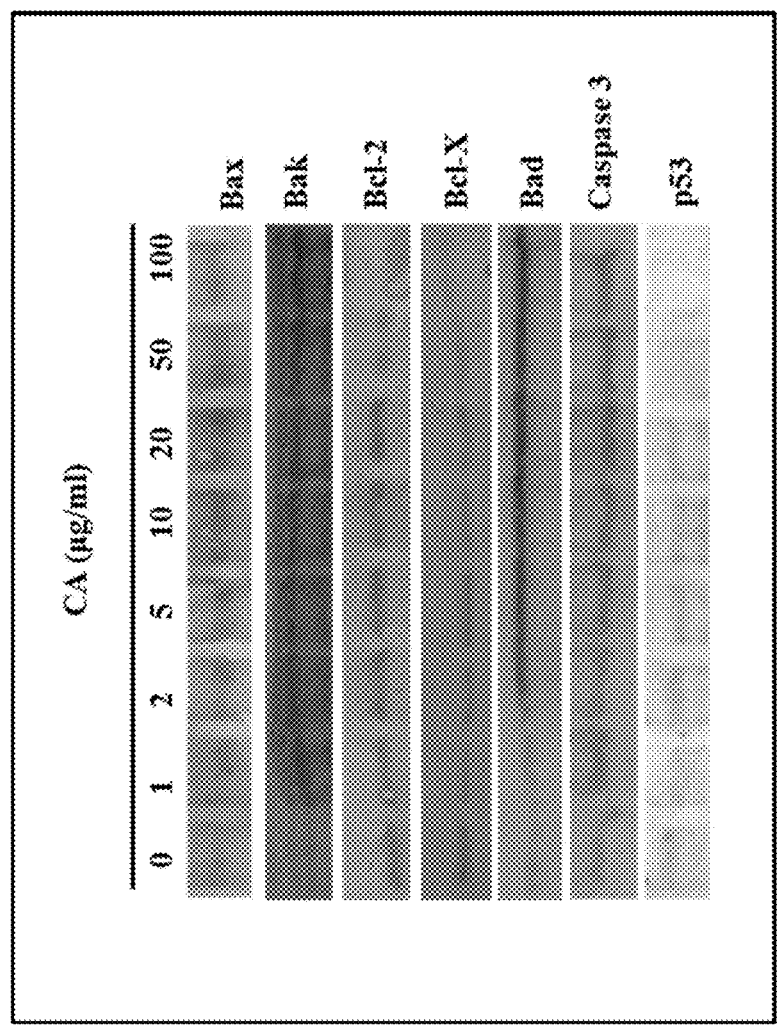
FIG. 14: Western blot analysis of apoptotic proteins (Bax, Bak, Bad, Bcl-2, Bcl-X, p53 and Caspase 3). Total proteins (100 μg) were separated on 7.5% polyacrylamide gels, transferred to nitrocellulose filter, hybridized with gene specific antibodies and detected using Bio-Rad Horseradish peroxidase or Alkaline phosphatase coloring reagent.
Figure 15:
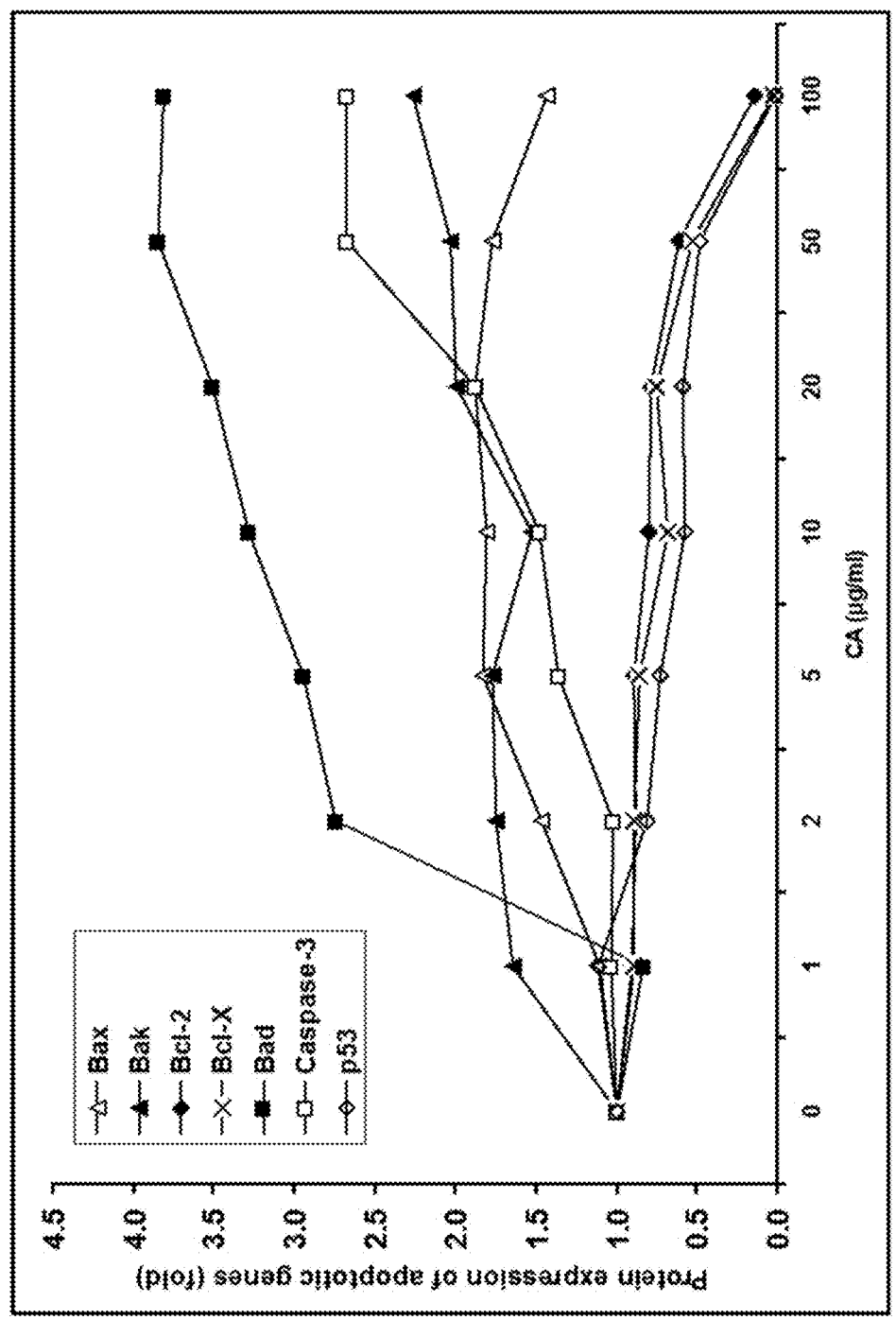
FIG. 15: Quantification of protein expression associated with apoptosis by UNSCAN-IT gel software. The relative protein expression (fold change based on untreated control) was plotted against CA concentrations.

The results of protein expression analyzed by western blot hybridization are presented in FIGS. 14 and 15. CA treatment of U-87MG cells induced an increase in the expression of pro-apoptotic proteins (Bax, Bak, Bad and Caspase 3) with increase in CA doses. On the other hand, the anti-apoptotic proteins (mutant p53, Bcl-2 and Bcl-X) show an overall down-regulation with CA treatment.

Example 6

Glioblastoma Xenograft Studies

Figure 16:
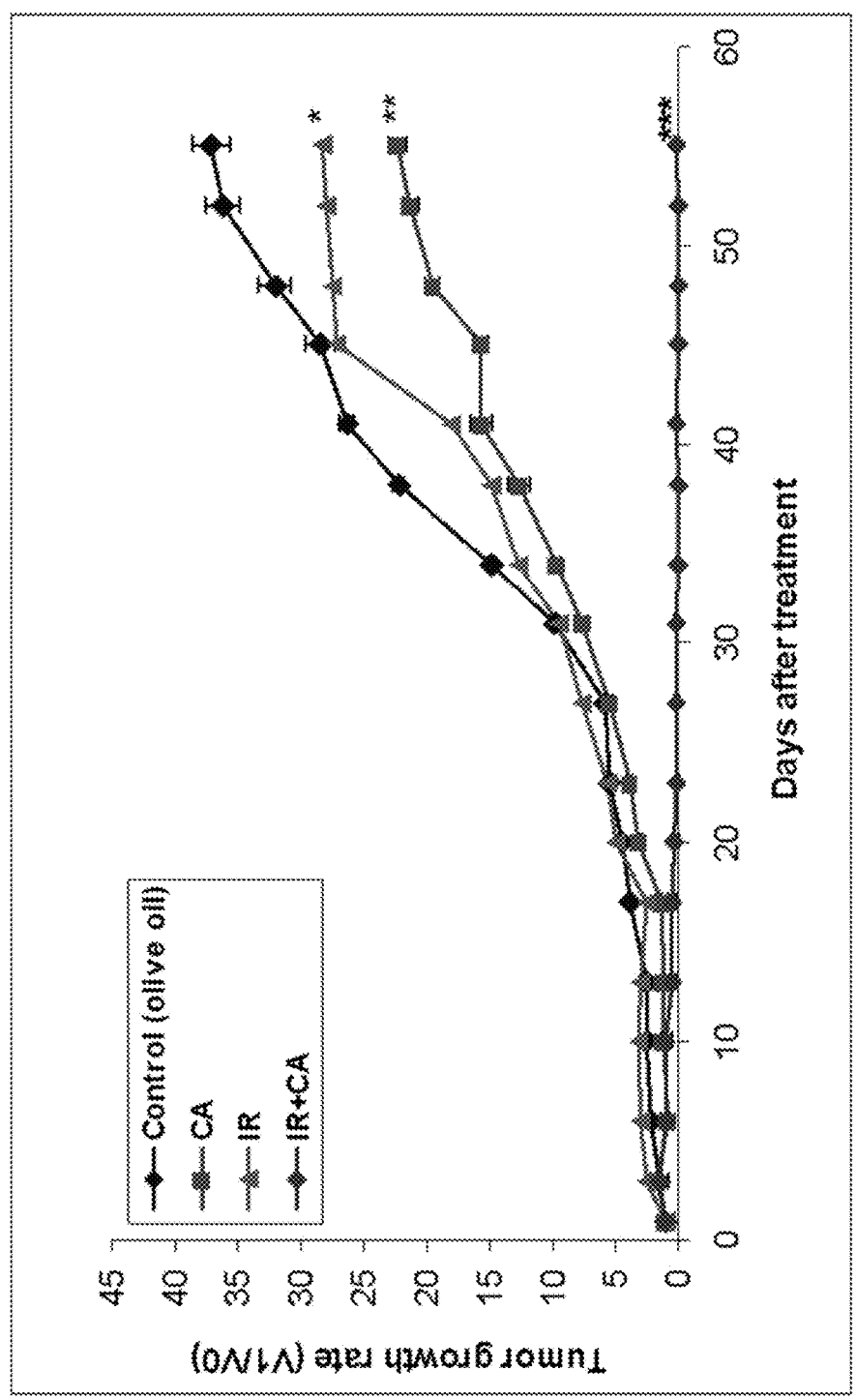
FIG. 16: Inhibition of tumor growth rate in U-87MG xenografts treated with olive oil (control), irinotecan (IR), CA, and IR+CA in combination. Xenografts (n=15/group) were administered intraperitoneally with olive oil (control) or IR (50 mg/kg), whereas CA (50/mg) was given gavage (introduction directly to the stomach). Tumor measurements are recorded twice per week and mean±SD estimates of tumor growth rate are plotted against days after treatment (*$p<0.05$; $p<0.01$, *$p<0.001$ as compared to control).
Figure 17:
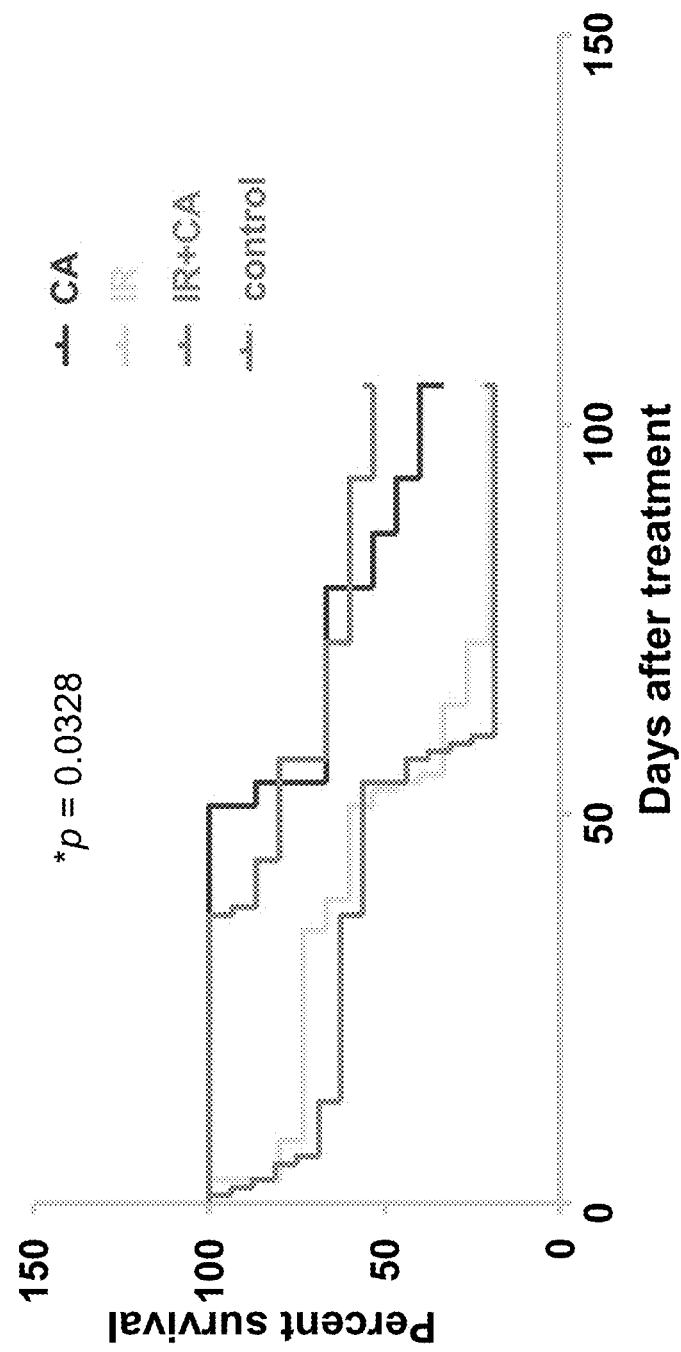
FIG. 17: Kaplan-Meier survival curve analysis of glioblastoma (U-87MG) nude mice xenografts treated with olive oil control, IR, CA, and IR+CA. The difference between treatment groups are significant (*$p<0.05$).
Figures 18A, 18B, 18C, 18D:
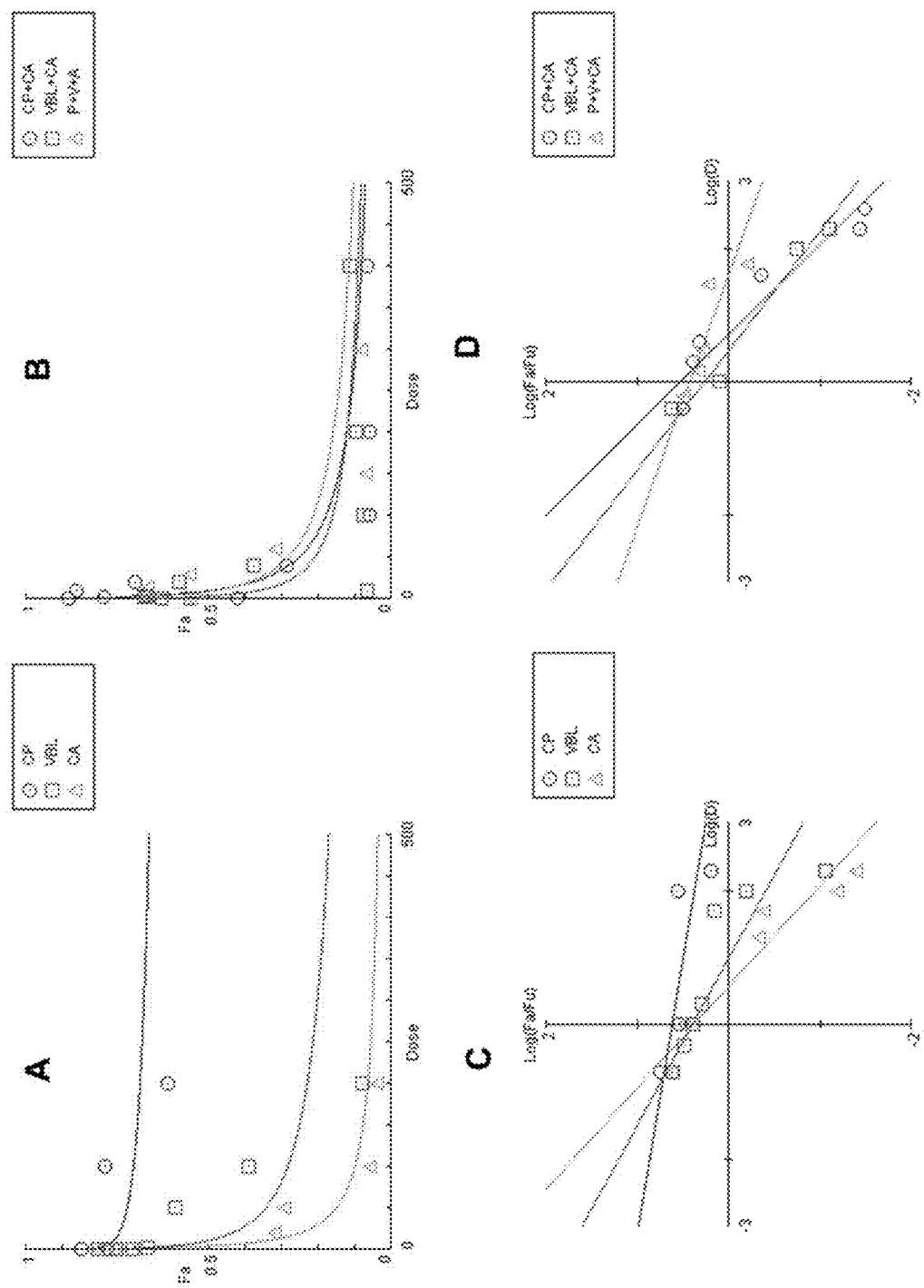
FIGS. 18A-18D: Dose-effect and medium-effect plots of individual drugs and combinations in aRMS cell line SJRH30.

The average tumor growth rates of U-87MG nude mice xenografts in different treatment groups are presented in FIG. 16. Tumor growth rate increased steadily for the control group (treated with olive oil). Tumor growth rate was significantly inhibited in the CA, irinotecan (IR) and IR+CA groups when compared to the control group (p<0.05). CA treatment alone inhibited the tumor growth rate significantly compared to the control group, and the IR+CA combination was still better than CA alone on tumor growth rate inhibition, actually causing the tumor to disappear completely. Kaplan Meier analysis of survival data (FIG. 17) showed that CA-treated U-87MG xenografts survived better than the IR-treated group and the control group, and the IR+CA-treated group survived better than the CA-treated group (*p<0.05).

Materials and Methods for Examples 7-11

Cell Lines.

Both aRMS (SJRH30) and eRMS (RD) cell lines were purchased from American Type Culture Collection, Manassas, Va. SJRH30 and RD cells were grown in Rosewell Park Memorial Institute 1640 (RPMI 1640) and Dulbecco's Modified Eagle's medium (DMEM), respectively, supplemented with 10% FBS and antibiotics in a 5% $CO_2$ incubator.

Drugs and *Curcuma* Extracts.

Vinblastine and cyclophosphamide were purchased from Sigma Chemical Co, USA. The supercritical $CO_2$ extracts of *Curcuma amada*, *Curcuma longa*, and *Curcuma xanthorrhiza* were prepared by Flavex Naturextrakte GmbH, Germany. The supercritical $CO_2$ extraction is designed to extract all the potential compounds in a uniform product without any residue of organic solvents using high pressure $CO_2$ unlike other solvent extraction methods. Moreover, the extracted product usually in a liquefied form maintains almost similar quality from batch to batch.

Cytotoxicity.

Rhabdomyosarcoma cells were treated with increasing concentrations of drugs and/or extracts for 72 hours in 96-well plates. MTT assay performed with the Cell Proliferation kit I (Roche Biochemicals, IN) was used to analyze cytotoxicity of individual drugs, extracts and their combinations (Ramachandran et al. 2012).

Apoptosis Assay.

The drug and/or extract-treated cells were stained with Annexin V-FLUOS kit (Roche Biochemicals, IN) for 15 minutes and analyzed in a Beckman Coulter Elite flow cytometer. The percentages of apoptotic (quadrant 4), necrotic (quadrant 3) and live (quadrant 1) cells were estimated from gated flow cytometric scatter diagrams (Ramachandran et al. 2010).

Caspase 3 Activity.

Cells ($1\times10^6$/ml) were treated with drug and/or extract combinations for 48 h in a humidified $CO_2$ incubator. The cells were harvested by scraping and stained with FITC-labeled anti-active caspase 3 monoclonal antibody (BD Biosciences) and Propidium Iodide (PI) for 30 min and analyzed in a Beckman-coulter flow cytometer using a 2-color protocol. The percentage of caspase 3 positive cells were calculated from scatter diagram and plotted (Ramachandran et al. 2012).

Gene Expression Studies by RT-PCR Assay.

mRNA expression of apoptosis-associated genes (Bax, Bcl-2, Bak and p53) and inflammation-associated genes (Cox-2, NF-κB and STATS) were analyzed by reverse transcriptase-polymerase chain reaction (Ramachandran et al. 2012). The expression of a house keeping gene, Glyceraldehyde 3-phosphate dehydrogenase (GAPDH) was used as a control. The relative expression of genes was quantified using gel pictures by the UNSCAN-IT GEL' software (Silk Scientific, Inc., Orem, Utah). Since the ratios of Bax/Bcl-2, Bak/Bcl-2 and Bax/Bak expression were very much associated with the fate of cells undergoing apoptosis, these estimates were calculated and plotted against drug concentrations (Ramachandran et al. 2012).

Xenograft Studies.

Male athymic nude (nu/nu) mice of the NCrNUstrain (4 weeks old weighing 18-22 g) were purchased from Taconic Labs, German Town, N.Y. Tissue cultured SJRH30 aRMS cells ($10^7$ cells/site) in 0.1 ml of Hank's balanced salt solution were injected subcutaneously into the left and right flank of the nude mice with a 21-guage needle. When the tumors measured 0.5 $cm^3$, therapy was started with 20 mice in each group. Treatment groups included control (saline), 2 mg/kg VBL, 10 mg/kg CA and 2 mg/kg VBL+10 mg/kg CA. VBL was dissolved in saline and administered intraperitoneally on alternate days for a total of 10 injections starting on the first day of tumor measurement and treatment. CA was initially dissolved in ethanol and diluted in water so as to make 0.1% alcohol in it and given as drinking water for the entire duration of the study. Tumor size (length×width), body weight and survival data were collected twice a week. Tumor measurements were recorded using a vernier caliper and tumor volume and tumor growth rates were calculated according to the formula described earlier (Ramachandran et al. 2003; 2006). Tumor growth rate data was analyzed by one-way analysis of variance (ANOVA) with Dunnett's multiple comparison test. Survival data was analyzed with Kaplan Meier statistics using Graphpad Prism software and significant differences among treatment groups were calculated.

Data Analysis.

Mean inhibitory concentrations (ICs) and standard deviation estimates were calculated using Microsoft Excel software. The fraction of surviving cells at each concentration of drugs/combinations was used for the analysis of synergism/additiveness/antagonism between drugs/extracts by the CompuSyn software (ComboSyn, Inc., Paramus, N.J.). Synergism was evaluated by the Combination Index (CI) method of Chou and Talalay (1983) which is based on the median-effect principle. The CIs were calculated by the Chou-Talalay equations for multiple drug effects which take into account both potency (IC values) and shape (slope, m) of dose-effect curve (Ramachandran et al. 2010).

Example 7

Cytotoxic Effects of CA on Rhabdomyosarcoma Cells

Rhabdomyosarcoma (RMS) is a malignant soft tissue sarcoma that is grouped as the most common soft tissue sarcoma of childhood and adolescence, accounting for about 7% of all pediatric cancers (Huh et al. 2010; Saab et al. 2011). RMS is classified based on histology as embryonal (about 60%), alveolar (20%) or other (20%) subtypes. Embryonal (eRMS) and alveolar (aRMS) subtypes have unique genetics, patterns of development, biology, and prognosis. The aRMS occurs more commonly in the extremities and has a high predilection for metastasis while eRMS is more likely to present a localized disease. Patients with aRMS have an inferior survival rate compared to patients with the eRMS, with eRMS and aRMS having five-year overall survival of 80% and 52%, respectively (Davicioni et al. 2009). The aRMS is comparatively refractory and difficult to treat mainly because of emergence of cellular drug resistance especially in advanced stages and during relapse (Seitz et al. 2007). Despite advances in therapy, nearly 30% of children with RMS experience a progressive disease which is often fatal (Pappo et al. 1999). In the chemotherapy regimens, vinblastine/vincristine and cyclophosphamide are commonly used anticancer drugs against rhabdomyosarcomas (Mandell 1993; Minard-Colin et al. 2012). However, these agents have harmful side-effects, and even their therapeutic efficiency is not adequate (Malempati and Hawkins 2012). Adjuvants with the potential to act synergistically or additively with vinblastine or cyclophosphamide would thus be highly advantageous for the treatment of RMS.

Several herbs within the *Curcuma* genus are reported to have anticancer properties, such as *Curcuma longa* (turmeric), *Curcuma amada* (mango ginger), and *Curcuma xanthrorrhiza* (Javanese turmeric). Studies indicate that curcumin, the major active compound in *Curcuma longa* and the hydro-ethanolic plus supercritical extract combination, TURMERIC FORCE™ from *C. longa* are cytotoxic to various types of cancer cells and work synergistically with anticancer drugs including gemcitabine, temozolomide and etoposide (Aggarwal et al. 2003; Ramachandran et al. 2010, 2012). Synergistic effects potentially reduce cancer drug toxicity thereby reducing their harmful side-effects. Policegoudra (2008) reported that organic solvent extract of *C. amada* have higher toxicity towards cancer cells than normal cells and ethyl acetate extract of *C. amada* showed greater toxicity than hexane, chloroform, acetone and methanol extracts. Similarly, anticancer properties of *C. xanthorrhiza* and its active ingredient xanthorrhizol have been described by several investigators (Park et al. 2008; Cheah et al. 2006; Choi et al. 2005; Kang et al. 2009; Tee et al. 2012). However, a systematic comparison of cytotoxic activity of supercritical $CO_2$ extracts of *Curcuma* species and their combination effects with anticancer drugs have not been pursued to date. The inventors have investigated the synergistic cytotoxic effect of supercritical $CO_2$ extracts of three *Curcuma* species (*C. amada, C. longa* and *C. xanthorrhiza*) with conventional chemotherapeutic drugs such as vinblastine (VBL) and cyclophosphamide (CP) in both eRMS and aRMS cell lines.

CA induced $IC_{90}$ level of cell death in both cell lines, whereas CP induced only 45% cell death at 200 µg/ml dose in aRMS cells (Table 5). When CA was combined with VBL and/or CP, IC values were significantly reduced, indicating the potentiation of cancer drugs (Table 5). CA has a better cytotoxicity profile in both aRMS (SJRH30) and eRMS (RD) cell lines. In the eRMS (RD) cell line, $IC_{50}$, $IC_{75}$ and $IC_{90}$ values for CA were 7.5, 16 and 19.5 µg/ml, respectively (Table 5). While $IC_{90}$ values could not be achieved with VBL, CP or VBL+CP combination, CA, VBL+CA and VBL+CP+CA treatments achieved $IC_{90}$ level cytotoxicity in both RD and SJRH30 cell lines. In the eRMS cell line (RD), the dose modification factor (DMF) values for CA are 1.08 and 20 at $IC_{75}$ and $IC_{90}$ levels, respectively, for the VBL+CA combination. Similarly, for the VBL+CP+CA combination, DMF values were 2.75, 40 and >3000 at $IC_{50}$, $IC_{75}$ and $IC_{90}$ levels, respectively. These values indicate the potency of CA in the combination, thereby enabling the dose reduction of harmful cancer drugs in the combination treatment.

In the aRMS (SJRH30), CA has a DMF of 23.75 for the VBL+CA combination at $IC_{50}$ level, 150 at $IC_{75}$ level and >250 at $IC_{90}$ level. In the triple combination of VBL+CP+CA, DMF values were 17.27 at $IC_{50}$, 800 at $IC_{75}$ and 1650 at $IC_{90}$ level. The CP+CA and VBL+CA combinations were better than the VBL+CP combination in terms of cytotoxic effects. The triple combination VBL+CP+CA appeared to be the most effective, suggesting the potential for reducing the doses of cancer drugs like VBL and CP in a clinical setting.

Example 8

Interaction Between CA and Cancer Drugs on RMS Cells

CompuSyn analysis of cytotoxicity estimates clearly indicated the synergism between VBL+CA, CP+CA and among all three of them in a triple combination in both eRMS (RD) and aRMS (SJRH30) cell lines (Table 6 and FIGS. 18A-D). In the eRMS cell line, CI values were less than 1 indicating the synergism between CA and VBL or CP. The dose-effect and medium-effect plots as well as the CI values indicated the potentiation of VBL and CP by CA and the level of synergism at fraction affected levels. There is strong and very strong levels of synergism at $IC_{75}$ level and $IC_{90}$, respectively, in the eRMS cell line (RD). In the aRMS cell line (SJRH30) synergistic effects were noticed for VBL+CA, CP+CA and VBL+CP+CA combinations (Table 6; FIG. 18A-D). These results indicated that CA can be combined with CP and/or VBL for higher therapeutic efficiency.

Example 9

Apoptosis and Caspase 3 Activity

Figures 19A, 19B:
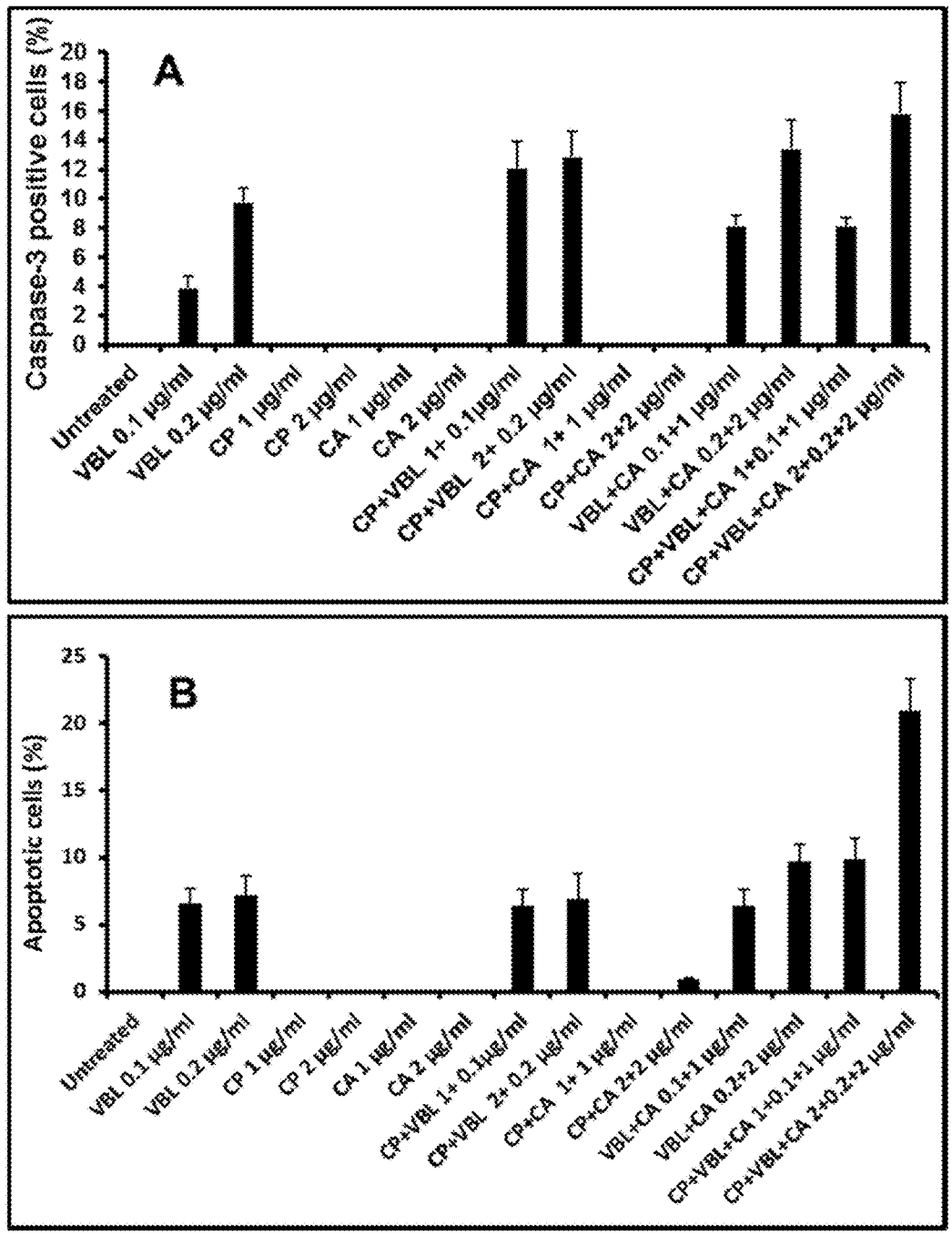
FIGS. 19A-19B: Modulation of caspase-3 activity by vinblastine (VBL), cyclophosphamide (CP), lower doses of C. amada supercritical extract (CA) and their combinations in SJRH30 cell line (FIG. 19A); and induction of apoptosis by vinblastine (VBL), cyclophosphamide (CP), lower doses of C. amada supercritical extract (CA) and their combinations in SJRH30 cell line (FIG. 19B).

The level of caspase activation with VBL, CP, CA and their combinations in SJRH30 (aRMS) is given in FIG. 19A. CA, at very low concentrations of 1 and 2 µg/ml, induces no caspase 3 activity in aRMS cell line and a very low caspase 3 activity in eRMS cell lines. However, when 1 and 2 µg/ml CA is combined with VBL or VBL+CP, a significant increase in caspase 3 activation could be detected. The induction of apoptosis also followed a similar pattern to caspase 3 activity (FIG. 19B). Similar trends on caspase 3 activity and apoptosis were also observed in eRMS cell line treated with CA and its combinations (data not shown). Low concentrations of CA (1 and 2 µg/ml) induced very little apoptosis in both aRMS and eRMS cell lines; however, when low doses of CA were combined with VBL and CP, the level of apoptosis increased substantially. This may explain the increased cytotoxicity of combination than single drugs.

Example 10

Effect of CA on Gene Expression in RD and SJRH30 Cell Lines

Figures 20A, 20B:
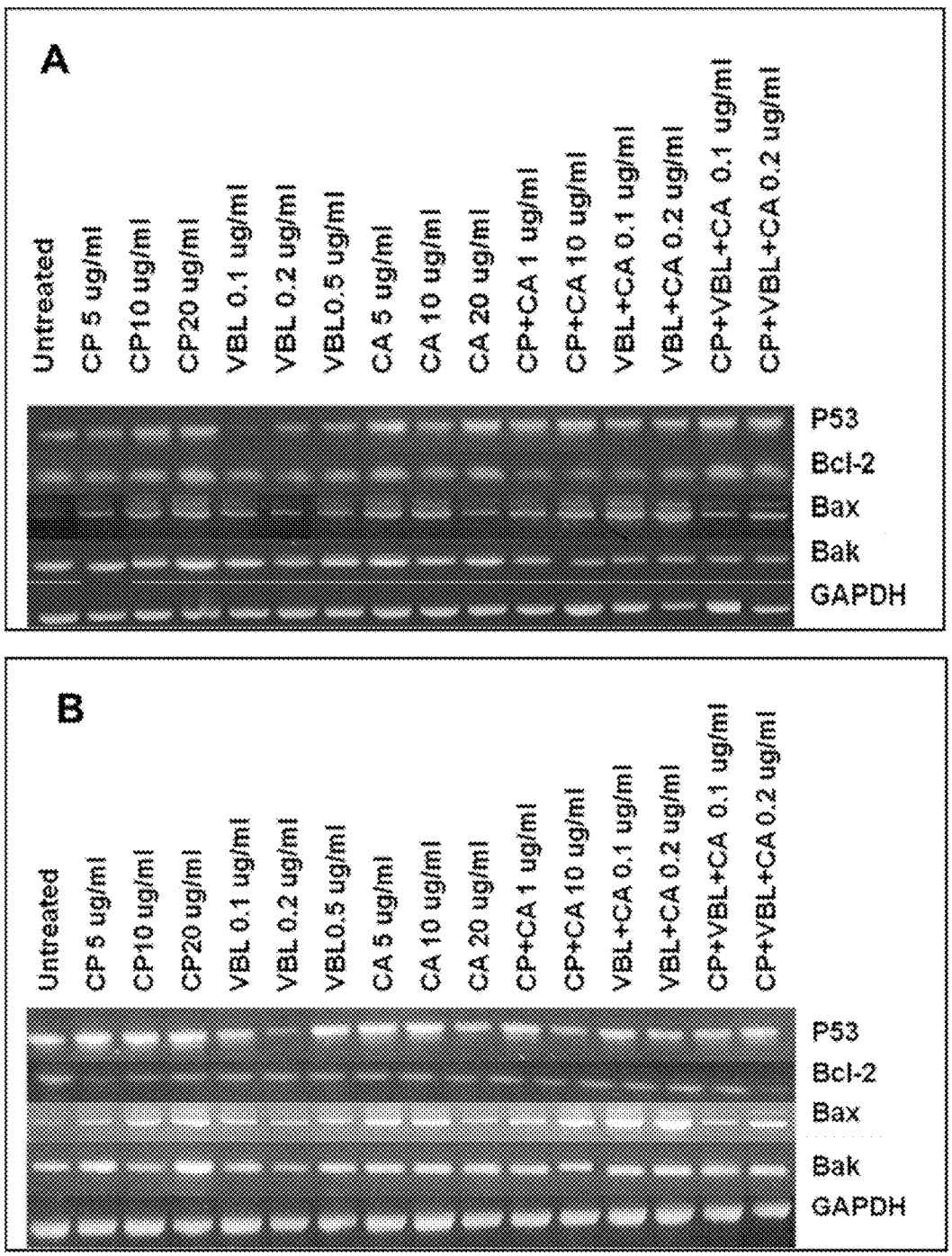
FIGS. 20A-20B: Gene expression analysis of apoptotic genes (p53, Bcl-2, Bax and Bak) by RT-PCR in eRMS RD (FIG. 20A) and aRMS SJRH30 (FIG. 20B) cells treated with VBL, CP, CA and their combinations. Total RNA was extracted from cells treated with drugs and their combinations for 72 h and RT-PCR assay performed with 5 μg of RNA using gene specific primers. The house keeping gene GAPDH is also amplified as control.
Figures 21A, 21B:
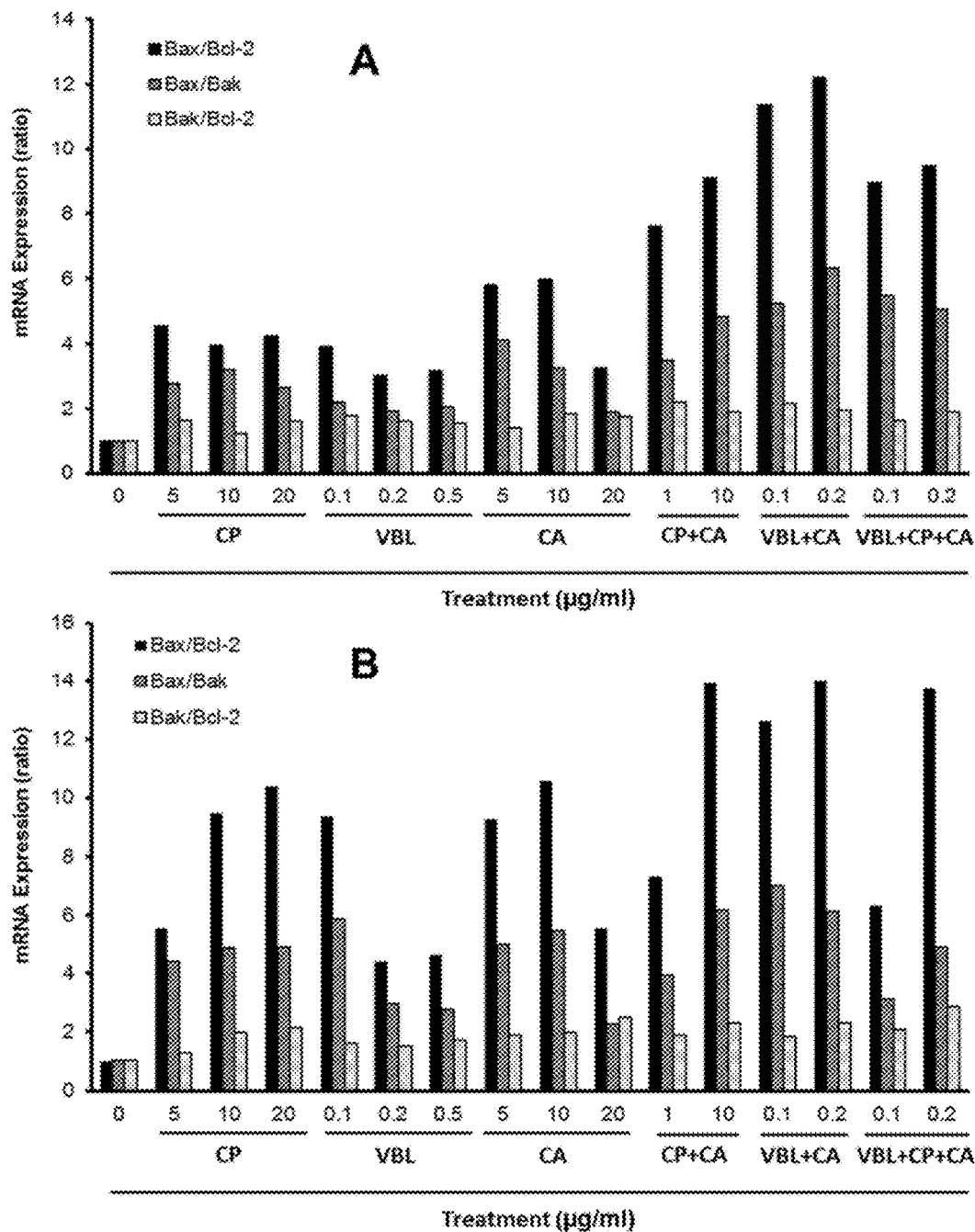
FIGS. 21A-21B: The ratios of Bax/Bcl-2, Bax/Bak and Bak/Bcl-2 expression induced by VBL, CP, CA and their combinations in RD eRMS (FIG. 21A) and SJRH30 aRMS (FIG. 21B) cell lines. The ratios indicated increase with drug treatment.
Figure 22:
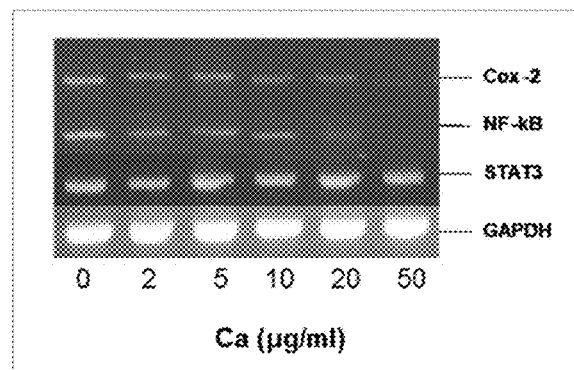
FIG. 22: RT-PCR assay for gene expression analysis of inflammatory genes (COX-2, NF-kB and STAT3) in SJRH30 cells treated with increasing concentrations of CA. GAPDH is also amplified as a control.

The expression of p53, Bax, Bcl-2 and Bak genes as well as the housekeeping GAPDH gene in RD and SJRH30 cell lines treated with different drugs/combinations are given in FIGS. 20A-B. The treatment of cells with CP, VBL, CA or their combination have induced an increase in the expression of p53, Bax and Bak and a decrease in the expression of Bcl-2. The ratios of Bax/Bcl-2, Bax/Bak and Bak/Bcl-2 expression demonstrated an increase with combination treatment (FIGS. 20A-B). While the Bax/Bcl-2 ratio showed the largest increase, Bak/Bcl-2 ratio showed the smallest increase.

The expression of genes associated with inflammation is also inhibited by CA treatment in aRMS cells. While a dose-dependent inhibition of COX-2 and NF-kB expression was evident (FIGS. 22 and 23A-D), no change in the expression of STAT3 was noticed with CA treatment.

Example 11

Rhabdomyosarcoma Xenograft Studies

Figure 25:
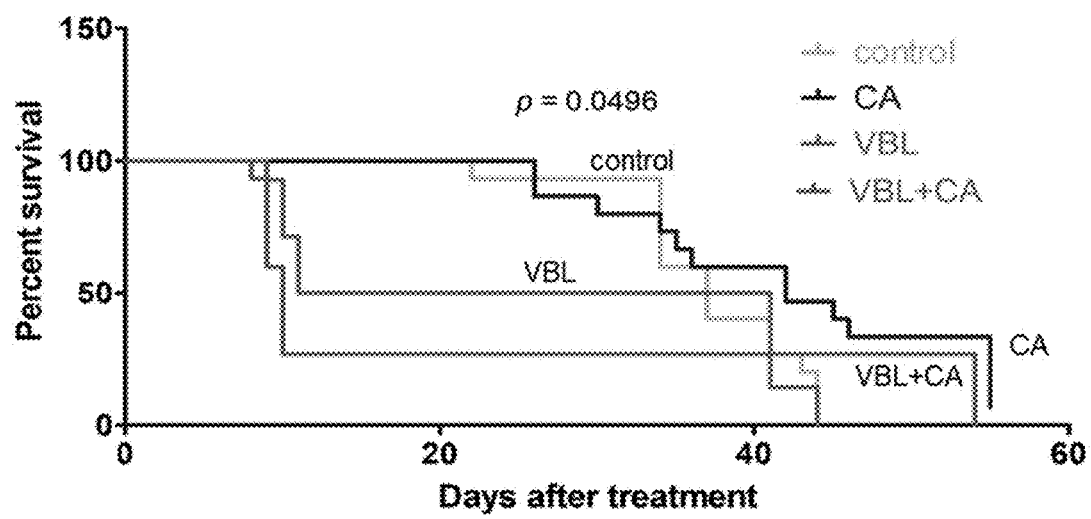
FIG. 25: Kaplan-Meier survival curve analysis of aRMS (SJRH30) nude mice xenografts treated with saline control, VBL, CA and VBL+CA. The difference between treatment groups are significant (*$p<0.05$).
Figures 23A, 23B, 23C, 23D:
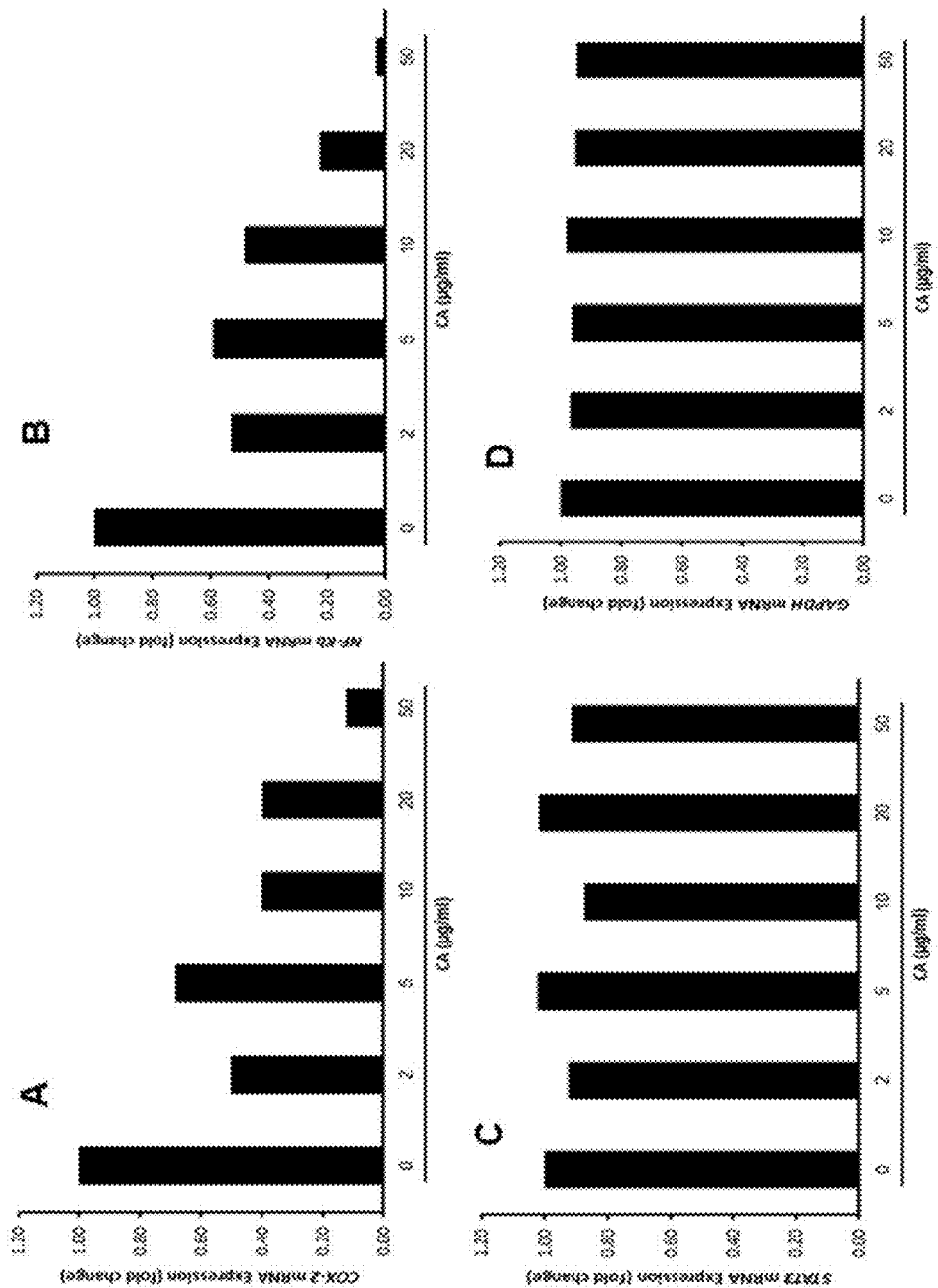
FIGS. 23A-23D: Quantification of gene expression associated with inflammation (COX-2, NF-kB and STAT3) induced by CA in SJRH30 aRMS cell line. The RT-PCR gels were scanned and quantified using UNSCAN-IT-gel version 6.1 program. The relative changes in fold levels are plotted against concentrations of drug and/or combinations.
Figure 24:
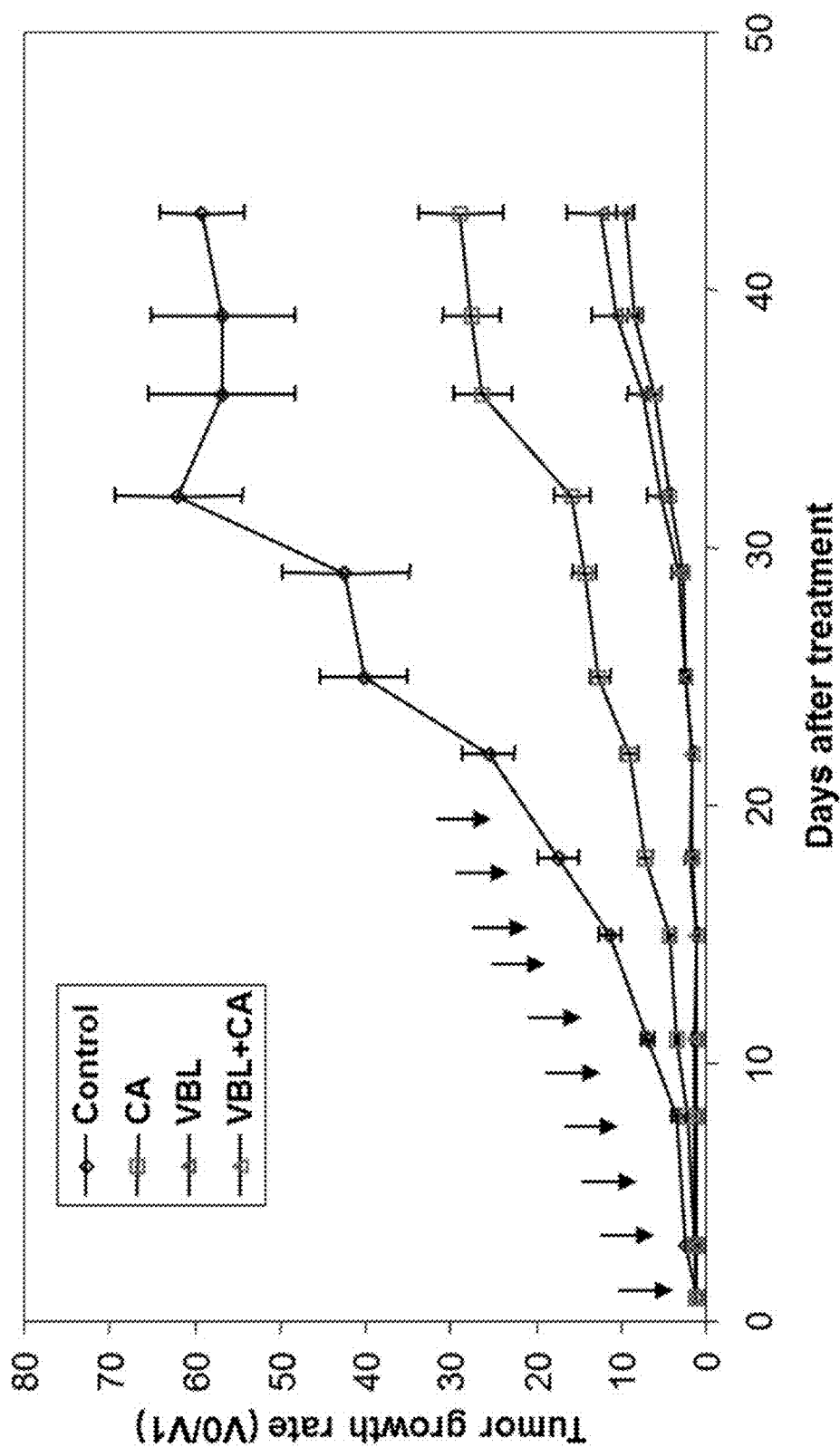
FIG. 24: Inhibition of tumor growth rate in SJRH30 xenografts treated with saline (control), VBL, CA, and VBL+CA combination. Xenografts (n=20) were administered intraperitoneally with saline (control) or VBL (2 mg/kg), whereas CA (10 mg/kg) was given daily through drinking water. Tumor measurements are recorded twice and mean±SD estimates of tumor growth rate are plotted against days after treatment. The arrow in the graph represents the day of VBL administration. The treatment groups were compared with one-way ANOVA with Dunnett's multiple comparison test. (***$p<0.001$).

The average tumor growth rates of aRMS nude mice xenografts in different treatment groups are presented in FIG. 24. Tumor growth rate increased steadily for the control group until day 33 when it showed a plateauing trend. Tumor growth rate was significantly inhibited in the CA, VBL and VBL+CA groups when compared to the control group (***p<0.001 by ANOVA). CA treatment alone inhibited the tumor growth rate significantly compared to the control group, and VBL+CA combination was still better than CA alone on tumor growth rate inhibition. Even though VBL+CA group was better than VBL, the difference was not significant. Kaplan Meier analysis of survival data (FIG. 25) showed that CA-treated aRMS xenografts survived better than the VBL and VBL+CA treated groups (p=0.0496). Also, there was no apparent difference in the weight gain of xenografts between treatment groups and all treatment groups have almost similar overall increase in weight (data not shown), indicating the absence of any overall weight loss due to CA, VBL or VBL+CA treatment.

Materials and Methods for Examples 12-15

Cell line and Cell Culture.

Human glioblastoma cell line (U-87MG) was purchased from American Type Culture Collection, Manassas, Va. and the cells were grown in RPMI medium supplemented with 10% FBS and antibiotics in a humidified 5% $CO_2$ incubator. Normal mouse embryonic hypothalamus cell line (mHypoE-N1) was purchased from CELLutions Biosystems, Inc, Burlington, Ontario, Canada and was grown in DMEM, supplemented with 10% FBS and antibiotics in the $CO_2$ incubator.

*Curcuma amada* Extract and Other Agents.

Supercritical $CO_2$ extract of *Curcuma amada*, was prepared by Flavex Naturextrakte GmbH, Rehlingen, Germany. The usual yield of extract was 2.5-3% of dried rhizome. The product has the form of a brownish extract and contains 10.2% of steam volatile components. Quantitative analysis by HPLC and GC-MS showed the presence of 61.7% (E)-labda-8(17),12diene-15,16 dial (LDD), 5.6% beta myrcene, 0.8% beta pinene, 0.3% ocimene, 0.2% beta cariophyllene besides other essential oil trace components. Temozolomide, etoposide and curcumin were purchased from Sigma-Aldrich, St. Louis, Mo. and Turmeric Force was purchased from New Chapter Inc. VT.

Tumor Cell Transendothelial Migration Assay.

In order for tumor cells to migrate from a primary tumor mass to distant locations, they must invade through the basal membrane and into blood vessels (intravasation), circulate in the blood stream, survive during transport, then migrate out of a blood vessel (extravasation) to establish micrometases. The penetration of circulating tumor cells into the endothelium is a crucial step for tumor metastases. The calorimetri QCM tumor cell trans-endothelial cell migration assay kit (Millipore) was used to analyze the ability of tumor cells to invade the endothelium. To perform this assay, human vascular endothelial cells (HUVEC) cells ($10^5$/250 µl well of F15 medium supplemented with FBS and antibiotics) were plated in each Boydon chambers and allowed to grow for 72 hours in the CO2 incubator until the endothelial cells formed a monolayer. The endothelial cells were activated with 20 ng/ml recombinant human TNFα for 18 hours by incubating in a $CO_2$ incubator at 37° C. On the fifth day, U-87MG tumor cells were harvested and re-suspended in serum-free RPMI medium containing only 0.5% FBS. The medium was removed from HUVEC cells growing in Boydon chambers and tumor cells (105/well in 0.25 ml of serum free medium) were added into the Boydon chambers. The insert chambers were then transferred to wells containing 300 ul of serum free RPMI medium. Once the cells were settled (after 1 hour) both insert chambers and wells containing serum free medium were treated with increasing concentrations of CA (0-20 µg/ml). The multi-well plate containing HUVEC+U-87MG cells was incubated in a $CO_2$ incubator at 37° C. for 24 hours. The invasion of tumor cells across the endothelium is determined by measuring the number of cells that migrate to the lower chamber. The inner plate is stained with cell stain solution for 15 minutes, washed the excess stain with distilled water and stain was extracted from migrated tumor cells using 200 μl of stain extraction solution. The absorbance of the extracted stain was measured at 50 nm in a plate reader and the inhibition (%) of tumor cell migration by CA was estimated as compared to the untreated control sample.

Akt Phosphorylation.

U-87MG glioblastoma cells (2×106/5 ml) was treated with increasing concentrations of CA (0-100 μg/ml) for 72 hours and total cellular proteins were isolated using lysis buffer from the Cell Signaling Technology, Inc., Danvers, Mass. The concentrations of protein in the lysate were estimated by the Lowrie's method. The phosphorylated form of Akt in the cellular lysate equivalent to 10 ug protein was analyzed using the Surveyor IC human phospho-Akt Pan Specific ELISA kit according to manufacturer's instructions. (R&D Systems, Minneapolis, Minn.). The relative phospho-Akt levels of U-87MG cells under increasing concentrations of CA were plotted.

AMPK Alpha Phosphorylation.

U-87MG glioblastoma cells were treated with increasing concentrations of CA for 72 hours and total cellular proteins were isolated using lysis buffer (Cell Signaling Technology, Inc., Danvers, Mass.). Cellular extract equivalent to 10 μg protein was analyzed for the phosphorylated form of AMPKα using the PathScan Phospho-AMPKα Sandwich ELISA kit from Cell Signaling Technology, Inc., according to the manufacturer's instructions. The changes in modulation of phosphorylated form of AMPKα (%) as compared to untreated control sample were plotted against CA concentrations.

Gene Expression Studies by RT-PCR Assay.

The mRNA expression of genes associated with apoptosis (Bax, Bcl-2, p21, p53, caspase3, caspase 9) and cell proliferation (CCNB2, Ki67 and PCNA), angiogenesis (VEGF and VEGFR) and inflammation (COX-2), telomerase activity (hTERT) and oncogenesis (c-myc and N-myc) were analyzed by reverse transcriptase-polymerase chain reaction (RT-PCR) (Hussain et al. 1992). The expression of a housekeeping gene, Glyceraldehyde 3-phosphate dehydrogenase (GAPDH) was used as a control. The expression of genes was quantified using gel pictures by the UNSCAN-IT Gel™ software (Silk Scientific, Inc., Orem, Utah). The relative mRNA expressions (average pixel units) at different CA concentrations were statistically analyzed by 1-way ANOVA and the treatments were compared using Dunnett's multiple comparison tests (GraphPad Prism software, La Jolla, Calif.).

Western Blot Analysis.

U-87MG cells (5×10$^6$/5 ml) were treated with increasing concentration of CA (0-100 μg/ml) for 72 h and total cellular protein was extracted using 0.5 ml of Invitrogen's protein extraction buffer (Invitrogen Corporation, Frederick, Calif.). The protein concentration was determined and 100 μg of protein was separated on 7.5% SDS-PAGE. The separated protein was blotted on a nitrocellulose filter. The filters were hybridized with antihuman monoclonal/polyclonal antibodies specific for each protein (Bax, Bad, Bcl-2, Bcl-X, p21, p53, Caspase 3, phospho-AMPK, VEGF, mTOR, HSP70, HSP90 and β-actin) in a western blot procedure and detected using the Alkaline phosphatase color detection kit (Bio Rad Laboratories, Hercules, Calif.). The relative expression of proteins compared to untreated control samples were quantified using UNSCAN-IT Gel™ software (Silk Scientific, Inc., Orem, Utah). The relative increase or decrease in protein level was calculated based on untreated sample and fold-level changes were plotted against CA concentration.

Statistical Analysis.

Mean and standard deviation estimates were calculated using Microsoft Excel software using data from three separate experiments. The relative mRNA expressions (average pixel units) at different CA concentrations were statistically analyzed by 1-way ANOVA and the treatments were compared using Dunnett's multiple comparison tests (GraphPad Prism software, La Jolla, Calif.).

Example 12

Effect of CA on Human Glioblastoma Cell Migration

Figure 26:
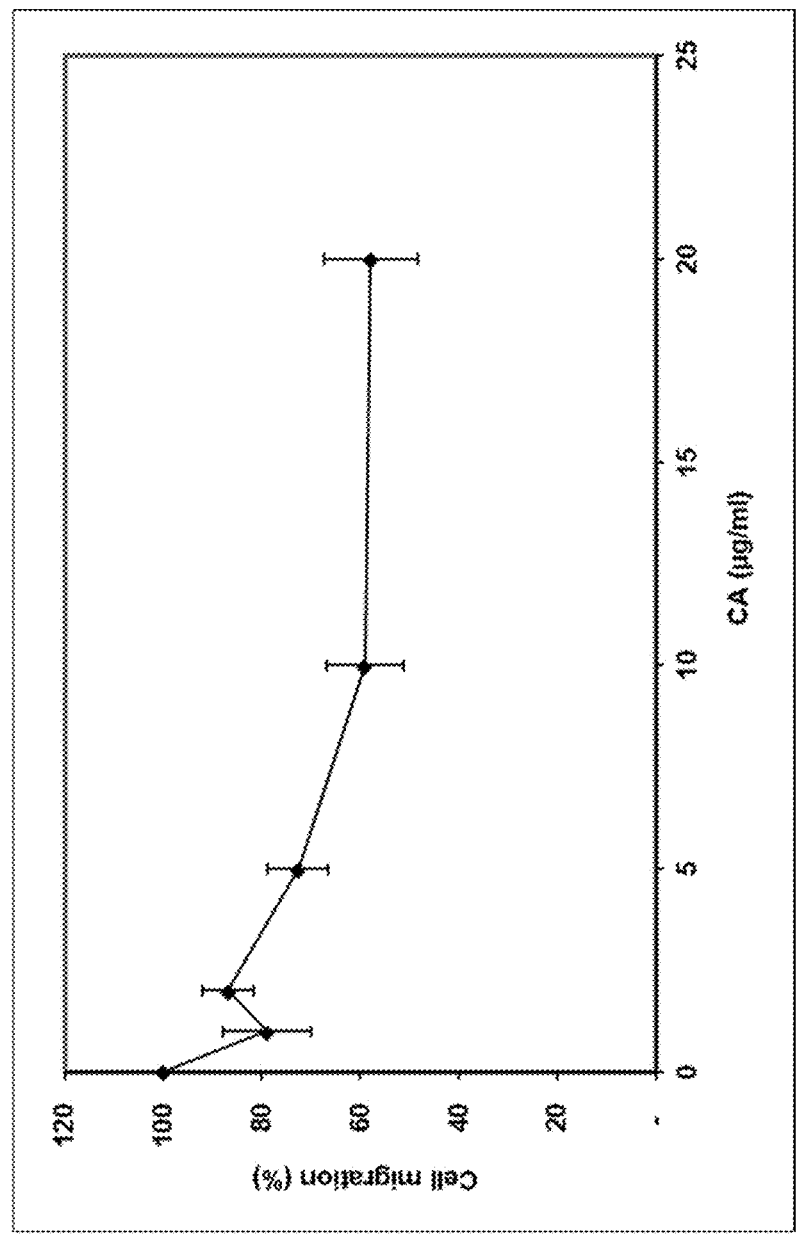
FIG. 26: Inhibition of tumor cell migration by CA in U-87MG cells by CA.

A concentration-dependent inhibition of cell migration of U-87MG tumor cells through endothelial layer was evident with CA treatment of U-87MG tumor cells (FIG. 26). CA treatment reduced cell migration by 43% at 20 μg/ml concentration.

Example 13

Effects of CA on AKT Signaling and AMPKα Phosphorylation

Figure 27:
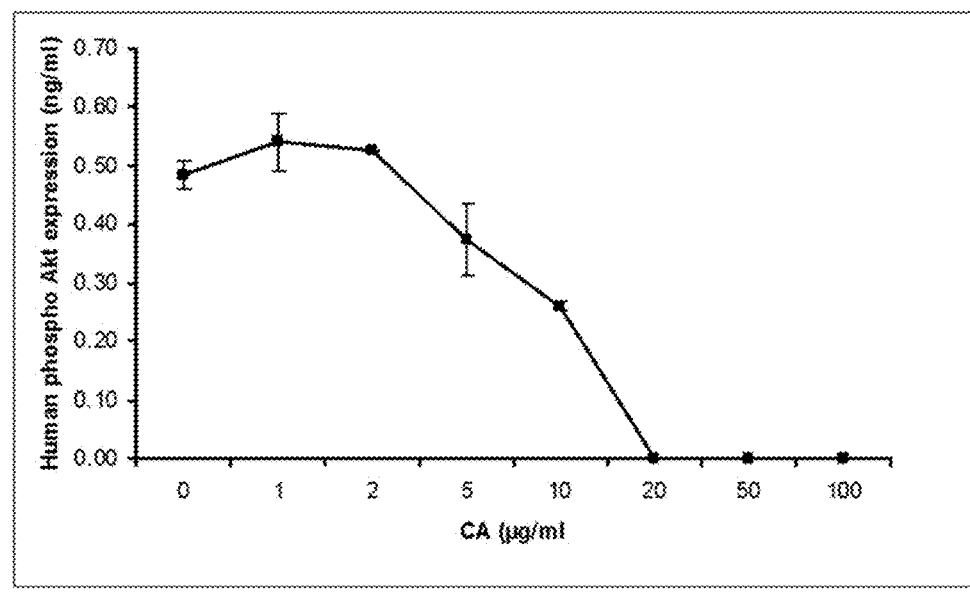
FIG. 27: Inhibition of AKT phosphorylation by CA treatment in U-87MG cells. Phosphorylated form of AKT was analyzed after treating U-87MG cells with CA at 37° C. for 72 hours using Pathscan ELISA kit from Cell Signaling technology

The effect of CA on AKT signaling is presented in FIG. 27. CA has inhibited the phosphorylated form of AKT in a dose-dependent manner with 50% inhibition at 10 ug/ml dose and complete inhibition at 20 ug/ml dose.

Figure 28:
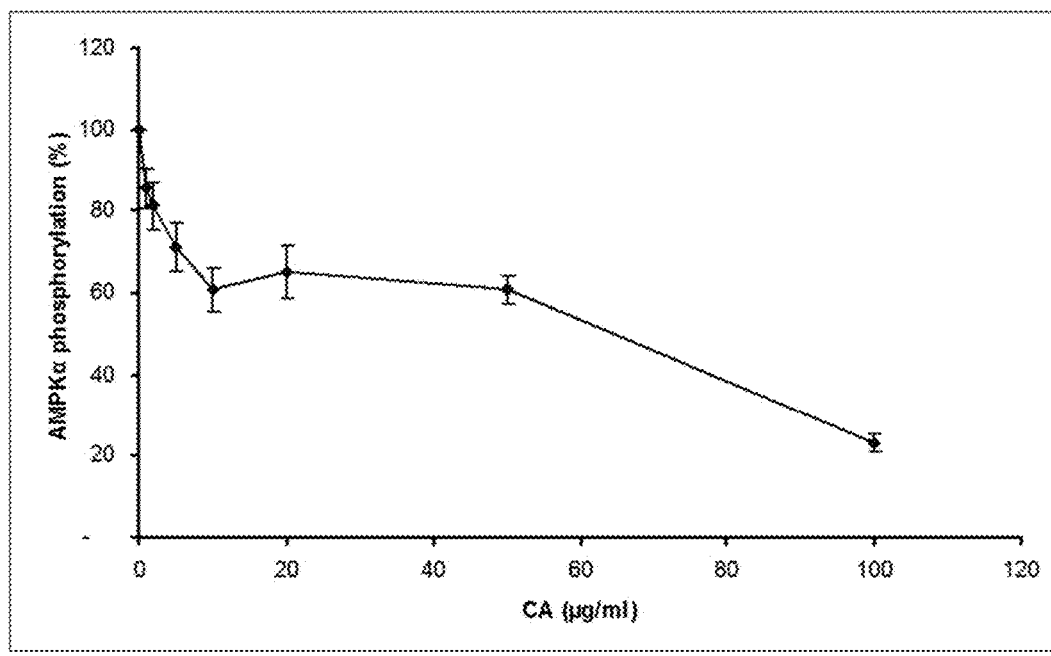
FIG. 28: Effect of CA on phosphorylated form of AMPKα in U-87 cells after treating the U-87MG cells at 37° C. for 72 hours.

A steady decrease in the level of the phosphorylated form of AMPKα was observed with an increase in CA treatment of U-87MG cells. CA inhibited AMPKα phosphorylation about 75% at 100 ug/ml (FIG. 28).

Example 14

Effects of CA on mRNA and Protein Expression

Figure 29:
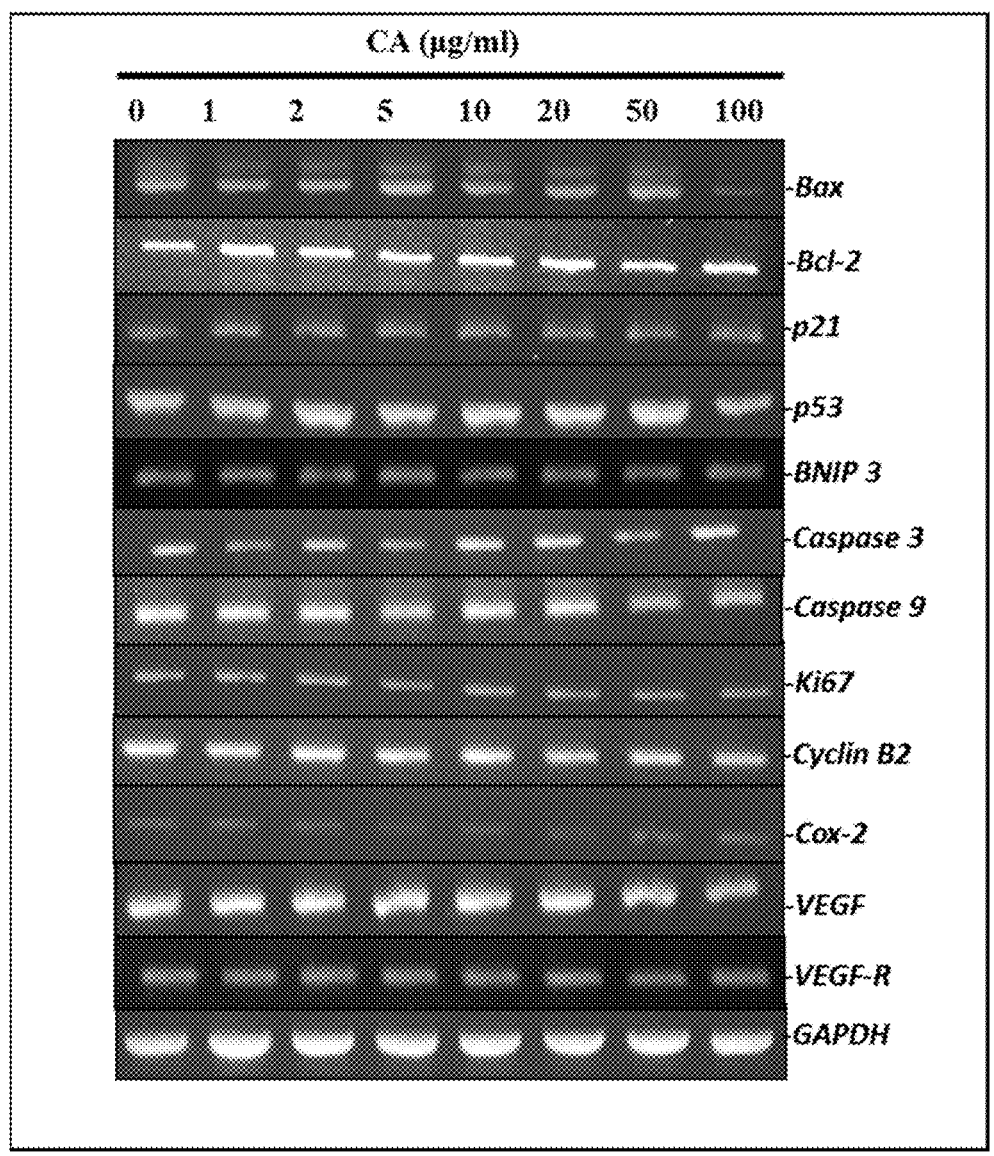
FIG. 29: RT-PCR assay of gene expression associated with apoptotis, cell proliferation, and angiogenesis (Bax, Bcl-2, Bax/Bcl-2 ratio, BNIP3, p21, p53, caspase-3, and caspase-9) along with house keeping gene GAPDH in CA-treated U-87MG cells.
Figures 30A, 30B, 30C, 30D, 30E, 30F, 30G, 30H, 30I:
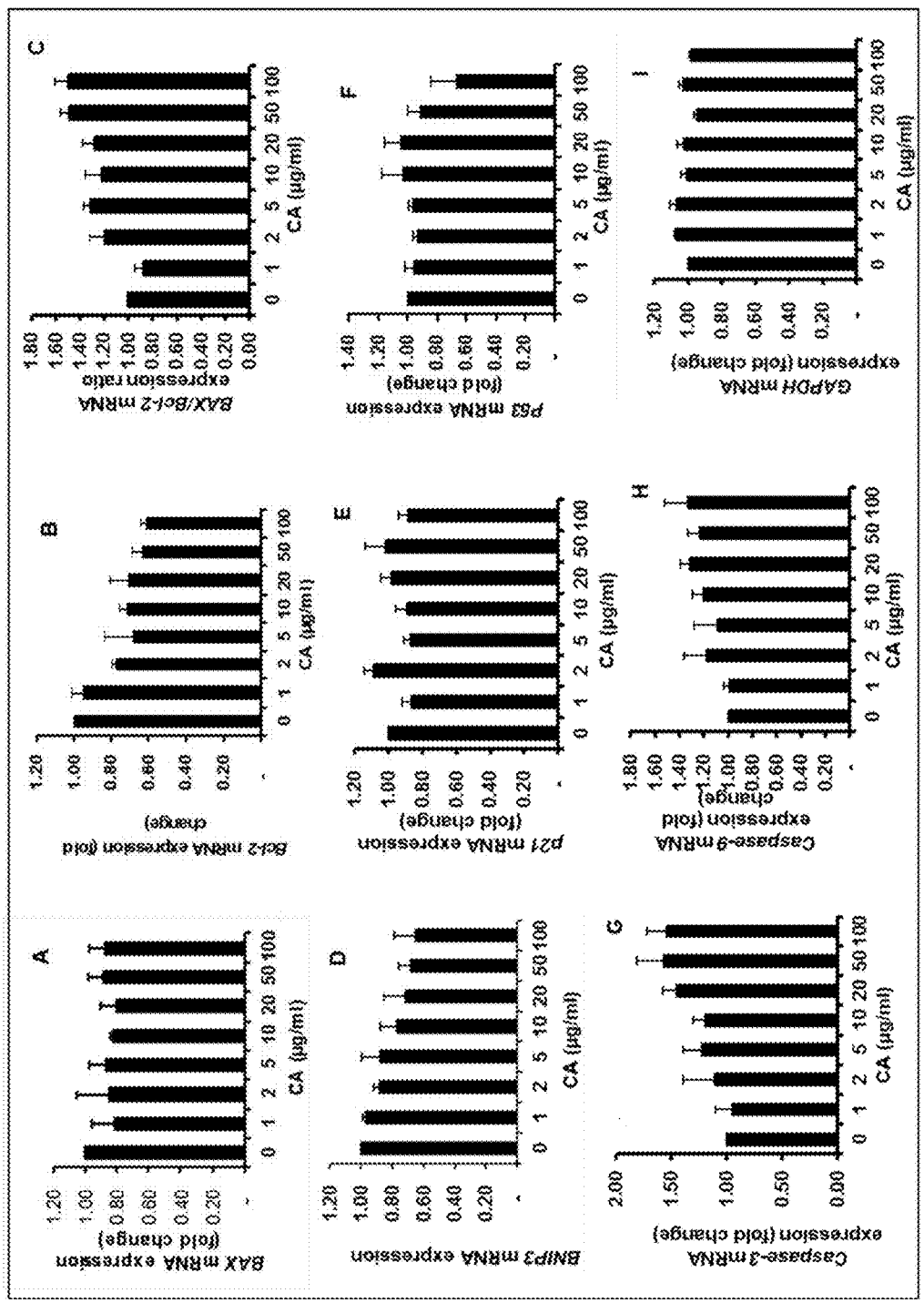
FIGS. 30A-30I: Quantification of expression of apoptotic genes by UNSCAN-IT gel software. The relative expression of genes (fold changes in the expression compared to untreated control samples) as well as Bax/Bcl-2 ratio is plotted against CA concentrations.
Figures 31A, 31B, 31C, 31D:
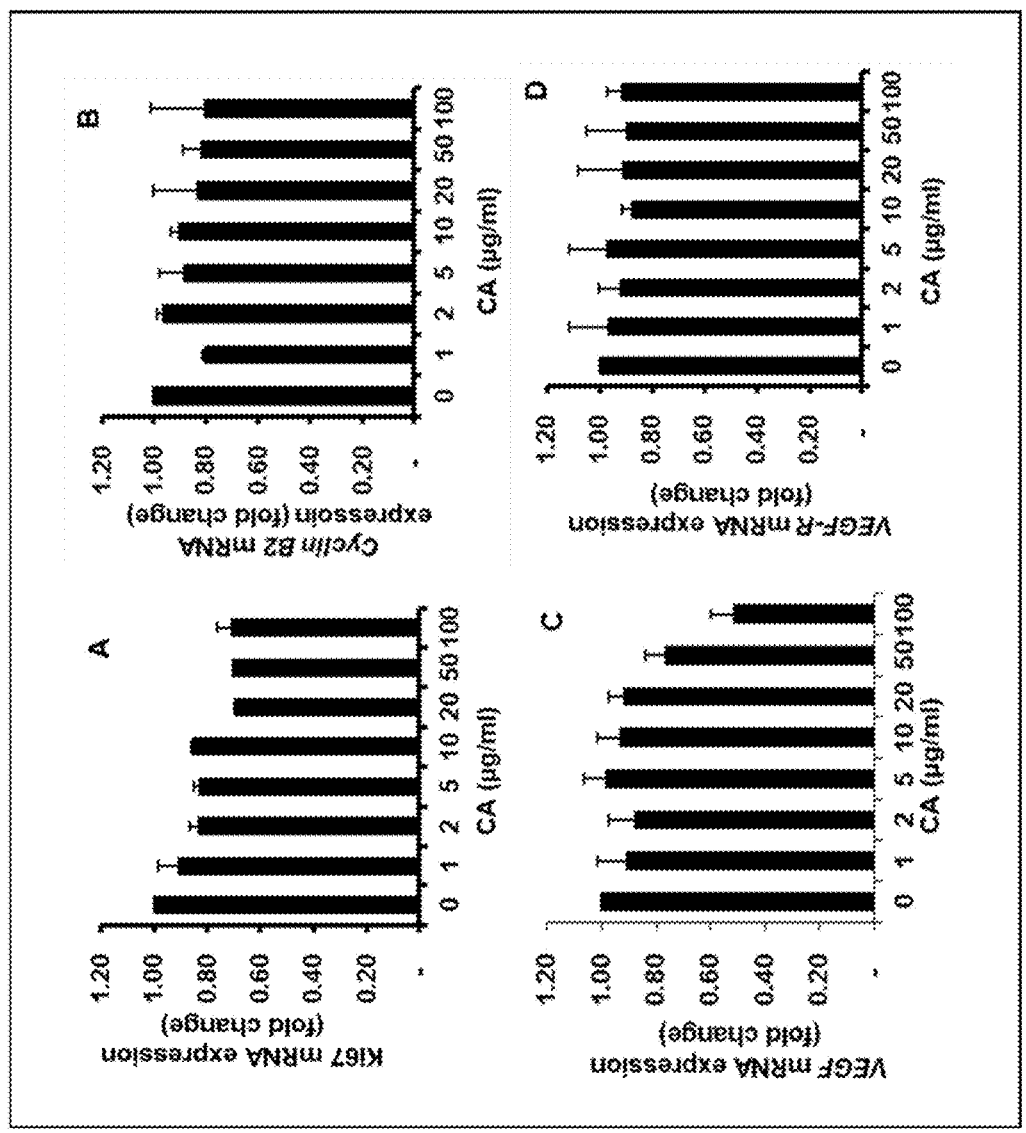
FIGS. 31A-31D: Quantification of expression of cell proliferation (Ki67, Cyclin B2) and angiogenesis (VEGF, VEGF-R1) genes in U-87MG cells treated with CA.

The results of RT-PCR assay of mRNA analysis are shown in FIG. 29 and the quantification is provided in FIGS. 30A-I and FIGS. 31A-D. The genes associated with the AKT signaling pathway and cellular processes such as apoptosis, cell proliferation, and oncogenesis were analyzed. Although there was no apparent change in the level of BAX mRNA, Bcl-2 mRNA showed a dose-dependent decrease of up to 40% with increasing CA concentrations. Also the ratio of BAX/Bcl-2 showed dose-dependent increase with CA treatment of U-87MG cells. The Bcl-2/EIB 19 kDa-interacting protein 3 (BNIP3) mRNA also showed a dose-dependent decrease with about 35% drop at 100 μg/ml CA concentration. While p21 mRNA showed no apparent change, p53 mRNA decreased 35% at 100 μg/ml CA concentration. Among the down-stream genes associated with apoptosis, caspase-3 showed a dose-dependent increase with 54% increase in mRNA level at 100 μg/ml CA concentration. On the other hand, caspase-9, another downstream pro-apoptotic biomarker showed a dose-dependent increase in mRNA expression with increasing CA concentration, reaching about 33% increase in caspase-9 mRNA at 100 ug/ml CA. Among the two genes associated with cell proliferation (Ki67 and CCNB2), CA down-regulated the expression of Ki67 steadily with about 30% decrease at the highest CA concentration, whereas CCNB2 (cyclin B2) mRNA level remained same with CA treatment. Two genes associated with angiogenesis (VEGF and VEGF-receptor 1) were analyzed in U-87MG cells treated with increase in CA concentrations; while VEGF-receptor 1 mRNA synthesis was not affected by CA, VEGF mRNA showed a decrease at 50 and 100 μg/ml concentrations.

Figure 32:
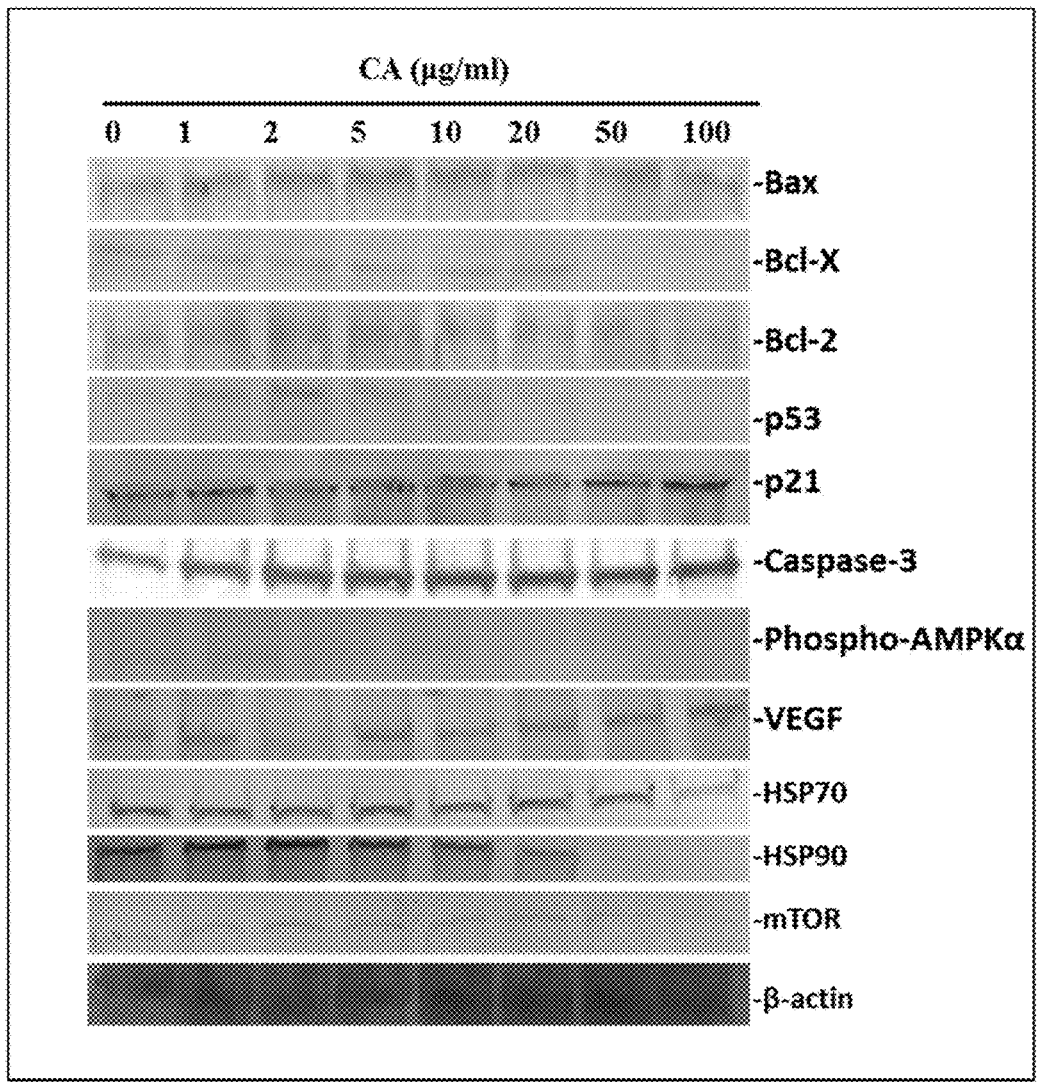
FIG. 32: Western blot analysis of apoptotic proteins (Bax, Bak, Bad, Bcl-2, Bcl-X, p53 and Caspase 3). Total proteins (100 µg) were separated on 7.5% polyacrylamide gels, transferred to nitrocellulose filter, hybridized with gene specific antibodies and detected using Bio-Rad Horseradish peroxidase or Alkaline phosphatase coloring reagent.
Figure 33:
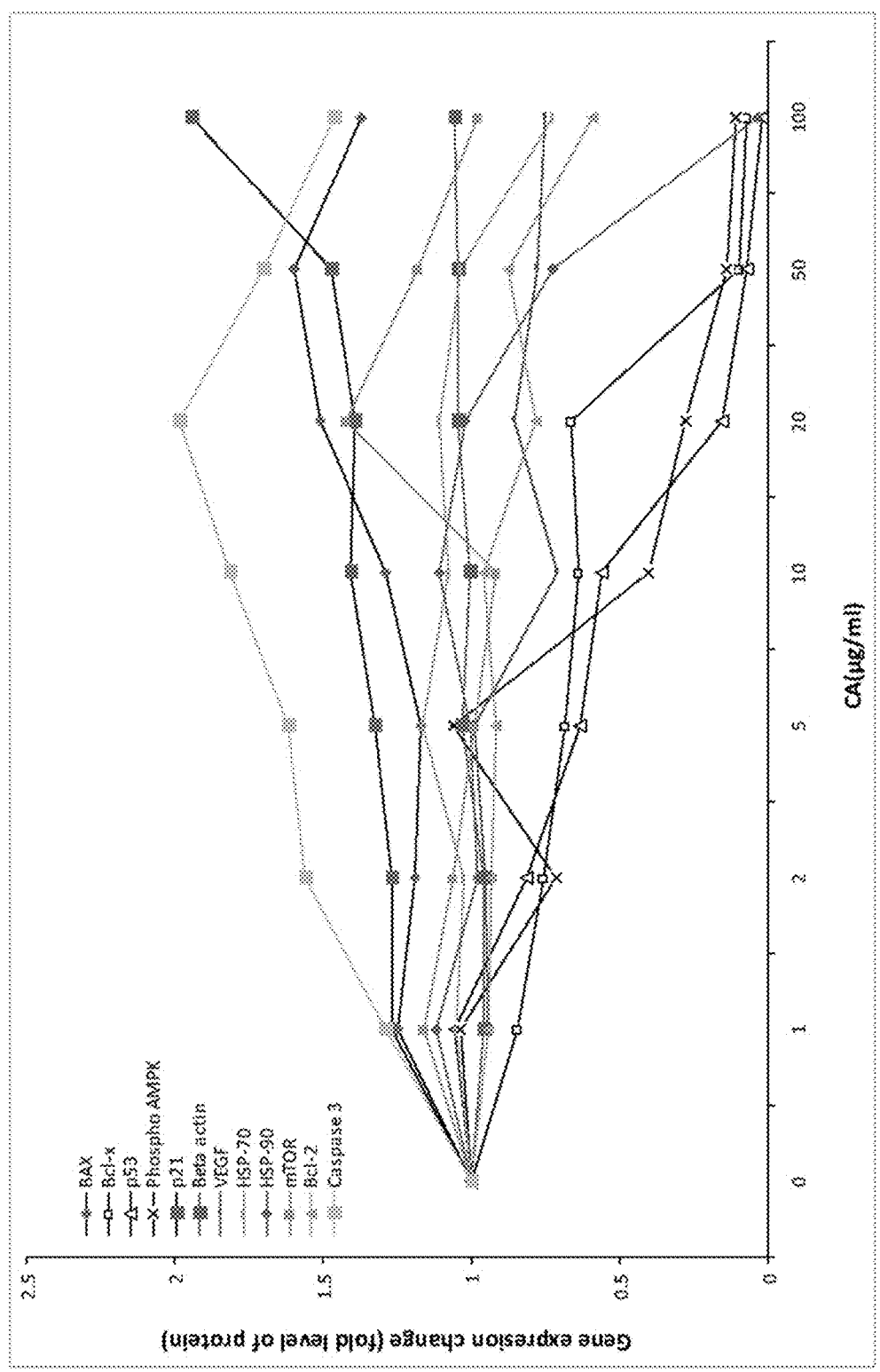
FIG. 33: Quantification of protein expression associated with apoptosis by UNSCAN-IT gel software. The relative protein expression (fold change based on untreated control) was plotted against CA concentrations.

The results of Western blot analysis are shown in FIG. 32 and quantification of expression levels are shown in FIG. 33. The pro-apoptotic genes such as caspase 3, Bax and p21 were up regulated by CA, all showing more than 50% increase with increasing CA concentrations. However, the expression of genes such as HSP70 and mTOR was not changed very much with CA treatment. On the other hand, anti-apoptotic genes like Bcl-X, mutant p53, BNIP3, and Bcl-2 were down regulated. The VEGF expression showed a small down regulation at higher concentrations of CA which corresponds with mRNA expression pattern. In addition, the expression of HSP90 which follows downstream in the AKT signaling pathway, and the phosphorylated form of AMPKα were down regulated with CA treatment. CA's anti-aging properties may in part be attributed to the inhibition of mTOR activity demonstrated in FIGS. 32 and 33.

Example 15

Effect of CA on ATP Synthesis

Figure 34:
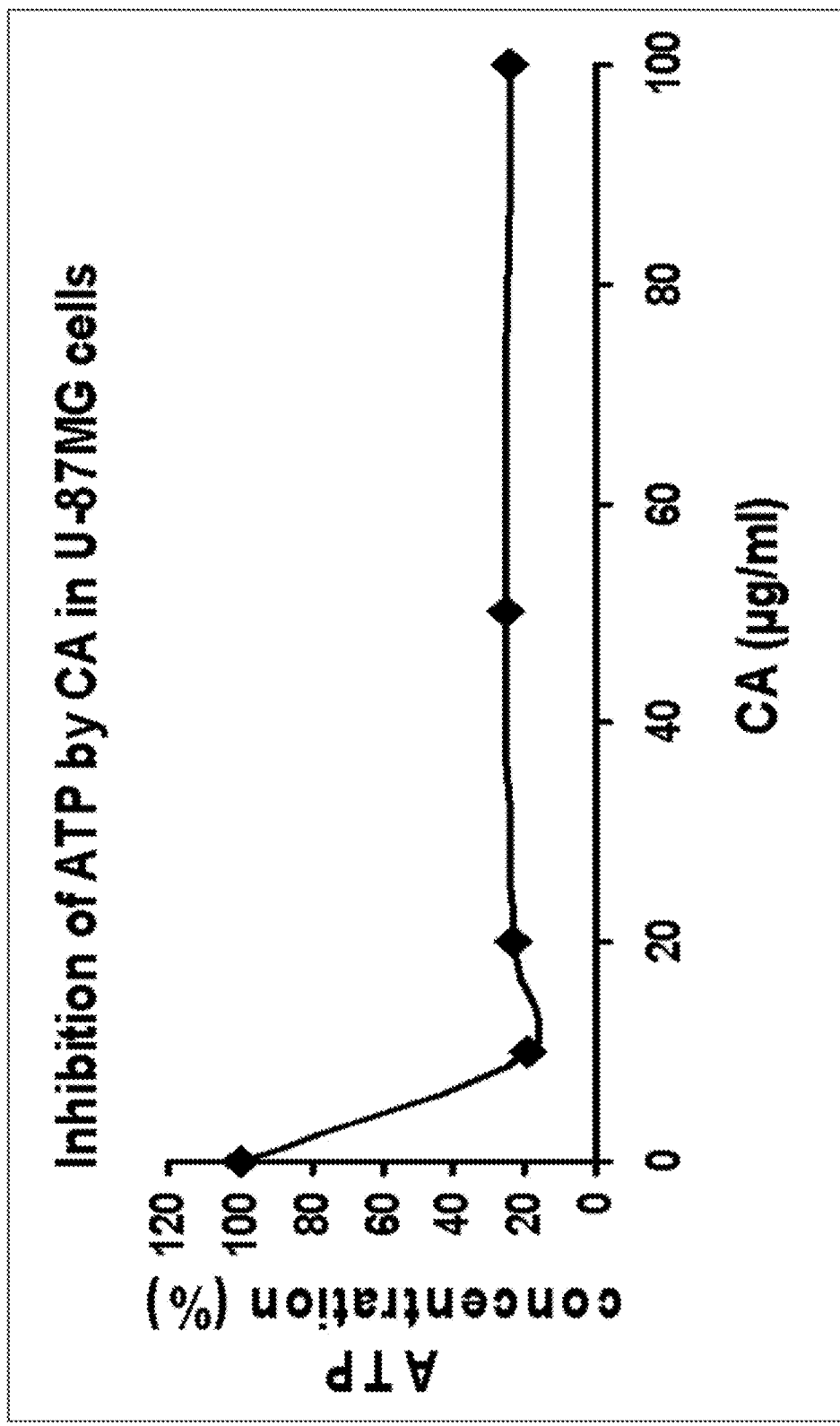
FIG. 34: Quantification of % adenosine-5'-triphosphate (ATP) in U-87MG cells plotted against CA concentrations. CA significantly inhibits ATP synthesis in tumor cells.

The effect of CA on adenosine-5'-triphosphate (ATP) synthesis in U-87MG tumor cells was determined. % ATP concentration is shown plotted against CA concentrations in FIG. 34. CA significantly inhibited ATP synthesis in the tumor cells (by 80%) beginning with a dose escalation of less than 20 μg/ml).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | Hepatocellular (Liver) Cancer, Childhood |
| Acute Myeloid Leukemia, Childhood | (Primary) |
| Adrenocortical Carcinoma | Hodgkin's Lymphoma, Adult |
| Adrenocortical Carcinoma, Childhood | Hodgkin's Lymphoma, Childhood |
| AIDS-Related Cancers | Hodgkin's Lymphoma During Pregnancy |
| AIDS-Related Lymphoma | Hypopharyngeal Cancer |
| Anal Cancer | Hypothalamic and Visual Pathway Glioma, |
| Astrocytoma, Childhood Cerebellar | Childhood |
| Astrocytoma, Childhood Cerebral | Intraocular Melanoma |
| Basal Cell Carcinoma | Islet Cell Carcinoma (Endocrine Pancreas) |
| Bile Duct Cancer, Extrahepatic | Kaposi's Sarcoma |
| Bladder Cancer | Kidney (Renal Cell) Cancer |
| Bladder Cancer, Childhood | Kidney Cancer, Childhood |
| Bone Cancer, Osteosarcoma/Malignant Fibrous Histiocytoma | Laryngeal Cancer |
| | Laryngeal Cancer, Childhood |
| Brain Stem Glioma, Childhood | Leukemia, Acute Lymphoblastic, Adult |
| Brain Tumor, Adult | Leukemia, Acute Lymphoblastic, Childhood |
| Brain Tumor, Brain Stem Glioma, Childhood | Leukemia, Acute Myeloid, Adult |
| | Leukemia, Acute Myeloid, Childhood |
| Brain Tumor, Cerebellar Astrocytoma, Childhood | Leukemia, Chronic Lymphocytic |
| | Leukemia, Chronic Myelogenous |
| Brain Tumor, Cerebral Astrocytoma/Malignant Glioma, Childhood | Leukemia, Hairy Cell |
| | Lip and Oral Cavity Cancer |
| | Liver Cancer, Adult (Primary) |
| Brain Tumor, Ependymoma, Childhood | Liver Cancer, Childhood (Primary) |
| Brain Tumor, Medulloblastoma, Childhood | Lung Cancer, Non-Small Cell |
| | Lung Cancer, Small Cell |
| Brain Tumor, Supratentorial Primitive Neuroectodermal Tumors, Childhood | Lymphoma, AIDS-Related |
| | Lymphoma, Burkitt's |
| Brain Tumor, Visual Pathway and Hypothalamic Glioma, Childhood | Lymphoma, Cutaneous T-Cell, see Mycosis Fungoides and Sézary Syndrome |
| Brain Tumor, Childhood | Lymphoma, Hodgkin's, Adult |
| Breast Cancer | Lymphoma, Hodgkin's, Childhood |
| Breast Cancer, Childhood | Lymphoma, Hodgkin's During Pregnancy |
| Breast Cancer, Male | Lymphoma, Non-Hodgkin's, Adult |
| Bronchial Adenomas/Carcinoids, Childhood | Lymphoma, Non-Hodgkin's, Childhood |
| | Lymphoma, Non-Hodgkin's During Pregnancy |
| Burkitt's Lymphoma | Lymphoma, Primary Central Nervous System |
| Carcinoid Tumor, Childhood | Macroglobulinemia, Waldenström's |
| Carcinoid Tumor, Gastrointestinal | Malignant Fibrous Histiocytoma of |
| Carcinoma of Unknown Primary | Bone/Osteosarcoma |
| Central Nervous System Lymphoma, Primary | Medulloblastoma, Childhood |
| | Melanoma |
| Cerebellar Astrocytoma, Childhood | Melanoma, Intraocular (Eye) |
| Cerebral Astrocytoma/Malignant Glioma, Childhood | Merkel Cell Carcinoma |
| | Mesothelioma, Adult Malignant |

TABLE 1-continued

Examples of Cancer Types

Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see
Mycosis Fungoides and Sézary
Syndrome
Endometrial Cancer
Ependymoma, Childhood
Esophageal Cancer
Esophageal Cancer, Childhood
Ewing's Family of Tumors
Extracranial Germ Cell Tumor,
Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial,
Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral
Astrocytoma
Glioma, Childhood Visual Pathway and
Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin
Cancer (non-Melanoma)
Squamous Neck Cancer with Occult
Primary, Metastatic
Stomach (Gastric) Cancer
Stomach (Gastric) Cancer, Childhood
Supratentorial Primitive
Neuroectodermal Tumors, Childhood
T-Cell Lymphoma, Cutaneous, see
Mycosis Fungoides and Sézary
Syndrome
Testicular Cancer
Thymoma, Childhood
Thymoma and Thymic Carcinoma
Thyroid Cancer
Thyroid Cancer, Childhood
Transitional Cell Cancer of the Renal
Pelvis and Ureter
Trophoblastic Tumor, Gestational
Unknown Primary Site, Carcinoma of,
Adult
Unknown Primary Site, Cancer of,
Childhood
Unusual Cancers of Childhood
Ureter and Renal Pelvis, Transitional Cell
Cancer
Urethral Cancer
Uterine Cancer, Endometrial
Uterine Sarcoma
Vaginal Cancer
Visual Pathway and Hypothalamic
Glioma, Childhood
Vulvar Cancer
Waldenström's Macroglobulinemia
Wilms' Tumor Mesothelioma, Childhood
Metastatic Squamous Neck Cancer with Occult
Primary
Multiple Endocrine Neoplasia Syndrome,
Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma
of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive
Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell
Cancer
Retinoblastoma
Rhabdomyosarcoma, Childhood
Salivary Gland Cancer
Salivary Gland Cancer, Childhood
Sarcoma, Ewing's Family of Tumors
Sarcoma, Kaposi's
Sarcoma, Soft Tissue, Adult
Sarcoma, Soft Tissue, Childhood
Sarcoma, Uterine
Sezary Syndrome
Skin Cancer (non-Melanoma)
Skin Cancer, Childhood

TABLE 2

Examples of Anti-Cancer Agents

| | |
|---|---|
| 13-cis-Retinoic Acid | Mylocel |
| 2-Amino-6-Mercaptopurine | Letrozole |
| 2-CdA | Neosar |
| 2-Chlorodeoxyadenosine | Neulasta |
| 5-fluorouracil | Neumega |
| 5-FU | Neupogen |
| 6-TG | Nilandron |
| 6-Thioguanine | Nilutamide |
| 6-Mercaptopurine | Nitrogen Mustard |
| 6-MP | Novaldex |
| Accutane | Novantrone |
| Actinomycin-D | Octreotide |
| Adriamycin | Octreotide acetate |
| Adrucil | Oncospar |
| Agrylin | Oncovin |
| Ala-Cort | Ontak |
| Aldesleukin | Onxal |
| Alemtuzumab | Oprevelkin |
| Alitretinoin | Orapred |
| Alkaban-AQ | Orasone |
| Alkeran | Oxaliplatin |
| All-transretinoic acid | Paclitaxel |
| Alpha interferon | Pamidronate |
| Altretamine | Panretin |
| Amethopterin | Paraplatin |
| Amifostine | Pediapred |
| Aminoglutethimide | PEG Interferon |
| Anagrelide | Pegaspargase |
| Anandron | Pegfilgrastim |
| Anastrozole | PEG-INTRON |
| Arabinosylcytosine | PEG-L-asparaginase |
| Ara-C | Phenylalanine Mustard |
| Aranesp | Platinol |
| Aredia | Platinol-AQ |
| Arimidex | Prednisolone |
| Aromasin | Prednisone |
| Arsenic trioxide | Prelone |
| Asparaginase | Procarbazine |
| ATRA | PROCRIT |
| Avastin | Proleukin |
| BCG | Prolifeprospan 20 with Carmustine implant |
| BCNU | Purinethol |
| Bevacizumab | Raloxifene |
| Bexarotene | Rheumatrex |
| Bicalutamide | Rituxan |
| BiCNU | Rituximab |
| Blenoxane | Roveron-A (interferon alfa-2a) |
| Bleomycin | Rubex |
| Bortezomib | Rubidomycin hydrochloride |
| Busulfan | Sandostatin |
| Busulfex | Sandostatin LAR |
| C225 | Sargramostim |
| Calcium Leucovorin | Solu-Cortef |
| Campath | Solu-Medrol |
| Camptosar | STI-571 |
| Camptothecin-11 | Streptozocin |
| Capecitabine | Tamoxifen |
| Carac | Targretin |
| Carboplatin | Taxol |
| Carmustine | Taxotere |
| Carmustine wafer | Temodar |
| Casodex | Temozolomide |
| CCNU | Teniposide |
| CDDP | TESPA |
| CeeNU | Thalidomide |
| Cerubidine | Thalomid |
| cetuximab | TheraCys |
| Chlorambucil | Thioguanine |
| Cisplatin | Thioguanine Tabloid |
| Citrovorum Factor | Thiophosphoamide |
| Cladribine | Thioplex |
| Cortisone | Thiotepa |
| Cosmegen | TICE |
| CPT-11 | Toposar |

TABLE 2-continued

Examples of Anti-Cancer Agents

| | |
|---|---|
| Cyclophosphamide | Topotecan |
| Cytadren | Toremifene |
| Cytarabine | Trastuzumab |
| Cytarabine liposomal | Tretinoin |
| Cytosar-U | Trexall |
| Cytoxan | Trisenox |
| Dacarbazine | TSPA |
| Dactinomycin | VCR |
| Darbepoetin alfa | Velban |
| Daunomycin | Velcade |
| Daunorubicin | VePesid |
| Daunorubicin hydrochloride | Vesanoid |
| Daunorubicin liposomal | Viadur |
| DaunoXome | Vinblastine |
| Decadron | Vinblastine Sulfate |
| Delta-Cortef | Vincasar Pfs |
| Deltasone | Vincristine (LCR) |
| Denileukin diftitox | Vinorelbine |
| DepoCyt | Vinorelbine tartrate |
| Dexamethasone | VLB |
| Dexamethasone acetate | VP-16 |
| Dexamethasone sodium phosphate | Vumon |
| | Xeloda |
| Dexasone | Zanosar |
| Dexrazoxane | Zevalin |
| DHAD | Zinecard |
| DIC | Zoladex |
| Diodex | Zoledronic acid |
| Docetaxel | Zometa |
| Doxil | Gliadel wafer |
| Doxorubicin | Glivec |
| Doxorubicin liposomal | GM-CSF |
| Droxia | Goserelin |
| DTIC | granulocyte—colony stimulating factor |
| DTIC-Dome | Granulocyte macrophage colony stimulating factor |
| Duralone | Halotestin |
| Efudex | Herceptin |
| Eligard | Hexadrol |
| Ellence | Hexalen |
| Eloxatin | Hexamethylmelamine |
| Elspar | HMM |
| Emcyt | Hycamtin |
| Epirubicin | Hydrea |
| Epoetin alfa | Hydrocort Acetate |
| Erbitux | Hydrocortisone |
| Erwinia L-asparaginase | Hydrocortisone sodium phosphate |
| Estramustine | Hydrocortisone sodium succinate |
| Ethyol | Hydrocortone phosphate |
| Etopophos | Hydroxyurea |
| Etoposide | Ibritumomab |
| Etoposide phosphate | Ibritumomab Tiuxetan |
| Eulexin | Idamycin |
| Evista | Idarubicin |
| Exemestane | Ifex |
| Fareston | IFN-alpha |
| Faslodex | Ifosfamide |
| Femara | IL-2 |
| Filgrastim | IL-11 |
| Floxuridine | Imatinib mesylate |
| Fludara | Imidazole Carboxamide |
| Fludarabine | Interferon alfa |
| Fluoroplex | Interferon Alfa-2b (PEG conjugate) |
| Fluorouracil | Interleukin-2 |
| Fluorouracil (cream) | Interleukin-11 |
| Fluoxymesterone | Intron A (interferon alfa-2b) |
| Flutamide | Leucovorin |
| Folinic Acid | Leukeran |
| FUDR | Leukine |
| Fulvestrant | Leuprolide |
| G-CSF | Leurocristine |
| Gefitinib | Leustatin |
| Gemcitabine | Liposomal Ara-C |

TABLE 2-continued

Examples of Anti-Cancer Agents

| | |
|---|---|
| Gemtuzumab ozogamicin | Liquid Pred |
| Gemzar | Lomustine |
| Gleevec | L-PAM |
| Lupron | L-Sarcolysin |
| Lupron Depot | Meticorten |
| Matulane | Mitomycin |
| Maxidex | Mitomycin-C (MTC) |
| Mechlorethamine | Mitoxantrone |
| Mechlorethamine Hydrochlorine | M-Prednisol Mustargen |
| Medralone | Mustine |
| Medrol | Mutamycin |
| Megace | Myleran |
| Megestrol | Iressa |
| Megestrol Acetate | Irinotecan |
| Melphalan | Isotretinoin |
| Mercaptopurine | Kidrolase |
| Mesna | Lanacort |
| Mesnex | L-asparaginase |
| Methotrexate (MTX) | |
| Methotrexate Sodium | |
| Methylprednisolone | |

TABLE 3

Cytotoxicty of temozolomide (TMZ), etoposide (ETP), supercritical $CO_2$ extract of mango ginger (*Curcuma amada*) (CA), curcumin (CUR), Turmeric Force ™ (TF) in U-87MG human glioblastoma cell line.

| Drug/extracts | $IC_{50}$ (µg/ml) | $IC_{75}$ (µg/ml) | $IC_{90}$ (µg/ml) |
|---|---|---|---|
| TMZ | 175.50 ± 10.50 | >200 | >200 |
| ETP | 6.50 ± 2.54 | 127.50 ± 3.53 | >200 |
| CA | 4.92 ± 0.81 | 12.87 ± 0.85 | 21.30 ± 1.13 |
| CUR | 37.30 ± 4.04 | 51.00 ± 7.07 | >200 |
| TF | 38.51 ± 7.07 | 40.40 ± 2.97 | 48.50 ± 0.58 |

TABLE 4

Combination index values (CI) for drug/extract combinations in U-7MG cell line.

| Drug/extract combination | CI values at $IC_{50}$ | CI value at $IC_{75}$ | CI value at $IC_{90}$ |
|---|---|---|---|
| ETP + CA | 0.251 | 0.163 | 0.146 |
| TEM + CA | 0.253 | 0.520 | 0.476 |
| TEM + ETP + CA | 0.435 | 0.399 | 0.093 |
| TEM + ETP | 0.194 | 0.263 | 1.782 |

ETP, etoposide;
TEM, temozolomide;
CA, supercritical $CO_2$ extract of mango ginger (*Curcuma amada*)

| CI | | |
|---|---|---|
| | <0.1 | very strong synergism |
| | 0.1-0.3 | strong synergism |
| | 0.3-0.7 | synergism |
| | 0.8-0.9 | moderate to slight synergism |
| | 0.9-1.1 | nearly additive |
| | 1.1-1.45 | moderate to slight antagonism |
| | 1.45-3.3 | antagonism |
| | >3.3 | strong antagonism |

TABLE 5

Cytotoxicity of cancer drugs, supercritical extracts and their combination in embryonal (RD) and alveolar (SJRH30) rhabdomyosarcoma cell lines.

| | RD | | | SJRH30 | | |
|---|---|---|---|---|---|---|
| Drug/Extract | $IC_{50}$ (µg/ml) | $IC_{75}$ (µg/ml) | $IC_{90}$ (µg/ml) | IC50 (µg/ml) | IC75 (µg/ml) | IC90 (µg/ml) |
| Vinblastine (VBL) | 0.010 ± 0.002 | 0.200 ± 0.010 | >200 | 0.191 ± 0.010 | 36.110 ± 2.970 | >200 |
| Cyclophosphamide (CP) | 172.000 ± 8.530 | >200 | >200 | >200 | >200 | >200 |
| *C. amada* (CA) | 7.501 ± 0.540 | 16.010 ± 1.530 | 19.500 ± 2.170 | 7.133 ± 1.250 | 12.615 ± 1.480 | 18.442 ± 2.830 |
| *C. longa* (CL) | 12.040 ± 2.100 | 19.000 ± 1.970 | >200 | 7.730 ± 0.965 | 13.700 ± 1.751 | 18.425 ± 2.741 |
| *C. xanthorrhiza* (CX) | 16.048 ± 1.050 | 20.006 ± 1.580 | >200 | 13.311 ± 1.840 | 23.535 ± 2.573 | 47.125 ± 2.930 |
| VBL + CP | 0.004 ± 0.000 | 0.019 ± 0.001 | >200 | 0.150 ± 0.012 | 30.445 ± 2.650 | >200 |
| VBL + CA | 0.123 ± 0.010[a] | 0.185 ± 0.021[a] | 10.002 ± 1.750[a] | 0.008 ± 0.001[a] | 0.240 ± 0.011[a] | 0.780 ± 0.020[a] |
| VBL + CP + CA | 0.004 ± 0.000[a] | 0.005 ± 0.000[a] | 0.066 ± 0.001[a] | 0.011 ± 0.022[a] | 0.045 ± 0.008[a] | 0.122 ± 0.031[a] |
| VBL + CP + CL | 7.210 ± 0.100 | 19.006 ± 1.310 | >200 | 7.005 ± 1.024 | 16.350 ± 2.610 | >200 |
| VBL + CP + CX | 15.122 ± 1.550 | 20.050 ± 2.570 | >200 | 9.522 ± 1.141 | 20.445 ± 1.821 | >200 |

[a]Significant reduction in IC values compared to single agents

TABLE 6

Combination Index (CI) values for drug and extract combinations in embryonal (RD) and alveolar (SJRH30) rhabdomyosarcoma cell lines (analyzed by CompuSyn software).

| Drug/extract combination | RD | | | SJRH30 | | |
|---|---|---|---|---|---|---|
| | CI at $IC_{50}$ level | CI at $IC_{75}$ level | CI at $IC_{90}$ level | CI at $IC_{50}$ level | CI at $IC_{75}$ level | CI at $IC_{90}$ level |
| CP + CA | 0.498 | 0.477 | 0.508 | 0.662 | 0.551 | 0.459 |
| VBL + CA | 0.733 | 0.818 | 0.386 | 0.645 | 0.719 | 0.646 |
| CP + VBL + CA | 0.363 | 0.158 | 0.069 | 0.772 | 0.648 | 0.683 |

CP = cyclophosphamide;
CA = supercritical extract of Curcuma amada;
VBL = vinblastine
CI values <0.1 = very strong synergism;
0.10-0.30 = strong synergism;
0.30-0.70 = synergism;
0.70-0.85 = moderate synergism;
0.85-0.90 = slight synergism;
0.90-1.10 = nearly additive;
1.10-1.20 = slight antagonism;
1.20-1.45 = moderate antagonism;
1.45-3.30 = antagonism;
3.30-10 = strong antagonism;
>10 = very strong antagonism

TABLE 7

Certificate of Analysis Summary

| Feature | Method | Limits | Value Unit |
|---|---|---|---|
| Content of essential oil | GCMS, quantitative | n.s. | 10.2% |
| alpha Pinene | GCMS, quantitative | n.s. | 0.09% |
| Camphene | GCMS, quantitative | n.s. | 0.02% |
| beta Pinene | GCMS, quantitative | n.s. | 0.81% |
| beta Myrcene | GCMS, quantitative | n.s. | 5.6% |
| Limonene | GCMS, quantitative | n.s. | 0.03% |
| Ocimene | GCMS, quantitative | n.s. | 0.27% |
| Beta Caryophyllene | GCMS, quantitative | n.s. | 0.19% |
| Content of water | Karl Fischer method | <5.0 | 4.1% |
| fingerprint | HPLC | Standard | meets |
| (E)-Labda-8(17),12-diene-15,16 dial (LDD) | 21.204.01, HPLC | >35.0 | 53.2% |
| Content of Triglycerides | GCFID | n.s. | 3.1% | n.s. = not specified
n.d. = not detected

REFERENCES

Achut S G and Bandyopadhyaya C. "Characterization of mango-like aroma in Curcuma amada Roxb" J Agric Food Chem. 1984; 32:57-59.
Aggarwal B B, Kumar A, Bharti A C. "Anticancer potential of curcumin: preclinical and clinical studies" Anticancer Res. 2003; 23:363-398.
Amaral J D, Xavier J M, Steer C J, Rodrigues C M. "The role of p53 in apoptosis" Discov Med. 2010; 9:145-152.
Arlt A, Gehrz A, Muerkoster S, Vorndamm J, Kruse M L, Folsch U R and Schafer H. "Role of N F-kappaB and Akt/PI3K in the resistance of pancreatic carcinoma cell lines against gemcitabine-induced cell death" Oncogene 2003; 22:3243-3251.
Bellacosa A, Kumar C C, Di Cristofano A and Testa J R. "Activation of AKT kinases in cancer: implications for therapeutic targeting" Adv. Cancer Res. 2005; 94:29-86.
Bhaskaran A, S Rao Ravi, Subrahmanya P, Mahesh T S, and Krishnamurthy M S. "Clinical Evaluation of Amragandha Haridra (Curcuma Amada Roxb) in Pratisyaya W.S.R. to Allergic Rhinitis: A Folklore Claim" International Journal of Research in Ayurveda and Pharmacy 2012; 3(1): 85-89.
Chandrana H, Baluja S and Chanda S V. "Comparison of antibacterial activities of selected species of Zingiberaceae family and some synthetic compounds" Turk J Biol. 2005; 29:83-97.
Chappell W, Steelman L, Long J et al. "Ras/Raf/MEK/ERK and PI3K/PTEN/Akt/mTOR Inhibitors: Rationale and Importance to Inhibiting These Pathways in Human Health" Oncotarget, 2011; 2(3):135-164.
Cheah Y H, Azimahtol H L Abdullah N R. "Xanthorrhizol exhibits antiproliferative activity of MCF-7 breast cancer cells via apoptosis induction" Anticancer Res 2006; 26:4527-4534.
Cheng J Q, Jiang X, Fraser M, Li M, Dan H C, Sun M and Tsang B K. "Role of X-linked inhibitor of apoptosis protein in chemoresistance in ovarian cancer: possible involvement of the phosphoinositide-3 kinase/Akt pathway" Drug Resist. Update 2002; 5:131-146.
Chirangini P, Sharma G J, and Sinha S K. "Sulfur free radical activity with curcumin as reference for evaluating antioxidant properties of medicinal Zingiberales" J Environ Path Toxicol Oncol. 2004; 23:227-236.
Choi M A, Kim S H, Chung W Y, Hwang J K, Park K K. "Xanthorrhizol, a natural sesquiterpenoid form Curcuma xanthrorrhiza, has an anti-metastatic potential in experimental mouse lung metastasis model" Biochem Biophys Res Commun. 2005; 326:210-217.
Chou T C and Talalay P. "Analysis of combined drug effects: a new look at a very old problem" Trends Pharmacol Sci. 1983; 4:450-454.
Davicioni E, Anderson J, Finckenstein F G, Lynch J C Qualman S J, Shimada H, Schofield D E, Buckley J D, Meyer W H, Sorensen P H, Triche T J. "Molecular classification of rhabdomyosarcoma-genotypic and phenotypic determinants of diagnosis: a report from the Children's Oncology Group" Amer J Pathol. 2009; 174: 550-564.
Dewson G and Kluck R M. "Bcl-2 family-regulated apoptosis in health and disease" Cell Health Cytoskelet. 2010; 2:9-22.

Downward J. "PI 3-kinase, Akt and cell survival" *Semin. Cell. Dev. Biol.* 2004; 15:177-182.

Elmore S. "Apoptosis: A review of programmed cell death" *Toxicol Pathol.* 2007; 35:495-516.

Falasca M. "PI3K/Akt signaling pathway specific inhibitors: a novel strategy to sensitize cancer cells to anti-cancer drugs" *Curr. Pharm. Des.* 2010; 16:1410-1416.

Firuzi O, Miri R, Tavakkoli M, Saso L. "Antioxidant therapy: current status and future prospects" *Curr. Med. Chem.* 2011; 18(25):3871-3888.

Fulda S. "Cell death pathways as therapeutic targets in rhabdomyosarcoma" *Sarcoma* 2012; Vol. 2012; Article ID 326210; 5 pages.

Ghosh S B, Gupta s and Chandra A K. "Antifungal activity in rhizomes of *Curcuma amada* Roxb." *Indian J Exp Biol.* 1980; 18:174-176.

Gong D and Ferrell Jr J E. "The roles of Cyclin A2, B1 and B2 in early and late mitotic events" *Mol Biol Cell.* 2010; 21:3149-3161.

Gonzalzez M A, Mancebo-Aracil J, Tangarife-Castano V, Agudelo-Gomez L, Zapata B, Mesa-Arango A and Betancur-Galvis L. "Synthesis and biological evaluation of (+)-labdadienedial, derivatives and precursors from (+)-sclareolide" *Eur J Med Chem.* 2010; 45:4403-4408.

Greenlee R T, Murray T, Bolden S and Wingo P A. "Cancer Statistics" *CA Cancer J Clin.* 2000; 50:7-33.

Greider C W. "Telomerase activity, cell proliferation and cancer" *Proc Natl Acad Sci USA.* 1998; 95:90-92.

Hanahan D and Weinberg R A. "The hallmarks of cancer" *Cell* 2000; 100:57-70.

Huh W W, Skapek S X. "Childhood rhabdomyosarcoma: new insight on biology and treatment" *Curr Oncol Rep.* 2010; 12:401-410.

Hussain A, Virmani O P, Popli S P, Misra L N and Gupta M M. *Dictionary of Indian Medicinal Plants.* Central Institute of Medicinal Plants and Aromatic Plants. Lucknow 199; 2:39.

Islam M A. "Genetic diversity of the genus *Curcuma* in Bangladesh and further biotechnological approaches for in vitro regeneration and long-term conservation of *Curcuma longa* germplasm" Ph.D. thesis, University of Hanover, Germany; 2004.

Jatoi S A, Kikuch A, Gilani S and Watanabe K N. "Phytochemical, pharmacological and ethnobotanical studies in mango ginger (*Curcuma amada* Roxb.; Zingiberaceae)" *Phytother Res.* 2007; 21:507-516.

Kang Y J, Park K K, Chung W Y, Hwang J K, Lee S K. "Xanthorrhizol, a natural sequiterpenoid, induces apoptosis and growth arrest in HCT116 human colon cancer cells" *J Pharmacol Sci.* 2009; 111:276-284.

Kirtikar K R and Basu B D. Indian medicinal plants Vol. 4, second edition (Dehra Dun: Bishen Singh Mahendra Pal Singh) 1984; pp. 2422-2423.

Knuefermann C, Lu Y, Liu B, Jin W, Jiang K, Wu L, Schmidt M, Mills G B, Mendelsohn J and Fan Z. "HER2/PI-3K/Akt activation leads to a multidrug resistance in human breast adenocarcinoma cells" *Oncogene* 2003; 22:3205-3212.

Kroemer G, Galluzzi L, Brenner C. "Mitochondrial membrane permeabilization in cell death" *Physiol Rev* 2007; 87:99-163.

Kyo S, Takakura M, Taira T, Kanaya T, Itoh H, Yutsudo M, Hiroyoshi Ariga H and Inoue M. "Sp1 cooperates with c-Myc to activate transcription of the human telomerase reverse transcriptase gene (hTERT)" *Nucleic Acids Res.* 2000; 28:669-677.

Leevers S J, Vanhaesebroeck B and Waterfield M D. "Signaling through phosphoinositde-3-kinases: the lipids take center stage" *Current Opinion Cell Biology* 1999; 11:219-225.

Li R, Waga S, Hannon G J, Beach D and Stillman G J. "Differential effects by the p21 cdk inhibitor on PCNA-dependent DNA replication and repair" *Nature* 1994; 371:534-537.

Lin Z, Lim S, Viani M A, Sapp M and Lim M S. "Down-regulation of telomerase activity in malignant lymphomas by radiation and chemotherapeutic agents" *Am J. Pathol.* 2001; 159:405-410.

Majumdar A M., Naik D G, Dandge C N and Puntambekar H M. "Anti-inflammatory activity of *Curcuma amada* Roxb. in albino rats" *Indian J Pharmacol.* 2000; 32:375-377.

Malek S N A, Lee G S, Hong S L, Yascob H, Wahab N A, Weber J F and Shah S A A. "Phytochemical and cytotoxic investigations of *Curcuma mangga* rhizomes" *Molecules* 2011; 16:4539-4548.

Malempati S and Hawkins D S. "Rhabdomyosarcoma: review of the Children's Oncology Group (COG) Soft-Tissue Sarcoma Committee experience and rationale for current COG studies" *Pediatr Blood Cancer* 2012; 59:5-10.

Mandell L R. "Ongoing progress in the treatment of childhood rhabdomyosarcoma" *Oncology* 1993; 7:71-83.

Mayo L D and Donner D B. "The PTEN, Mdm2, p53 tumor suppressor-oncoprotein network" *Trends Biochem. Sci.* 2002; 27:462-467.

McCubrey J, Steelman L, Chappell W et al. "Ras/Raf/MEK/ERK and PI3K/PTEN/Akt/mTOR Cascade Inhibitors: How Mutations Can Result in Therapy Resistance and How to Overcome Resistance" *Oncotarget* 2012; 3(10):1068-1111.

Minard-Colin V, Ichante J L, Nguyen L, Paci A, Orbach D, Bergeron C, Defachelles A S, André N, Corradini N, Schmitt C, Tabone M D, Blouin P, Sirvent N, Goma G, Geoerger B, Oberlin O. "Phase II study of vinorelbine and continuous low doses cyclophosphamide in children and young adults with a relapsed or refractory malignant solid tumour: good tolerance profile and efficacy in rhabdomyosarcoma—a report from the Société Française des Cancers et leucémies de l'Enfant et de l'adolescent (SFCE)" *Eur J Cancer* 2012; 48:2409-2416.

Nagata Y, Lan K H, Zhou X, Tan M, Esteva F J, Sahin A A, Klos K S, Li P, Monia B P, Nguyen N T, Hortobagyi G N, Hung M C, and Yu D. "PTEN activation contributes to tumor inhibition by trastuzumab, and loss of PTEN predicts trastuzumab resistance in patients" *Cancer Cell* 2004; 6(2):117-127.

Niranjan A, Prakash D, Tewari S K, Pande A and Pushpangadan P. "Chemistry of *Curcuma* species cultivated on sodic soil" *J Med Aromat Plant Sci.* 2003; 25:69-75.

Oltivai Z N, Millman C L and Korsmeyer S J. "Bcl-2 heterodimerises in vivo with a conserved homolog, Bax, that accelerates programmed cell death" *Cell* 1993; 74:609-619.

Pachauri S P and Mukherjee S K. "Effect of *Curcuma longa* (Haridra) and *Curcuma amada* (Amragandhi) on the cholesterol level in experimental hypercholesterolemia of rabbits" *J Res Indian Med.* 1970; 5:27-30.

Pappo A S, Cristo W M, Wharam M D, Hawkins D, Raney R B, Womer R B, Parham D M, Qualman S J, Grier H E. "Survival after relapse in children and adolescents with rhabdomyosarcoma: A report from the Intergroup Rhabdomyosarcoma Study Group" *J Clin Oncol.* 1999; 17:3487-3493.

Park J H, Park K K, Kim M J, Hwang J K, Park S K, Chung W Y. "Cancer chemoprotective effects of *Curcuma xanthorrhiza*" *Phytother Res.* 2008; 22:695-698.

Perry M C, Demeule M, Regina A, Moumdjian R and Beliveau R. "Curcumin inhibits tumor growth and angiogenesis in glioblastoma xenografts" *Mol Nutr Food Res.* 2010; 54:1192-1201.

Policegoudra R S, Divakar S and Aradhya S M. "Identification of difurocumenonol, a novel antimicrobial compound from mango ginger (*Curcuma amada* Roxb.) rhizome" *J Appl Microbiol.* 2007a; 102: 1596-1602.

Policegoudra R S, Abiraj K, Channe Gowda D and Aradhya S M. "Isolation and characterization of antioxidant and antibacterial compound from mango ginger (*Curcuma amada* Roxb.) rhizome" *J Chromatogr.* 2007b; B854:40-48.

Policegoudra R S. "Functional properties of bioactive molecules from mango ginger (*Curcuma amada* Roxb.) and its applications in food" Ph.D. Thesis, Mysore University, Mysore, India; 2008.

Policegoudra R S, Rehna K, Jaganmoha Rao L and Aradhya S M. "Antimicrobial, antioxidant, cytotoxicity and platelet aggregation inhibitory activity of a novel isolated and characterized from mango ginger (*Curcuma amada* Roxb.) rhizome" *J Biosci.* 2010; 35:231-240.

Policegoudra R S, Aradhya S M and Singh L. "Mango ginger (*Curcuma amada* Roxb.)—A promising spice for phytochemicals and biological activities" *J Biosci.* 2011; 36:739-748.

Pommier Y, Sordet O, Antony S, Hayward R L and Kohn K W. "Apoptosis defects and chemotherapy resistance: molecular interaction maps and networks" *Oncogene* 2004; 23:2934-2949.

Ramachandran C, Nair P K R, Alamo A, Cochrane C B, Escalon E, Melnick S J. "Anticancer effects of amooranin in human colon carcinoma cell line in vitro and in nude mice xenorgrafts" *Int J Cancer* 2006; 119:243-254.

Ramachandran C, Nair S M, Escalon E, and Melnick S J. "Potentiation of etoposide and temozolomide cytotoxicity by curcumin and turmeric Force™ in brain tumor cell lines" *J Complement Integr Med.* 2012; Vol. 9, Issue 1; Article 20 (14 pages).

Ramachandran C, Quirin K-W, Escalon E, Lollett, I V and Melnick S J. "Therapeutic effect of supercritical $CO_2$ extracts of *Curcuma* species with cancer drugs in rhabdomyosarcoma cell lines" *Phytother Res.* 2015; 29(8): 1152-1160.

Ramachandran C, Resek A P, Escalon E, Aviram A. and Melnick S J. "Potentiation of gemcitabine by Turmeric Force™ in pancreatic cancer cell lines" *Oncol Rep.* 2010; 23:1529-1535.

Ramachandran C, Wellham L L. "Effect of MDR1 phosphorothioate antisense oligodeoxynucleotides in multidrug-resistant human tumor cell lines and xenografts" *Anticancer Res.* 2003; 23:2681-2690.

Regina A, Demeule M, Laplante A, Jodoin J, Dagenais C, Berthelet F, Moghrabi A and Beliveau R. "Multidrug resistance in brain tumors: Roles of the blood-brain barrier" Cancer Metastasis Rev. 2001; 20:13-25.

Saab R, Spunt S L, Skapek S X. "Myogenesis and rhabdomyosarcoma: the Jekyll and hyde of skeletal muscle" *Curr Top Dev Biol* 2011; 94:197-234.

Samant L. "*Curcuma amada* Roxb.: A Phytopharmacological Review" *J. Pharm. Res.* 2012; 5(4):1992-1993.

Schuler M, Bossy-Wetzel E, Goldstein J C, Fitzgerald P, Green D R. "p53 induces apoptosis by caspase activation through mitochondrial cytochrome c release" *J Biol Chem.* 2000; 275:7337-7342.

Seitz G, Warmann S W, Vokuhl C O, Heitmann H, Treuner C, Leuschner I, Fuchs J. "Effects of standard chemotherapy on tumor growth and regulation of multidrug resistance genes and proteins in childhood Rhabdomyosarcoma" *Pediatric Surg Int.* 2007; 23:431-439.

Shay J W and Bacchetti S. "A survey of telomerase activity in human cancer" *Eur J Cancer* 1997; 33:787-791.

Sheeja A D B and Nair M S. "Facile isolation of (E)-labda-8(17)12-diene-15,16-dial from *Curcuma amada* and its conversion to other biologically active compounds" *Indian J Chem.* 2014; 53B:319-324.

Sheeja A D B and Nair M S. "Phytochemical constituents of *Curcuma amada*" *Biochem System Ecol.* 2012; 44:264-266.

Singh G, Singh O P, and Maurya S. "Chemical and biocidal investigations on essential oils of some Indian *Curcuma* species" *Prog Crystal Growth Character Mater.* 2002; 45:75-81.

Singh G, Singh O P, de Lampasona M P, and Catalan C. "*Curcuma amada* Roxb. —chemical composition of rhizome oil" *Indian Perfumer.* 2003; 47:143-146.

Singh S, Jonnala K K, Dharmendra S, Karuna S, Jay P T, Arvind S N and Suchitra B. "A bioactive labdane diterpenoid from *Curcuma amada* and its semisynthetic analogues as antitubercular agents" *Eur J Med Chem.* 2010; 45:4379-4382.

Singh S, Singh R., Banerjee S, Negi A S, Shanker K. "Determination of anti-tubercular agent in mango ginger (*Curcuma amada* Roxb.) by reverse phase HPLC-PDA-M S, chapter 2.4". *Food Chem* 2012; 131:375-379.

Speirs C K, Hwang M, Kim S, Li W, Chang S, Varki V, Mitchell L, Schleicher S and Lu B. "Harnessing the cell death pathway for targeted cancer treatment" *Am J Cancer Res.* 2011; 1:43-61.

Srinivas Rao A, Bandaru R and Ramachandran S. "Volatile aroma components of *Curcuma amada* Roxb" *J Agric Food Chem.* 1989; 37:740-743.

Stahl E, Quirin K-W, and Gerard, D. "Dense Gases for Extraction and Refining" Springer-Verlag, New York Heidelberg Berlin; ISDN 0-387-18158-X; 1988.

Steelman L, Chappell W, Abrams S et al. "Roles of the Raf/MEK/ERK and PI3K/PTEN/Akt/mTOR pathways in controlling growth and sensitivity to therapy-implications for cancer and aging" *Aging,* 2011; 3(3):192-222.

Sun M, Yang L, Feldman R I, Sun X M, Bhalla K N, Jove R, Nicosia S V and Cheng J Q. "Activation of phosphatidylinositol 3-kinase/Akt pathway by androgen through interaction of p85alpha, androgen receptor, and Src" *J. Biol. Chem.* 2003; 278:42992-43000.

Tee T T, Chea Y H, Meenakshii N, Mohd Sharom M Y, Azimahtol Hawariah L P. "Xanthorrhizol induced. DNA fragmentation in HepG2 cells involving Bcl-2 family proteins" *Biochem Biophys Res Commun.* 2012; 420:834-838.

Vaux D L, Cory S and Adams J M. "Bcl-2 gene promotes haemopoietic cell survival and cooperates with c-myc to immortalize pre-B cells" *Nature* 1988; 335:440-442.

Warrier P K, Nambiar V P K and Ramankutty C. Indian medicinal plants—a compendium of 500 species, Chennai: Orient Longman Pvt. Ltd, vol. 1 p. 106; 1994.

Whang Y E, Yuan X J, Liu Y, Majumder S and Lewis T D. "Regulation of sensitivity to TRAIL by the PTEN tumor suppressor" Vitamins Hormones 2004; 67:409-426.

Wolff S, Erster S, Palacios G, Moll U M. "p53's mitochondrial translocation and MOMP action is independent of Puma and Bax and severely disrupts mitochondrial membrane integrity" Cell Res. 2008; 18:733-744.

Woodgett J R. "Recent advances in the protein kinase B signaling pathway" *Current Opinion in Cell Biology* 2005; 17:150-157.

Youle R J and Strasser A. "The BCL-2 protein family: opposing activities that mediate cell death" *Nature* Rev Mol Cell Biol. 2008; 9:47-59.

Zhou B P and Hung M C. "Novel targets of Akt, p21(Cipl/WAF1), and MDM2" *Semin. Oncol.* 2002; 29:62-70.

We claim:

1. A method for treating a condition in a subject having the condition, comprising administering an effective amount of a supercritical carbon dioxide extract of *Curcuma amada* to the subject, wherein the extract comprises (E)-Labda-8(17),12-diene-15,16-dial (LDD), and wherein the condition is selected from the group consisting of a cell proliferation disorder and inflammation.

2. The method of claim 1, wherein the extract comprises at least about 5% LDD.

3. The method of claim 1, wherein the extract comprises α-pinene, camphene, β-pinene, β-myrcene, limonene, β-phellandrene, β-cariophyllene, ar-curcumene, α-zingiberene, and LDD.

4. The method of claim 1, wherein said administering comprises administering a composition to the subject, and wherein the composition comprises an effective amount of the extract and further comprises a natural or synthetic oil.

5. The method of claim 1, wherein said administering comprises administering a composition to the subject, and wherein the composition comprises an effective amount of the extract and further comprises an agent selected from among a botanical extract, mineral, vitamin, nutrient, other nutraceutical, dietary supplement, or active pharmaceutical ingredient.

6. The method of claim 1, wherein the condition is a cell proliferation disorder.

7. The method of claim 1, wherein the condition is inflammation.

8. The method of claim 6, wherein the cell proliferation disorder is cancer.

9. The method of claim 1, wherein said administering comprises orally administering the extract to the subject.

10. The method of claim 1, wherein the extract comprises at least 5% LDD.

11. The method of claim 1, wherein the extract comprises at least 10% LDD.

12. The method of claim 1, wherein the extract comprises at least 50% LDD.

* * * * *

UNITED STATES PATENT AND TRADEMARK OFFICE
CERTIFICATE OF CORRECTION

PATENT NO. : 10,568,925 B2  
APPLICATION NO. : 15/011628  
DATED : February 25, 2020  
INVENTOR(S) : Steven J. Melnick et al.

Page 1 of 1

It is certified that error appears in the above-identified patent and that said Letters Patent is hereby corrected as shown below:

In the Specification

Column 6,  
Line 65, "30A-301:" should read --30A-30I:--.

Column 27,  
Lines 13-14, "3-cariophyllene," should read --β-cariophyllene,--.

Column 32,  
Lines 17-18, "3-pinene, 3-myrcene, limonene, 3-phellandrene," should read --β-pinene, β-myrcene, limonene, β-phellandrene,--.

Column 42,  
Line 62, "UNSCAN-IT GEL' software" should read --UNSCAN-IT GEL™ software--.

Column 46,  
Line 37, "Tumeric Force" should read --Tumeric Force™--.

Signed and Sealed this  
Thirtieth Day of June, 2020

Andrei Iancu  
*Director of the United States Patent and Trademark Office*